US007910718B2

(12) United States Patent
Simkin et al.

(10) Patent No.: US 7,910,718 B2
(45) Date of Patent: Mar. 22, 2011

(54) OLEOSIN GENES AND PROMOTERS FROM COFFEE

(75) Inventors: Andrew Simkin, Tours (FR); James Gérard McCarthy, Noizay (FR); Vincent Petiard, Tours (FR); Steven D. Tanksley, Dryden, NY (US); Chenwei Lin, Ithaca, NY (US)

(73) Assignees: Nestec S.A., Vevey (CH); Cornell Research Foundation, Ithaca, NY (US)

( * ) Notice: Subject to any disclaimer, the term of this patent is extended or adjusted under 35 U.S.C. 154(b) by 343 days.

(21) Appl. No.: 11/988,045

(22) PCT Filed: Jun. 30, 2006

(86) PCT No.: PCT/US2006/026121
§ 371 (c)(1),
(2), (4) Date: Dec. 28, 2007

(87) PCT Pub. No.: WO2007/005928
PCT Pub. Date: Jan. 11, 2007

(65) Prior Publication Data
US 2009/0229007 A1 Sep. 10, 2009

Related U.S. Application Data

(60) Provisional application No. 60/696,445, filed on Jul. 1, 2005.

(51) Int. Cl.
*C07H 21/04* (2006.01)
*C12N 15/82* (2006.01)
*C12N 15/20* (2006.01)
*A01H 5/00* (2006.01)

(52) U.S. Cl. ...... 536/24.1; 536/23.6; 800/278; 800/287; 435/320.1

(58) Field of Classification Search .......................... None
See application file for complete search history.

(56) References Cited

U.S. PATENT DOCUMENTS

| 6,137,032 A | 10/2000 | Cheng et al. |
| 6,146,645 A | 11/2000 | Deckers et al. |

FOREIGN PATENT DOCUMENTS

| WO | WO 01/36648 | 5/2001 |
| WO | WO 2004/013304 | 2/2004 |
| WO | WO 2004/111244 | 12/2004 |
| WO | WO 2004/113520 | 12/2004 |
| WO | WO 2005/047455 | 5/2005 |

OTHER PUBLICATIONS

Stalberg et al, Plant Molecular Biology, vol. 23, pp. 671-683, 1993.*
Doelling et al 1995, Plant J. 8:683-692.*
Bustos et al ,The EMBO Journal (1991) vol. 10, pp. 1469-1479.*
Benfey et al, 1990, Science 250:959-966.*
Maiti et al, 1997, Transgen. Res., 6:143-156.*
Chen, J.C.F. et al., "Cloning, Expression and Isoform Classification of a Minor Oleosin in Sesame Oil Bodies," *Journal of Biochemistry* (Tokyo), vol. 122(4), Oct. 1997, pp. 819-824 XP002416737, ISSN: 0021-924X, pp. 821 and 822.
Database EMBL Online, Database Accession No. AF498264 whole document, "Sesamum Indicium Steroleosin-B mRNA," complete cds, XP002433925, Jun. 3, 2002.
Database EMBL Online, Database Accession No. AY841276, whole document, "Coffee Canephora STO-1 mRNA", complete cds, XP002433929, Dec. 23, 2005.
Database EMBL Online, Database Accession No. AY928084, whole document, "Coffee Arabica Oleosin mRNA", complete cds, XP002417645, Dec. 23, 2005.
Database EMBL Online, Database Accession No. U97700, whole document, "Sesamum Indicum 15/5 kDa Oleosin MRNA", complete cds. XP002417644, Jun. 2, 1997.
Leprince, O. et al., "Oleosins Prevent Oil-Body Coalescence During Seed Imbibition . . . ", *Planta*, Springer Verlag, DE. vol. 204, 1998, pp. 109-119, XP000885490, ISSN: 0032-0935, Abstract Table 2.
Simkin. a J. et al., "Oleosin Gene Gamily of Coffee Canephora: Quantitive Expression Analysis of five Oleosin Genes in Developing and Germinating Coffee Grain," *Journal of Plant Physiology*, vol. 163(7), May 2006, pp. 691-708 XP002416738, the whole document.
Lin, Li-Jen et al., "Two Distinct Steroleosin are Present in Seed Oil Bodies," *Plant Physiology and Biochemistry* (Paris), vol. 42(7-8), Jul. 2004, pp. 601-608, XP004545182, Figure 1.
Kim, Hyun U.K. et al., "A Novel Group of Oleosins is Present Inside the Pollen of *Arabidopsis*", *Journal of Biological Chemistry*, vol. 277(25), Jun. 21, 2002, pp. 22677-22684, XP002416739, the whole document.
Lin, Li-Jen et al., "Steroleosin, a Sterol-Binding Dehydrogenase in Seed Oil Bodies", *Plant Physiology* (Rockville), vol. 128(4), Apr. 2002, pp. 1200-1211, XP002416741.
Murphy, D.J. et al., "Role of Lipid Bodies and Lipid-Body Proteins in Seeds and Other Tissues," *Journal of Plant Physiology*, vol. 158(4), Apr. 2001, pp. 471-478, XP002416740, the whole document.
Aalen, R.B. et al., "Transcripts Encoding an Oleosin and a Dormancy-Related Protein are Present in Both the Aleurone Layer and the Embryo of Developing Barley (*Hordeum vulgare* L.) Seeds," *Plant J.* 5(3):385-396, (1994).
Aalen, R.B. "The Transcripts Encoding Two Oleosin Isoforms are Both Present in the Aleurone and in the Embryo of Barley (*Hordeum vulgare* L.) Seeds," *Plant Mol. Biol.* 28(3):583-588, (1995).
Abell, B.M. et al., "Role of the Proline Knot Motif in Oleosin Endoplasmic Reticulum Topology and Oil Body Targeting," *Plant Cell.* 9(8):1481-1493 (1997).
Akiyama, M. et al., Analysis of Volatile Compounds Released During the Grinding of Roasted Coffee Beans Using Solid-Phase Microextraction. *J Agric Food Chem.* 51(7):1961-1969, (2003).
Allen, R.D. et al., "Nuclear Factors Interact With a Soybean B-Conglycinin Enhancer," *Plant Cell.* 1: 623-631, (1989).

(Continued)

*Primary Examiner* — Eileen B O Hara
(74) *Attorney, Agent, or Firm* — Potter Anderson & Corroon LLP

(57) ABSTRACT

Oleosin- and steroleosin-encoding polynucleotides from coffee plants are disclosed. Also disclosed are promoter sequences from coffee oleosin genes, and methods for using these polynucleotides and promoters for gene regulation and manipulation of flavor, aroma and other features of coffee beans.

20 Claims, 14 Drawing Sheets

OTHER PUBLICATIONS

Bäumlein, H. et al., Cis-Analysis of a Seed Protein Gene Promoter: the Conservative RY Repeat CATGCATG Within the Legumin Box Is Essential for Tissue-Specific Expression of a Legumin Gene, *Plant J.* 2: 233-239, (1992).

Beaudoin, F. et al., Targeting and Membrane-Insertion of a Sunflower Oleosin in Vitro and in *Saccharomyces cerevisiae*: the Central Hydrophobic Domain Contains More Than One Signal Sequence, and Directs Oleosin Insertion Into the Endoplasmic Reticulum Membrane Using a Signal Anchor Sequence Mechanism. *Planta* 215(2): 293-303, (2002).

Chamberland, S. et al., "The Leguminin Boxes and the 3' Part of a Soybean B-Conglycinin Promoter are Involved in Seed Gene Expression in Transgenic Tobacco Plants," *Plant Mol. Biol.* 19: 937-949, (1992).

Chatthai, M. et al., "2S Storage Protein Gene of Douglas-Fir: Characterization and Activity of Promoter in Transgenic Tobacco Seeds," *Plant Physiol. Biochem.* 42(5): 417-23, (2004).

Chen, J.C.F. et al., "Cloning, Expression and Isoform Classification of a Minor Oleosin in Sesame Oil Bodies," *J. Biochem.* 122 (4): 819-824, (1997).

Chen, M.C.M. et al., "Constitution of Stable Artificial Oil Bodies With Triacylglycerol, Phospholipid, and Caleosin," *J Agric Food Chem* 52, 3982-3987, (2004).

Chia, T.Y. et al., "Storage Oil Breakdown During Embryo Development of *Brassica napus* (L.)," *J Exp Bot.* 56(415):1285-1296, (2005).

Chiba, A. et al., "Exclusion of Ribulose-1,5-Bisphosphate Carboxylase/Oxygenase From Chloroplasts by Specific Bodies in Naturally Senescing Leaves of Wheat," *Plant Cell Physiol.* 44, 914-921, (2003).

Chuang, R.L. et al., "Characterization of Seed Oil Bodies and Their Surface Oleosin Isoforms From Rice Embryos," *J. Biochem* 120(1): 74-81, (1996).

Clough, S.J. et al., "Floral Dip: a Simplified Method for *Agrobacterium*-Mediated Transformation of *Arabidopsis thaliana*," *Plant Journal* 16; 735-743, (1998).

Crouzillat, D., "*Theobroma cacao* L.: a Genetic Linkage Map and Quantitative Trait Loci Analysis," *Theor. Appl. Genet.* 93: 205-214, (1996).

Dickinson, C.D. et al., "RY Repeats are Conserved in the 5'-Flanking Regions of Legume Seed-Protein Genes." *Nucleic Acids Res.* 16(1):371, (1988).

Donaire, J.P. et al., "Lipid Biosynthesis, Oxidative Enzyme Activities and Cellular Changes in Growing Olive Fruit," *Rev Esp Fisiol.* 40(2):191-203, (1984).

Fernandez-Moya, V. et al., "Metabolism of Triacylglycerol Species During Seed Germination in Fatty Acid Sunflower (*Helianthus annuus*) Mutants," *J Agric Food Chem.*48(3):770-774, (2000).

Froese, C.D. et al., "Molecular Composition and Surface Properties of Storage Lipid Particles in Wax Bean (*Phaseolus vulgaris*)," *J Plant Physiol.* 160(3):215-225, (2003).

Garcia-Mas, J. et al., "Molecular Characterization of cDNAs Corresponding to Genes Expressed During Almond (*Prunus amygdalus* Batsch) Seed Development," *Plant Mol. Biol.* 27 (1), 205-210, (1995).

Guilloteau, M. et al., "Oil Bodies in Theobroma Cacao Seeds: Cloning and Characterization of Cdna Encoding the 15.8 and 16.9 Kda Oleosins," *Plant Sci.* 164 (4): 597-606, (2003).

Hammond-Kosack, M.C.U. et al., "In Vitro Footprinting of a Low Molecular Weight Glutenin Gene (LMWG-1D1) in Wheat Endosperm," *EMBO J.* 12: 545-554, (1993).

Hernandez-Pinzon, I. et al., "Composition and Role of Tapetal Lipid Bodies in the Biogenesis of the Pollen Coat of *Brassica napus*," *Planta* 208: 588-589, (1999).

Hsieh, K. and Huang A.H.C., "Endoplastic Reticulum, Oleosins, and Oils in Seeds and Tapetum Cells," *Plant Phys.* 136: 3427-3434, (2004).

Huang, A.H.C., "Oil Bodies and Oleosins in Seeds," *Ann Rev Plant Phys Mol Biol* 43:177-200, (1992).

Huang, A.H.C., "Oleosins and Oil Bodies in Seeds and Other Organs," *Plant Physiol.* 110(4): 1055-1061, (1996).

Hughes, D.W. et al., "Cotton (*Gossypium hirsutum*) Matp6 and Matp7 Oleosin Genes," *Plant Physiol.* 101 (2): 697-698 (1993).

Jolivet, P. et al., "Protein Composition of Oil Bodies in *Arabidopsis thaliana* Ecotype WS," *Plant Physiol Biochem.* 42(6): 501-509, (2004).

Kawagoe, Y. and Murai, N., "Four Distinct Nuclear Proteins Recognize in Vitro the Proximal Promoter of the Bean Seed Storage Protein B-Phaseolin Gene Conferring Spatial and Temporal Control," *Plant J.* 2: 927-936, (1992).

Keddie, J.S. et al., "Sequence of an Oleosin cDNA From *Brassica napus*," *Plant Mol. Biol.* 19 (6): 1079-1083, (1992).

Keddie, J.S. et al., "A Seed-Specific *Brassica napus* Oleosin Promoter Interacts With a G-Box-Specific Protein and May Be Bi-Directional," *Plant Mol. Bio.* 24: 327-340, (1994).

Kim, H.U. et al., "A Novel Group of Oleosins is Present Inside the Pollen of *Arabidopsis*," *J. Biol Chem.* 277(25): 22677-22684, (2002).

Lee, K. and Huang, A.H. "Genes Encoding Oleosins in Maize Kernel of Inbreds Mo17 and B73," *Plant Mol.Biol.* 26(6): 1981-1987, (1994).

Lee, K. et al., "Genetic Dissection of the Co-Suppression of Genes Encoding the Isoforms of Oleosins in the Oil Bodies of Maize Kernel," *Plant J.* 7(4): 603-611, (1995).

Lelievre, J.M. et al., "5'-CATGCAT-3' Elements Modulate the Expression of Glycinin Genes," *Plant Physiol.* 98: 387-391, (1992).

Li, M., "Purification and Structural Characterisation of the Central Hydrophoblic Domain of Oleosin," *J. Biol. Chem.* 277(40): 37888-37895, (2002).

Lin, L.J. et al., "Steroleosin, a Sterol-Binding Dehydrogenase in Seed Oil Bodies," *Plant Physiol* 128(4):1200-1211, (2002).

Lin, L.J. and Tzen, J.T., "Two Distinct Steroleosins are Present in Seed Oil Bodies," *Plant Physiol Biochem.* 42(7-8): 601-608, (2004).

Maier, U.G. et al., "Binding of a Nuclear Factor to a Consensus Sequence in the 5' Flanking Region of Zein Genes From Maize," *EMBO J.* 6: 17-22, (1987).

Marraccini, P. et al., "Rubisco Small Subunit of *Coffea arabica*: cDNA Sequence, Gene Cloning and Promoter Analysis in Transgenic Tobacco Plants," *Plant Physiol. Biochem.* 41:17-25, (2003).

Marraccini, P. et al., "Molecular Cloning of the Complete 11S Seed Storage Protein Gene of *Coffea arabica* and Promoter Analysis in Transgenic Tobacco Plants," *Plant Physiol. Biochem.* 37(4): 273-282, (1999).

Marriott, K.M. and Northcote, D.H., the breakdown of lipid reserves in the endosperm of germinating castor beans. *Biochem J.*148(1):139-144, (1975).

Murphy, D.H. et al., "New Insights Into the Mechanisms of Lipid-Body Biogenesis in Plants and Other Organisms," *Biochem. Soc. Trans.* 28(6): 710-711, (2000).

Murphy, D.H. and Ross, J.H.E., "Biosynthesis, Targeting and Processing of Oleosin-Like Proteins, Which are Major Pollen Coat Components in *Brassica napus*," *Plant J.* 13: 1-16, (1998).

Naested, H. et al., "Calosins: $Ca^{2+}$-Binding Proteins Associated With Lipid Bodies," *Plant Mol. Biol.* 44: 463-476, (2000).

Naot, D. et al., "Induction of a Gene Encoding an Oleosin Homologue in Cultured Citrus Cells Exposed to Salt Stress" *Gene* 161: 171-173, (1995).

Penfield, S. et al., "Reserve Mobilization in the *Arabidopsis* Endosperm Fuels Hypocotyl Elongation in the Dark, Is Independent of Abscisic Acid, and Requires Phosphoenolpyruvate Carboxykinase 1." *Plant Cell* 16(10):2705-2718, (2004).

Pritchard, S.L. et al., "Germination and Storage Reserve Mobilization are Regulated Independently in *Arabidopsis*," *Plant J.* 31(5):639-647, (2002).

Qu, R.D. and Huang, A.H. "Oleosin KD 18 On the Surface of Oil Bodies in Maize. Genomic and Cdna Sequences and the Deduced Protein Structure," *J. Biol. Chem.* 265 (4): 2238-2243, (1990).

Rogers, W.J. et al., "Biochemical and Molecular Characterisation and Expression of the 11 S-Type Storage Protein From *Coffea arabica* Endosperm," *Plant Physiol. Biochem.* 37(4): 261-272, (1999).

Shirsat, A. et al., "Sequences Responsible for the Tissue Specific Promoter Activity of a Pea Legumin Gene in Tobacco," *Mol. Gen. Genet.* 215(2): 326-331, (1989).

Simkin, A.J. et al., "Circadian Regulation of the Phccd1 Carotenoid Dioxygenase Controls Emission of B-Ionone, a Fragrance Volatile of Petunia Flowers," *Plant Physiol.* 136(3): 3504-3514 (2004b).

Simkin, A.J. et al., "Plastid Lipid Associated Proteins of the Fibrillin Family: Structure, Localisation, Function and Gene Expression," *Rec. Res. Dev. Biochem.* 5: 307-316, (2004a).

Slack, C.R. et al., "Some Studies of the Composition and Surface of Oil Bodies From the Seed Cotyledons of Safflower and Linseed," *Biochem. J.* 190: 551-561, (1980).

Tai SS, Chen MC, Peng CC, Tzen JT. (2002). Gene Family of Oleosin Isoforms and Their Structural Stabilization in Sesame Seed Oil Bodies. *Biosci. Biotech. Biochem.* 66(10): 2146-2153.

Takaiwa, F. et al., "Characterization of Common Cis-Regulatory Elements Responsible for the Endosperm-Specific Expression of Members of the Rice Glutelin Multigene Family," *Plant Mol. Biol.* (30):1207-1221, (1996).

Tan, B.C. et al., "Molecular Characterization of the *Arabidopsis* 9-Cis Epoxycarotenoid Dioxygenase Gene Family," *Plant J.* 35:1-13, (2003).

Thomas, T.L. "Gene Expression During Embryogenesis and Germination: an Overview," *Plant Cell* (5): 1401-1410, (1993).

Thoyts, P.J. et al., "Expression and in Vitro Targeting of a Sunflower Oleosin," *Plant Mol. Biol.* 29 (2):403-410, (1995).

Ting, J.T.L,, "Oleosin Genes in Maize Kernels Having Diverse Oil Contents are Constitutively Expressed Independent of Oil Contents. Size and Shape of Intracellular Oil Bodies are Determined by Oleosins/Oil Ratio," *Planta*, 199: 158-165, (1996).

Tzen, J.T.C, "Lipids, Proteins, and Structure of Seed Oil Bodies From Diverse Species," *Plant Physiol.*, 101: 267-276, (1993).

Tzen, J.T.C., "Coexistence of Both Oleosin Isoforms on the Surface of Seed Oil Bodies and Their Individual Stabilization to the Organelles," *J. Biochem.*, 123: 318-323, (1998).

Tzen, J.T.C., "Oleosin Isoforms of High and Low Molecular Weights are Present in the Oil Bodies of Diverse Seed Species," *Plant Physiol.*, 94: 1282-1289, (1990).

Variyar, P.S. et al., "Flavoring Components of Raw Monsooned Arabica Coffee and Their Changes During Radiation Processing," *J Agric Food Chem.* 51(27):7945-7950, (2003).

Wahlroos, T. et al., "Oleosin Expression and Trafficking During Oil Body Biogenesis in Tobacco Leaf Cells," *Genesis* 35: 125-132, (2003).

Washida, H. et al., "Identification of Cis-Regulatory Elements Required for Endosperm Expression of the Rice Storage Protein Glutelin Gene *Glub-1*," *Plant Mol. Biol.* (40) 1-12, (1999).

Wu, L.S.H. et al., "Classification of the Single Oleosin Isoform and Characterization of Seed Oil Bodies in Gymnosperms," *Plant Cell Physiol.* 40: 326-334, (1999).

Wu, L.S.H. et al., "Genomic Cloning of 18kda Oleosin and Detection of Traicymglycerol and Oleosin Isoforms in Maturing Rice Postgermination Seeds," *J. Biochem.* 123(3): 386-391, (1998).

Zheng, Z. et al., "5' Distal and Proximal Cis-Acting Regulatory Elements are Required for Developmental Control of a Rice Seed Storage Protein Gene," *Plant J.* (4) 357-366 (1993).

\* cited by examiner

Hydrophobic oil body anchor

```
                                        KNOT
1   M-DLINSVLNLVVPPASLL--MLAFAWPTLSFINACEWLYNTYE--SEEMDNKVVVITGASS        CcSTO-1
1   M-DLINSLLNEVVPPASLL--MLAFTMPTLEFITTCEWLYNTYLNSENMENKVVLITGASS        SiSTO-B
1   MVDLINSVMNLVAPPATMVM-AFAWPILSFISFSERAYNSYFATENMEDKVVVITGASS          AtSTOLE-7

58  GIGEQIAYEYAKRGANLVLVARRDNRLHGIADNAQRLGSRHVLIMAADVVKEEDCRRFIN         CcSTO-1
59  GIGEQIAYQYAKRGANLVLVARREHRLRGISFNARRLGAPNVLIMAADVVKEEECRRFIN        SiSTO-B
60  AIGEQIAYEYAKRGANLVLVARREQRLRVVSNKAKQIGANHVILIAADVTKEDDCRRFIT        AtSTOLE-7
                                                          NADPH binding region 118 ETINYFGCVDHLVNTASLGHTFEFEEATDASVFPILLDINFWGNVYPTYVALPYLRQTNG        CcSTO-1
119 ETINYYGRVDHLVNTVSLGHTFYFEEASDSSVFPILMDINFWGNVYPTYVALPYLRESNG        SiSTO-B
120 QAVNYYGRVDHLVNTASLGHTFYFEEVSDTTVFPHLLDINFWGNVYPTYVALPYLHQTNG        AtSTOLE-7
                                  Active Site        Sterol binding region 178 RIVVNASIENWLPLPRMSLYSAAKAALINFYETLRFEVKDEVGITIATHGWIGTEMTRGR        CcSTO-1
179 RIVNASVENWLPLPRMSLYSAAKSALINFYETLRFEVKNEVGITVATHGWIGTEMTRGK          SiSTO-B
180 RIVVNASVENWLPLPRMSLYSAAKAALINFYETLRFELNGDVGITIATHGWIGSEMSGGK        AtSTOLE-7

238 FMVEEGAEMQWKEEREVQVTGGPAEDFAKLIVAGACRQAAYVKYPSWYDIFFVERVFSPN        CcSTO-1
239 FMVEEGAEMQWKEEREVHVTGGPIVEEFAKQIVSGACRGDPYVKYPSWYDIEFLYRVFAPK       SiSTO-B
240 FMIEEGAEMQWKEEREVPANGGPLEEFAKMIVAGACRGDAYVKFPNWYDVELLYRVETPN        AtSTOLE-7

298 VLYWTFHLLISHVSRRTSFIGTG--RP------L--LEGSPPRK--LL----              CcSTO-1
299 VLDWTFRFLLTNGGARRTSFIGTG--RP------L--LETSSPRRSAVME--              SiSTO-B
300 VLRWTFKLLISTEGTRRSSLVGSGMPVDESSSQMKLMLEGGPPRVPASPPRYTASPPH        AtSTOLE-7

335 -GASPGTSSQSQ---A--PVYQQ---QKV--E                 CcSTO-1
338 -GSSPRRLPGPLTF--S--PAFQQ---QKIS-E                SiSTO-B
360 YTASPPRVEASPPRYPASPPRESQFNIQ---EL                AtSTOLE-7
```

FIG. 2

AGCAAACATCTTTATTTTTAATTTATTGATGTTTTCTTACATCTTTTAATTTTATTTTTGTCCATTAAATTA

AAAAAGTTAAAAAAGAATTATTTTTCTTTAACCCAAATTATTTAATGCCACAACCACTTACTTTTATCTCTT

TTTTTTTGTTTCTTATCAAGTTTGCATTTCTATTTTCGATTCTCTTGACTTCTTTCGAACCCCAAACTTTCT

TTTTTAAATTGCAATCTCTAAATCCCAAA<u>ACGT</u>AAATTAAAATTTAAGTTCACAATGTCTAAATTCTCATAG

<u>ACGT</u>GAATTTTGTATAATTTCAAAATATTGTGATATTTTTGGGTTGGATTTAAGATTTTTTGGTAGATATAA

TTGAAATTGAAATGAAATTTATTTGTTTTAACTTATAATTCAAAAAATTTATTTTTAAAAATCCAAGTTATT

CAAAAATAGTAAACTTTTCATCATGTAAAGTATTAAATTAGTCTATTACATGTCTTATTTTGTGCATATATA

TATTTATATAAATTATTTTTAAAAATTTATTGAACCGAAGTTGAACTGATCCGACCGGTTGAATCTCGACC

CTTTCACTTCACCGGTTCAATTAACAGTCCGGTTTTTAAAATATTCTTATAGACGGGACTGCCATGGTGCCA

AACTTGTACTAGAGAAAAATATGATTTAAGTCCAACATGATTAATCCAAATTCAATTAGCCAATGGTTTCTT

TAAATTAAGAAAAGTAACAAATGATTGAAAAAAAAAAAACCAATGGGTTAAGTTAAAGAACATAAGTGCCCA

TTAAATCCAATAAATATATAAACTAGAAAAAGCATCATCAATAGATGCTAACAAAATTGTGAAGTCATCATC

ATTACCAAACACCAAATTTTC[CATGCAAAA]CTACTCTCCCTTTCTCAAACATGTGTCACCACCTTAACTCTA

CGTGTCCATTCCCCCTTCCC<u>TTTAAAT</u>CCAGCACCTCACCACGACCGCCACCGCGCCATTTTCACCATCTTT

AGCACTCAAAAAGGGGAAAGCAAAAAACTCCGATTTTTTTCCCATAAGCTACCGTCCACCGCCCTTC[ATGGC]
                                                                             [HindIII]    M  A
TGAGCACTACCAGCTGCAGCAACGCCCCACAGAGGCCGTCAAAAGCTTCCTTCCTCAGAAGGGTCCATCAAC
 E  H  Y  Q  L  Q  Q  R  P  T  E  A  V  K  S  F  L  P  Q  K  G  P  S  T
TTCACATGTGTTAGCAGTTGTCACGCTCCTCCCAGTTGCGGGAGTCCTGCTAGGCCTTTCTGGGCTGATTCT
  S  H  V  L  A  V  V  T  L  L  P  V  A  G  V  L  L  G  L  S  G  L  I  L
CGTCGGAACGGTCATCGGTCTGGCGGTGACAACCCCGCTTTTCGTTATCTTTAGCCCCATTTTGGTCCCAGC
 V  G  T  V  I  G  L  A  V  T  T  P  L  F  V  I  F  S  P  I  L  V  P  A
TGTATTTACCCTAGGGCTGACCCTGGCCGGGTTCTTGACCTCCGGTGCTTTCGGGATCACTGCACTTGCTTC
 V  F  T  L  G  L  T  L  A  G  F  L  T  S  G  A  F  G  I  T  A  L  A  S
ATTGTCGTGGATGCTGAACTACATCCGACTCATGAAGGCGTCTTCCCAGGAGCAAATGGACCTCGCAAAGTG
 L  S  W  M  L  N  Y  I  R  L  M  K  A  S  S  Q  E  Q  M  D  L  A  K  W
GCGCGTGCAGGACACTGCCGGCCAAGTTGGTCAGAAAGCGAGAGACGTGGGCCAGAGAACTCAAGATGTAGC
 R  V  Q  D  T  A  G  Q  V  G  Q  K  A  R  D  V  G  Q  R  T  Q  D  V  A
CAGAGCA[TGA]GCTCCTGAAGTGGGCTTTGTGTCACGAGCTCGGCCCAATTTTGTATTGGGTTTTGATGTTCG
 R  A  *
TTTTGTTTCTGATCCTTGTTAATCTTGCCTATGGCTTTTATATTTCTCCCTTTTTTTTTTTCTCTTTTTTTT

TCTAGATTAACAAGGGTGAATAAATGCAACTCACATAATTTGGAATAAAAAAAAAAAAA

```
  1 MADHQA-SPGQPQ--WP------PRP-TTT-STAGATTLFLRKMHEHAPN-STQLGFLL      CcOLE-5
  1 MAERF---SSGEAQYWPNYGST-A-----TTTVSNSPISSEHQL-RSHSPL-SSQLFGFLA    AtSM2
  1 MADRTNPSSHTQQR-PIYNSTTVPRSNTTT-NHE-LSSLLRQLLQSQSPNHSGQLFGFLA    AtSM1

48 LMISGGI-LLLLTGLTLTAATVLGLIEFAPLIIISSPIWVPAGSILFVLIAGLI--SFFGF    CcOLE-5
 51 LFISGI--LLFLLGVSVTAAVLGFIVFLPLIIISSPIWIP----V--FVVGGFI---GF     AtSM2
 57 FFISGGI-LLLLTGITVTAFVLGFIAFLPLIIISSPIWIE------LFIIVTGFI-SLAG-   AtSM1

105 -GVAAMAAESWLYRYFRGEHPPGSDRVDYARSRIANTASQVKDYAREYGYL-HGKVKDAAPGA CcOLE-5
104 L--VGTVALVSWTYRYFRGMHPVGSNQMDYARSRIYDTASHVKDYAREYGYF-HGRAKDAAPGA AtSM2
110 LIIATGAVSWLYRYFKGMHPLRSDQVDYARSRIHDTAAHVKDYA---GGYF-HGTLKDAAPGA AtSM1
```

FIG. 9E

SEQUENCE LISTING

```
<160> NUMBER OF SEQ ID NOS: 84

<210> SEQ ID NO 1
<211> LENGTH: 447
<212> TYPE: DNA
<213> ORGANISM: Coffea arabica

<400> SEQUENCE: 1
atggctgagc actaccagct gcagcaacgc cccacagagg ccgtcaaaag cttccttcct      60
cagaagggtc catcaacttc acatgtgtta gcagttgtca cgctcctccc agttgcggga     120
gtcctgctag gcctttccgg gctgattctc gtcggaacgg tcatcggtct ggcggtgaca     180
accccgcttt tcgttatctt tagccccatt ttggtcccag ctgtatttgc cctagggctg     240
gccctggccg ggttcttgac ctccggtgct ttcgggatca ctgcacttgc ttcattgtcg     300
tggatgctga actacatccg actcatgaag gcgtcttccc aggagcaaat ggacctcgca     360 aagtgcgcg tgcaggacac tgccggccaa gttggtcaga aagcgagaga cgtgggccag     420
agaactcaag atgtagccag agcatga                                         447

<210> SEQ ID NO 2
<211> LENGTH: 629
<212> TYPE: DNA
<213> ORGANISM: Coffea canephora (robusta)

<400> SEQUENCE: 2
ggaccatctt tagcactcaa aaagggggaaa gcaaaaaact ccgatttttt tcccataagc     60
taccgtccac cgcccttcat ggctgagcac taccagctgc agcaacgccc cacagaggcc    120
gtcaaaagct ccttcctca gaagggtcca tcaacttcac atgtgttagc agttgtcacg    180
ctcctcccag ttgcgggagt cctgctaggc ctttctgggc tgattctcgt cggaacggtc    240
atcggtctgg cggtgacaac cccgcttttc gttatcttta gcccatttt ggtcccagct    300
```

-continued

```
gtatttaccc tagggctgac cctggccggg ttcttgacct ccggtgcttt cgggatcact    360
gcacttgctt cattgtcgtg gatgctgaac tacatccgac tcatgaaggc gtcttcccag    420
gagcaaatgg acctcgcaaa gtggcgcgtg caggacactg ccggccaagt tggtcagaaa    480
gcgagagacg tgggccagag aactcaagat gtagccagag catgagctcc tgaagtgggc    540
tttgtgtcac gagctcggcc caattttgta ttgggttttg atgttcgttt tgtttctgat    600
ccttgttaat cttgcctatg ctttttata                                     629
```

```
<210> SEQ ID NO 3
<211> LENGTH: 558
<212> TYPE: DNA
<213> ORGANISM: Coffea canephora (robusta)

<400> SEQUENCE: 3
```

```
tgcagaattc ggtaccacaa caaaaacttc aattcccacc atccgcttgt cccttcgcct     60
taggaatcct cctcctcttc ctcctcatgg cggacattcg tcagcagcag ccgctatccc    120
accaggtggt caaggcggcc accgcggtga cggctggtgg gtcgcttctg gttctttcgg    180
gcctgatcct agcagggact gtgattgcac tagctctggc cacgcctttg ctggtgattt    240
tcagcccggt gctggtcccc gcggggatca cggtgtttct gctggtcacc gggttcctgt    300 cttcggagg gtttggggtg gcagcgttga gcgtgctgtc ctggatttac gggtacgtga    360
cggggaagaa cccgccggga gcggaccagc tggaccgggc aaggcaaaag ctggctctta    420
aggctaggga gatgaaggac agggctgagc agtatgggca gcagaacata cccgccggtt    480
cccagcagca ctagatttga aatttaagcc aatgatcagc tccaattcca gtggtgtgga    540
taggtggaat tgtcatgt                                                 558
```

```
<210> SEQ ID NO 4
<211> LENGTH: 707
<212> TYPE: DNA
<213> ORGANISM: Coffea canephora (robusta)

<400> SEQUENCE: 4
```

```
cctcttatca tcattaaaaa aaaccaaaaa aaaaagctca acaatctagt cattcagagc     60
aatcgatggc tgatcgagac cgttcaccgc cacaacagct tcaagtacac catcagcacc    120
tgggatatgg ggaaggcggt gtcaagaccc tctttcctca gacgggcccg tcggcaattc    180
aagtcctggc agttgtcact ctcctccctg ttggtggcac cctctttggt ctcgctggtc    240
tcacattagt tgggaccttg atcggccttg ccctcaccac cccactcttt gtgatctgca    300
gcccggttct ggtgcctgct gttgtcctct tcggcctggc cgtcactggc ttcctctcgt    360
ctggagcctt cggtctcatg gggctctcat ctctttcttg ggttttgaat tgcttcaggc    420
agaaggctac ggagcagatg gacgatgcca ggaggcgcat gcaggaggcg cagggcaac    480 tgggccagaa gactaaggaa gtaggggaga ggatccagac aaaagcccag gaacctactg    540
gaagagatca aggtgtaagg gaagctggaa aatacgtgga gaaattccaa taaagcactg    600
agccagtatg cagcatgcaa gttggttcct ggaaataatg tagatgtttg taattgtact    660
gtgatgttat taattgtacc gtgtcaattc gtatttggtt gtattat                 707
```

```
<210> SEQ ID NO 5
<211> LENGTH: 720
<212> TYPE: DNA
<213> ORGANISM: Coffea canephora (robusta)

<400> SEQUENCE: 5
```

```
atcccaattc ccaactccat ttccatccat tgtgctgaaa atcccaacaa aaaattgaag      60 gaaaaaaaa gaaatggcaa ccctccctga ccagccgcag acacagcact caactagtca     120
ggtggtaaaa accaccacag cagtcgccgt gggggttca ctcatgcttc tgtcggggct     180
gacactggct ggaacaataa taggcctagt tttggcaacg cccctttgg tgattttcag     240 tcctgtgata gtcccagctg ctgtaacctt ctttctgatt cttgcagggt tctttatctc     300
tggaggtctt ggcgtaactg ccacctttat tttctactgg atgttcaggt atgcgactgg     360
gaagcacccc atcggggcag atcagctgga tcgtgcgaga gaaaagattg ctcatgcagc     420
taaggagatg agggacaaag ctgaacattt tgggcagcag gctcagcagc agattaaagg     480
ttccccagat caagatactt gatggaatgt tgtgcatgca attaatgtat gatgatgcat     540
gaataaactc tgtgctttaa ttagccggga ttgtgacttt gtatgtttcc tagttaatcg     600
gcaattcaat tgttgttgtg actgttgtag agagtggaga tgagttgctg tttctctcaa     660
ctcagcttgt tctgcgagtt tgtcgttgga tacgtcgttt catgtgtgct aatacatttg     720

<210> SEQ ID NO 6
<211> LENGTH: 620
<212> TYPE: DNA
<213> ORGANISM: Coffea canephora (robusta)

<400> SEQUENCE: 6
ctcttctcca aacaactcca gctttccaac catggccgac caccaagcca gccctggcca      60
accccaatgg ccaccgcgcc caaccaccac ctccactgcc ggcgccacta ccttatttct     120
acgtaaaatg catgagcatg cacccaactc aacccagctc atcgggttct tgaccttggt     180
aatatccggt ggcatcctac ttctcctcac tggcctaact ctcaccgcca cggttctcgg     240
cctaattttc ttcgctccct tgattataat ctccagcccc atttgggttc cggctggatc     300
aattctcttc gtgatcatcg ccggattgct ctctttcttc gggttcggtg tcgcagccat     360
ggcggctttt tcttggctgt acaggtactt tcggggcttc caccccgcccg gttcggaccg     420 ggttgactat gcaagaagcc gaattgcgaa tacggcaagt caggtgaagg attatgctag     480
agagtacggt ggatatttgc acggtaaagt gaaggatgca gctcctggtg cttgaaaaaa     540 ttttttttatt acagatgttt ttcggcaagc ttgttctgtt cttttaattat taatgagatg     600 tcatatatat atatatatat                                                620

<210> SEQ ID NO 7
<211> LENGTH: 1224
<212> TYPE: DNA
<213> ORGANISM: Coffea canephora (robusta)

<400> SEQUENCE: 7
caaaaaataa aagtaaaaaa aaaagaattt tttctttttt taagctagct agttcttggt      60
agatatggat ttgataaact ccgtcttgaa tttggtggtg ccacctgcaa gtttacttat     120
gcttgccttt gcatggccaa ctttgtcatt catcaatgct tgtgaatggc tgtacaatac     180
ttacttcagt gaagagatgg acaacaaagt ggttgtcatc accggagctt cttctgggat     240
tggagaacaa attgcctatg aatatgcaaa aaggggtgcc aatcttgtac tggtggcacg     300
aagagacaac aggctccatg gcatagctga taacgctcaa cgtttgggct caaggcatgt     360
gttgataatg gctgcagatg ttgtcaagga agaagattgt agaagattca tcaatgaaac     420
tatcaactac tttgggtgtg tggaccatct agtaaacaca gctagcttgg ggcatacttt     480
ctttttcgag gaagctacag atgcatcagt atttccgatt ttattggaca taaacttttg     540
```

```
ggggaatgtg tatccaacct atgtggctct gccttatctc cggcaaacta atggtcgaat    600
cgttgtgaat gcttcaattg aaaattggtt acctttgccg agaatgagct tatattctgc    660
ggccaaagct gcacttataa acttctatga acccctgaga tttgaagtga aggatgaagt    720
cggcataaca atcgcaaccc atggttggat agggactgaa atgacccgtg aagattcat    780 ggttgaagaa ggtgcagaga tgcaatggaa agaagaaaga gaagttcaag tgactggtgg    840
tcccgcagag gattttgcaa agttgatcgt ggctggggct tgccgacaag ctgcatatgt    900 aaaataccc agctggtacg acatattctt tgttttcagg gtcttttctc ctaatgtcct    960
gtactggacc tttcacttgc tctccacaag tcatgtttca agaagaactt ctttcatcgg    1020
cactggaagg cctcttttgg agggctcccc tccgaggaaa cttctcactg gtgcaagtcc    1080
tggtacctcc tctcagtctc aagcacccgt ttaccagcag cagaaagtgg aatgaaaggg    1140
ttatagtcat gatcattatt atttaccggt tttgatgttt actttgttgt cttgtgatac    1200
tctggagaaa tttgtctgag acaa    1224

<210> SEQ ID NO 8
<211> LENGTH: 148
<212> TYPE: PRT
<213> ORGANISM: Coffea arabica

<400> SEQUENCE: 8

Met Ala Glu His Tyr Gln Leu Gln Gln Arg Pro Thr Glu Ala Val Lys
1               5                   10                  15

Ser Phe Leu Pro Gln Lys Gly Pro Ser Thr Ser His Val Leu Ala Val
            20                  25                  30

Val Thr Leu Leu Pro Val Ala Gly Val Leu Leu Gly Leu Ser Gly Leu
        35                  40                  45

Ile Leu Val Gly Thr Val Ile Gly Leu Ala Val Thr Thr Pro Leu Phe
    50                  55                  60

Val Ile Phe Ser Pro Ile Leu Val Pro Ala Val Phe Ala Leu Gly Leu
65                  70                  75                  80

Ala Leu Ala Gly Phe Leu Thr Ser Gly Ala Phe Gly Ile Thr Ala Leu
                85                  90                  95

Ala Ser Leu Ser Trp Met Leu Asn Tyr Ile Arg Leu Met Lys Ala Ser
            100                 105                 110

Ser Gln Glu Gln Met Asp Leu Ala Lys Trp Arg Val Gln Asp Thr Ala
        115                 120                 125

Gly Gln Val Gly Gln Lys Ala Arg Asp Val Gly Gln Arg Thr Gln Asp
    130                 135                 140

Val Ala Arg Ala
145

<210> SEQ ID NO 9
<211> LENGTH: 148
<212> TYPE: PRT
<213> ORGANISM: Coffea canephora (robusta)

<400> SEQUENCE: 9

Met Ala Glu His Tyr Gln Leu Gln Gln Arg Pro Thr Glu Ala Val Lys
1               5                   10                  15

Ser Phe Leu Pro Gln Lys Gly Pro Ser Thr Ser His Val Leu Ala Val
            20                  25                  30

Val Thr Leu Leu Pro Val Ala Gly Val Leu Leu Gly Leu Ser Gly Leu
        35                  40                  45
```

```
Ile Leu Val Gly Thr Val Ile Gly Leu Ala Val Thr Thr Pro Leu Phe
 50                  55                  60

Val Ile Phe Ser Pro Ile Leu Val Pro Ala Val Phe Thr Leu Gly Leu
 65                  70                  75                  80

Thr Leu Ala Gly Phe Leu Thr Ser Gly Ala Phe Gly Ile Thr Ala Leu
                 85                  90                  95

Ala Ser Leu Ser Trp Met Leu Asn Tyr Ile Arg Leu Met Lys Ala Ser
            100                 105                 110

Ser Gln Glu Gln Met Asp Leu Ala Lys Trp Arg Val Gln Asp Thr Ala
        115                 120                 125

Gly Gln Val Gly Gln Lys Ala Arg Asp Val Gly Gln Arg Thr Gln Asp
    130                 135                 140

Val Ala Arg Ala
145

<210> SEQ ID NO 10
<211> LENGTH: 135
<212> TYPE: PRT
<213> ORGANISM: Coffea canephora (robusta)

<400> SEQUENCE: 10

Met Ala Asp Ile Arg Gln Gln Pro Leu Ser His Gln Val Val Lys
1               5                   10                  15

Ala Ala Thr Ala Val Thr Ala Gly Gly Ser Leu Leu Val Leu Ser Gly
                 20                  25                  30

Leu Ile Leu Ala Gly Thr Val Ile Ala Leu Ala Leu Thr Pro Leu
             35                  40                  45

Leu Val Ile Phe Ser Pro Val Leu Val Pro Ala Gly Ile Thr Val Phe
 50                  55                  60

Leu Leu Val Thr Gly Phe Leu Ser Ser Gly Phe Gly Val Ala Ala
 65                  70                  75                  80

Leu Ser Val Leu Ser Trp Ile Tyr Gly Tyr Val Thr Gly Lys Asn Pro
                 85                  90                  95

Pro Gly Ala Asp Gln Leu Asp Arg Ala Arg Gln Lys Leu Ala Leu Lys
            100                 105                 110

Ala Arg Glu Met Lys Asp Arg Ala Glu Gln Tyr Gly Gln Gln Asn Ile
        115                 120                 125

Pro Ala Gly Ser Gln Gln His
    130                 135

<210> SEQ ID NO 11
<211> LENGTH: 175
<212> TYPE: PRT
<213> ORGANISM: Coffea canephora (robusta)

<400> SEQUENCE: 11

Met Ala Asp Arg Asp Arg Ser Pro Pro Gln Gln Leu Gln Val His His
1               5                   10                  15

Gln His Leu Gly Tyr Gly Glu Gly Gly Val Lys Thr Leu Phe Pro Gln
                 20                  25                  30

Thr Gly Pro Ser Ala Ile Gln Val Leu Ala Val Val Thr Leu Leu Pro
             35                  40                  45

Val Gly Gly Thr Leu Phe Gly Leu Ala Gly Leu Thr Leu Val Gly Thr
 50                  55                  60

Leu Ile Gly Leu Ala Leu Thr Thr Pro Leu Phe Val Ile Cys Ser Pro
 65                  70                  75                  80

Val Leu Val Pro Ala Val Val Leu Phe Gly Leu Ala Val Thr Gly Phe
```

```
              85                  90                  95
Leu Ser Ser Gly Ala Phe Gly Leu Met Gly Leu Ser Leu Ser Trp
            100                 105                 110

Val Leu Asn Cys Phe Arg Gln Lys Ala Thr Glu Gln Met Asp Asp Ala
            115                 120                 125

Arg Arg Arg Met Gln Glu Ala Ala Gly Gln Leu Gly Gln Lys Thr Lys
            130                 135                 140

Glu Val Gly Glu Arg Ile Gln Thr Lys Ala Gln Glu Pro Thr Gly Arg
145                 150                 155                 160

Asp Gln Gly Val Arg Glu Ala Gly Lys Tyr Val Glu Lys Phe Gln
                165                 170                 175

<210> SEQ ID NO 12
<211> LENGTH: 142
<212> TYPE: PRT
<213> ORGANISM: Coffea canephora (robusta)

<400> SEQUENCE: 12

Met Ala Thr Leu Pro Asp Gln Pro Gln Thr Gln His Ser Thr Ser Gln
1               5                   10                  15

Val Val Lys Thr Thr Thr Ala Val Ala Val Gly Gly Ser Leu Met Leu
                20                  25                  30

Leu Ser Gly Leu Thr Leu Ala Gly Thr Ile Ile Gly Leu Val Leu Ala
            35                  40                  45

Thr Pro Leu Leu Val Ile Phe Ser Pro Val Ile Val Pro Ala Ala Val
        50                  55                  60

Thr Phe Phe Leu Ile Leu Ala Gly Phe Phe Ile Ser Gly Gly Leu Gly
65                  70                  75                  80

Val Thr Ala Thr Phe Ile Phe Tyr Trp Met Phe Arg Tyr Ala Thr Gly
                85                  90                  95

Lys His Pro Ile Gly Ala Asp Gln Leu Asp Arg Ala Arg Glu Lys Ile
            100                 105                 110

Ala His Ala Ala Lys Glu Met Arg Asp Lys Ala Glu His Phe Gly Gln
        115                 120                 125

Gln Ala Gln Gln Gln Ile Lys Gly Ser Pro Asp Gln Asp Thr
    130                 135                 140

<210> SEQ ID NO 13
<211> LENGTH: 167
<212> TYPE: PRT
<213> ORGANISM: Coffea canephora (robusta)

<400> SEQUENCE: 13

Met Ala Asp His Gln Ala Ser Pro Gly Gln Pro Gln Trp Pro Pro Arg
1               5                   10                  15

Pro Thr Thr Thr Ser Thr Ala Gly Ala Thr Thr Leu Phe Leu Arg Lys
                20                  25                  30

Met His Glu His Ala Pro Asn Ser Thr Gln Leu Ile Gly Phe Leu Thr
            35                  40                  45

Leu Val Ile Ser Gly Gly Ile Leu Leu Leu Thr Gly Leu Thr Leu
        50                  55                  60

Thr Ala Thr Val Leu Gly Leu Ile Phe Phe Ala Pro Leu Ile Ile Ile
65                  70                  75                  80

Ser Ser Pro Ile Trp Val Pro Ala Gly Ser Ile Leu Phe Val Ile Ile
                85                  90                  95

Ala Gly Leu Leu Ser Phe Phe Gly Phe Gly Val Ala Ala Met Ala Ala
            100                 105                 110
```

Phe Ser Trp Leu Tyr Arg Tyr Phe Arg Gly Phe His Pro Pro Gly Ser
        115                 120                 125

Asp Arg Val Asp Tyr Ala Arg Ser Arg Ile Ala Asn Thr Ala Ser Gln
130                 135                 140

Val Lys Asp Tyr Ala Arg Glu Tyr Gly Gly Tyr Leu His Gly Lys Val
145                 150                 155                 160

Lys Asp Ala Ala Pro Gly Ala
                165

<210> SEQ ID NO 14
<211> LENGTH: 356
<212> TYPE: PRT
<213> ORGANISM: Coffea canephora (robusta)

<400> SEQUENCE: 14

Met Asp Leu Ile Asn Ser Val Leu Asn Leu Val Val Pro Pro Ala Ser
1               5                   10                  15

Leu Leu Met Leu Ala Phe Ala Trp Pro Thr Leu Ser Phe Ile Asn Ala
            20                  25                  30

Cys Glu Trp Leu Tyr Asn Thr Tyr Phe Ser Glu Glu Met Asp Asn Lys
        35                  40                  45

Val Val Val Ile Thr Gly Ala Ser Ser Gly Ile Gly Glu Gln Ile Ala
    50                  55                  60

Tyr Glu Tyr Ala Lys Arg Gly Ala Asn Leu Val Leu Val Ala Arg Arg
65                  70                  75                  80

Asp Asn Arg Leu His Gly Ile Ala Asp Asn Ala Gln Arg Leu Gly Ser
                85                  90                  95

Arg His Val Leu Ile Met Ala Ala Asp Val Val Lys Glu Glu Asp Cys
            100                 105                 110

Arg Arg Phe Ile Asn Glu Thr Ile Asn Tyr Phe Gly Cys Val Asp His
        115                 120                 125

Leu Val Asn Thr Ala Ser Leu Gly His Thr Phe Phe Phe Glu Glu Ala
    130                 135                 140

Thr Asp Ala Ser Val Phe Pro Ile Leu Leu Asp Ile Asn Phe Trp Gly
145                 150                 155                 160

Asn Val Tyr Pro Thr Tyr Val Ala Leu Pro Tyr Leu Arg Gln Thr Asn
                165                 170                 175

Gly Arg Ile Val Val Asn Ala Ser Ile Glu Asn Trp Leu Pro Leu Pro
            180                 185                 190

Arg Met Ser Leu Tyr Ser Ala Ala Lys Ala Ala Leu Ile Asn Phe Tyr
        195                 200                 205

Glu Thr Leu Arg Phe Glu Val Lys Asp Glu Val Gly Ile Thr Ile Ala
    210                 215                 220

Thr His Gly Trp Ile Gly Thr Glu Met Thr Arg Gly Arg Phe Met Val
225                 230                 235                 240

Glu Glu Gly Ala Glu Met Gln Trp Lys Glu Arg Glu Val Gln Val
                245                 250                 255

Thr Gly Gly Pro Ala Glu Asp Phe Ala Lys Leu Ile Val Ala Gly Ala
            260                 265                 270

Cys Arg Gln Ala Ala Tyr Val Lys Tyr Pro Ser Trp Tyr Asp Ile Phe
        275                 280                 285

Phe Val Phe Arg Val Phe Ser Pro Asn Val Leu Tyr Trp Thr Phe His
    290                 295                 300

Leu Leu Ser Thr Ser His Val Ser Arg Arg Thr Ser Phe Ile Gly Thr
305                 310                 315                 320

Gly Arg Pro Leu Leu Glu Gly Ser Pro Pro Arg Lys Leu Leu Thr Gly
            325                 330                 335

Ala Ser Pro Gly Thr Ser Ser Gln Ser Gln Ala Pro Val Tyr Gln Gln
            340                 345                 350

Gln Lys Val Glu
        355

<210> SEQ ID NO 15
<211> LENGTH: 1002
<212> TYPE: DNA
<213> ORGANISM: Coffea canephora (robusta)

<400> SEQUENCE: 15

```
agcaaacatc tttattttta atttattgat gttttcttac atctttaat tttattttg      60
tccattaaat taaaaagtt aaaaagaat tattttctt taacccaat tatttaatgc     120
cacaaccact tacttttatc tctttttttt tgtttcttat caagtttgca tttctatttt    180
cgattctctt gacttctttc gaaccccaaa ctttcttttt taaattgcaa tctctaaatc    240
ccaaaacgta aattaaaatt taagttcaca atgtctaaat tctcatagac gtgaattttg    300
tataatttca aaatattgtg atattttgg gttggattta agattttg gtagatataa       360
ttgaaattga aatgaaattt atttgtttta acttataatt caaaaatttt atttttaaaa   420
atccaagtta ttcaaaaata gtaaactttt catcatgtaa agtattaaat tagtctatta   480
catgtcttat tttgtgcata tatatttta taaaattat ttttaaaaa tttattgaac      540
cgaagttgaa ctgatccgac cggttgaatc tcgaccctt cacttcaccg gttcaattaa    600
cagtccggtt tttaaaatat tcttatagac gggactgcca tggtgccaaa cttgtactag    660
agaaaaatat gatttaagtc caacatgatt aatccaaatt caattagcca atggtttctt   720
taaattaaga aaagtaacaa atgattgaaa aaaaaaaac caatgggtta agttaaagaa    780
cataagtgcc cattaaatcc aataaatata taaactagaa aaagcatcat caatagatgc   840
taacaaaatt gtgaagtcat catcattacc aaacaccaaa ttttccatgc aaaactactc   900
tccctttctc aaacatgtgt caccaccta actctacgtg tccattcccc cttccctta     960
aatccagcac ctcaccacga ccgccaccgc gccattttca cc                     1002
```

<210> SEQ ID NO 16
<211> LENGTH: 362
<212> TYPE: PRT
<213> ORGANISM: Sesamum indicum

<400> SEQUENCE: 16

Met Asp Leu Ile Asn Ser Leu Leu Asn Phe Val Val Pro Pro Ala Ser
1               5                   10                  15

Leu Leu Met Leu Ala Phe Thr Trp Pro Thr Leu Phe Phe Ile Thr Thr
            20                  25                  30

Cys Glu Trp Leu Tyr Asn Thr Tyr Leu Asn Ser Glu Asn Met Glu Asn
            35                  40                  45

Lys Val Val Leu Ile Thr Gly Ala Ser Ser Gly Ile Gly Glu Gln Ile
        50                  55                  60

Ala Tyr Gln Tyr Ala Lys Arg Gly Ala Asn Leu Val Leu Val Ala Arg
65                  70                  75                  80

Arg Glu His Arg Leu Arg Gly Ile Ser Glu Asn Ala Arg Arg Leu Gly
                85                  90                  95

Ala Pro Asn Val Leu Ile Met Ala Ala Asp Val Val Lys Glu Glu Glu
            100                 105                 110

```
Cys Arg Arg Phe Ile Asn Glu Thr Ile Asn Tyr Tyr Gly Arg Val Asp
            115                 120                 125

His Leu Val Asn Thr Val Ser Leu Gly His Thr Phe Tyr Phe Glu Glu
        130                 135                 140

Ala Ser Asp Ser Ser Val Phe Pro Ile Leu Met Asp Ile Asn Phe Trp
145                 150                 155                 160

Gly Asn Val Tyr Pro Thr Tyr Val Ala Leu Pro Tyr Leu Arg Glu Ser
                165                 170                 175

Asn Gly Arg Ile Ile Val Asn Ala Ser Val Glu Asn Trp Leu Pro Leu
            180                 185                 190

Pro Arg Met Ser Leu Tyr Ser Ala Ala Lys Ser Ala Leu Ile Asn Phe
        195                 200                 205

Tyr Glu Thr Leu Arg Phe Glu Val Lys Asn Glu Val Gly Ile Thr Val
210                 215                 220

Ala Thr His Gly Trp Ile Gly Thr Glu Met Thr Arg Gly Lys Phe Met
225                 230                 235                 240

Val Glu Glu Gly Ala Glu Met Gln Trp Lys Glu Glu Arg Glu Val His
                245                 250                 255

Val Thr Gly Gly Pro Val Glu Glu Phe Ala Lys Gln Ile Val Ser Gly
            260                 265                 270

Ala Cys Arg Gly Asp Pro Tyr Val Lys Tyr Pro Ser Trp Tyr Asp Ile
        275                 280                 285

Phe Phe Leu Tyr Arg Val Phe Ala Pro Lys Val Leu Asp Trp Thr Phe
290                 295                 300

Arg Phe Leu Leu Thr Asn Gly Gly Ala Arg Arg Thr Ser Phe Ile Gly
305                 310                 315                 320

Thr Gly Arg Pro Leu Leu Glu Thr Ser Ser Pro Arg Arg Ser Ala Val
                325                 330                 335

Met Glu Gly Ser Ser Pro Arg Arg Leu Pro Pro Gly Pro Leu Thr Phe
            340                 345                 350

Ser Pro Ala Phe Gln Gln Gln Lys Ser Glu
        355                 360

<210> SEQ ID NO 17
<211> LENGTH: 389
<212> TYPE: PRT
<213> ORGANISM: Arabidopsis thaliana

<400> SEQUENCE: 17

Met Val Asp Leu Leu Asn Ser Val Met Asn Leu Val Ala Pro Pro Ala
1               5                   10                  15

Thr Met Val Val Met Ala Phe Ala Trp Pro Leu Leu Ser Phe Ile Ser
            20                  25                  30

Phe Ser Glu Arg Ala Tyr Asn Ser Tyr Phe Ala Thr Glu Asn Met Glu
        35                  40                  45

Asp Lys Val Val Val Ile Thr Gly Ala Ser Ser Ala Ile Gly Glu Gln
    50                  55                  60

Ile Ala Tyr Glu Tyr Ala Lys Arg Gly Ala Asn Leu Val Leu Val Ala
65                  70                  75                  80

Arg Arg Glu Gln Arg Leu Arg Val Val Ser Asn Lys Ala Lys Gln Ile
                85                  90                  95

Gly Ala Asn His Val Ile Ile Ile Ala Ala Asp Val Ile Lys Glu Asp
            100                 105                 110

Asp Cys Arg Arg Phe Ile Thr Gln Ala Val Asn Tyr Tyr Gly Arg Val
        115                 120                 125
```

```
Asp His Leu Val Asn Thr Ala Ser Leu Gly His Thr Phe Tyr Phe Glu
    130                 135                 140

Glu Val Ser Asp Thr Thr Val Phe Pro His Leu Leu Asp Ile Asn Phe
145                 150                 155                 160

Trp Gly Asn Val Tyr Pro Thr Tyr Val Ala Leu Pro Tyr Leu His Gln
                165                 170                 175

Thr Asn Gly Arg Ile Val Val Asn Ala Ser Val Glu Asn Trp Leu Pro
            180                 185                 190

Leu Pro Arg Met Ser Leu Tyr Ser Ala Ala Lys Ala Ala Leu Val Asn
        195                 200                 205

Phe Tyr Glu Thr Leu Arg Phe Glu Leu Asn Gly Asp Val Gly Ile Thr
    210                 215                 220

Ile Ala Thr His Gly Trp Ile Gly Ser Glu Met Ser Gly Gly Lys Phe
225                 230                 235                 240

Met Leu Glu Glu Gly Ala Glu Met Gln Trp Lys Glu Arg Glu Val
                245                 250                 255

Pro Ala Asn Gly Gly Pro Leu Glu Glu Phe Ala Lys Met Ile Val Ala
                260                 265                 270

Gly Ala Cys Arg Gly Asp Ala Tyr Val Lys Phe Pro Asn Trp Tyr Asp
            275                 280                 285

Val Phe Leu Leu Tyr Arg Val Phe Thr Pro Asn Val Leu Arg Trp Thr
    290                 295                 300

Phe Lys Leu Leu Leu Ser Thr Glu Gly Thr Arg Arg Ser Ser Leu Val
305                 310                 315                 320

Gly Val Gly Ser Gly Met Pro Val Asp Glu Ser Ser Gln Met Lys
                325                 330                 335

Leu Met Leu Glu Gly Gly Pro Pro Arg Val Pro Ala Ser Pro Pro Arg
            340                 345                 350

Tyr Thr Ala Ser Pro Pro His Tyr Thr Ala Ser Pro Pro Arg Tyr Pro
        355                 360                 365

Ala Ser Pro Pro Arg Tyr Pro Ala Ser Pro Pro Arg Phe Ser Gln Phe
    370                 375                 380

Asn Ile Gln Glu Leu
385
```

<210> SEQ ID NO 18
<211> LENGTH: 183
<212> TYPE: PRT
<213> ORGANISM: Arabidopsis thaliana

<400> SEQUENCE: 18

```
Met Ala Asp Val Arg Thr His Ser His Gln Leu Gln Val His Pro Gln
1               5                   10                  15

Arg Gln His Glu Gly Gly Ile Lys Val Leu Tyr Pro Gln Ser Gly Pro
            20                  25                  30

Ser Ser Thr Gln Val Leu Ala Val Phe Val Gly Val Pro Ile Gly Gly
        35                  40                  45

Thr Leu Leu Thr Ile Ala Gly Leu Thr Leu Ala Gly Ser Val Ile Gly
    50                  55                  60

Leu Met Leu Ala Phe Pro Leu Phe Leu Ile Phe Ser Pro Val Ile Val
65                  70                  75                  80

Pro Ala Ala Phe Val Ile Gly Leu Ala Met Thr Gly Phe Leu Ala Ser
                85                  90                  95

Gly Ala Ile Gly Leu Thr Gly Leu Ser Ser Met Ser Trp Val Leu Asn
            100                 105                 110
```

```
Tyr Ile Arg Arg Ala Gly Gln His Ile Pro Glu Glu Leu Glu Glu Ala
            115                 120                 125

Lys His Arg Leu Ala Asp Met Ala Glu Tyr Val Gly Gln Arg Thr Lys
            130                 135                 140

Asp Ala Gly Gln Thr Ile Glu Asp Lys Ala His Asp Val Arg Glu Ala
145                 150                 155                 160

Lys Thr Phe Asp Val Arg Asp Arg Asp Thr Thr Lys Gly Thr His Asn
                165                 170                 175

Val Arg Asp Thr Lys Thr Thr
            180

<210> SEQ ID NO 19
<211> LENGTH: 191
<212> TYPE: PRT
<213> ORGANISM: Arabidopsis thaliana

<400> SEQUENCE: 19

Met Ala Asn Val Asp Arg Asp Arg Arg Val His Val Asp Arg Thr Asp
1               5                   10                  15

Lys Arg Val His Gln Pro Asn Tyr Glu Asp Asp Val Gly Phe Gly Gly
            20                  25                  30

Tyr Gly Gly Tyr Gly Ala Gly Ser Asp Tyr Lys Ser Arg Gly Pro Ser
        35                  40                  45

Thr Asn Gln Ile Leu Ala Leu Ile Ala Gly Val Pro Ile Gly Gly Thr
50                  55                  60

Leu Leu Thr Leu Ala Gly Leu Thr Leu Ala Gly Ser Val Ile Gly Leu
65                  70                  75                  80

Leu Val Ser Ile Pro Leu Phe Leu Leu Phe Ser Pro Val Ile Val Pro
                85                  90                  95

Ala Ala Leu Thr Ile Gly Leu Ala Val Thr Gly Ile Leu Ala Ser Gly
            100                 105                 110

Leu Phe Gly Leu Thr Gly Leu Ser Ser Val Ser Trp Val Leu Asn Tyr
        115                 120                 125

Leu Arg Gly Thr Ser Asp Thr Val Pro Glu Gln Leu Asp Tyr Ala Lys
    130                 135                 140

Arg Arg Met Ala Asp Ala Val Gly Tyr Ala Gly Met Lys Gly Lys Glu
145                 150                 155                 160

Met Gly Gln Tyr Val Gln Asp Lys Ala His Glu Ala Arg Glu Thr Glu
                165                 170                 175

Phe Met Thr Glu Thr His Glu Pro Gly Lys Ala Arg Arg Gly Ser
            180                 185                 190

<210> SEQ ID NO 20
<211> LENGTH: 173
<212> TYPE: PRT
<213> ORGANISM: Arabidopsis thaliana

<400> SEQUENCE: 20

Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
50                  55                  60
```

Val Gly Thr Val Ile Ala Leu Thr Val Ala Thr Pro Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys Tyr Ala Thr Gly Glu His Pro Gln Gly Ser
        115                 120                 125

Asp Lys Leu Asp Ser Ala Arg Met Lys Leu Gly Ser Lys Ala Gln Asp
    130                 135                 140

Leu Lys Asp Arg Ala Gln Tyr Tyr Gly Gln Gln His Thr Gly Gly Glu
145                 150                 155                 160

His Asp Arg Asp Arg Thr Arg Gly Gly Gln His Thr Thr
                165                 170

<210> SEQ ID NO 21
<211> LENGTH: 199
<212> TYPE: PRT
<213> ORGANISM: Arabidopsis thaliana

<400> SEQUENCE: 21

Met Ala Asp Thr His Arg Val Asp Arg Thr Asp Arg His Phe Gln Phe
1               5                   10                  15

Gln Ser Pro Tyr Glu Gly Gly Arg Gly Gln Gly Gln Tyr Glu Gly Asp
                20                  25                  30

Arg Gly Tyr Gly Gly Gly Gly Tyr Lys Ser Met Met Pro Glu Ser Gly
            35                  40                  45

Pro Ser Ser Thr Gln Val Leu Ser Leu Leu Ile Gly Val Pro Val Val
    50                  55                  60

Gly Ser Leu Leu Ala Leu Ala Gly Leu Leu Leu Ala Gly Ser Val Ile
65                  70                  75                  80

Gly Leu Met Val Ala Leu Pro Leu Phe Leu Leu Phe Ser Pro Val Ile
                85                  90                  95

Val Pro Ala Ala Leu Thr Ile Gly Leu Ala Met Thr Gly Phe Leu Ala
            100                 105                 110

Ser Gly Met Phe Gly Leu Thr Gly Leu Ser Ser Ile Ser Trp Val Met
        115                 120                 125

Asn Tyr Leu Arg Gly Thr Arg Arg Thr Val Pro Glu Gln Leu Glu Tyr
    130                 135                 140

Ala Lys Arg Arg Met Ala Asp Ala Val Gly Tyr Ala Gly Gln Lys Gly
145                 150                 155                 160

Lys Glu Met Gly Gln His Val Gln Asn Lys Ala Gln Asp Val Lys Gln
                165                 170                 175

Tyr Asp Ile Ser Lys Pro His Asp Thr Thr Lys Gly His Glu Thr
            180                 185                 190

Gln Gly Arg Thr Thr Ala Ala
        195

<210> SEQ ID NO 22
<211> LENGTH: 141
<212> TYPE: PRT
<213> ORGANISM: Arabidopsis thaliana

<400> SEQUENCE: 22

Met Ala Asp Gln Thr Arg Thr His His Glu Met Ile Ser Arg Asp Ser
1               5                   10                  15

Thr Gln Glu Ala His Pro Lys Ala Arg Gln Met Val Lys Ala Ala Thr

```
            20                  25                  30
Ala Val Thr Ala Gly Gly Ser Leu Leu Val Leu Ser Gly Leu Thr Leu
        35                  40                  45

Ala Gly Thr Val Val Ala Leu Thr Val Ala Thr Pro Leu Leu Val Ile
    50                  55                  60

Phe Ser Pro Val Leu Val Pro Ala Val Val Thr Val Ala Leu Ile Ile
65                  70                  75                  80

Thr Gly Phe Leu Ala Ser Gly Gly Phe Gly Ile Ala Ala Ile Thr Ala
                85                  90                  95

Phe Ser Trp Leu Tyr Arg His Met Thr Gly Ser Gly Ser Asp Lys Ile
            100                 105                 110

Glu Asn Ala Arg Met Lys Val Gly Ser Arg Val Gln Asp Thr Lys Tyr
        115                 120                 125

Gly Gln His Asn Ile Gly Val Gln His Gln Gln Val Ser
    130                 135                 140

<210> SEQ ID NO 23
<211> LENGTH: 187
<212> TYPE: PRT
<213> ORGANISM: Zea mays

<400> SEQUENCE: 23

Met Ala Asp Arg Asp Arg Ser Gly Ile Tyr Gly Gly Ala His Ala Thr
1               5                   10                  15

Tyr Gly Gln Gln Gln Gln Gly Gly Gly Gly Arg Pro Met Gly Glu
            20                  25                  30

Gln Val Lys Lys Gly Met Leu His Asp Lys Gly Pro Thr Ala Ser Gln
        35                  40                  45

Ala Leu Thr Val Ala Thr Leu Phe Pro Leu Gly Leu Leu Leu Val
    50                  55                  60

Leu Ser Gly Leu Ala Leu Thr Ala Ser Val Val Gly Leu Ala Val Ala
65                  70                  75                  80

Thr Pro Val Phe Leu Ile Phe Ser Pro Val Leu Val Pro Ala Ala Leu
                85                  90                  95

Leu Ile Gly Thr Ala Val Met Gly Phe Leu Thr Ser Gly Ala Leu Gly
            100                 105                 110

Leu Gly Gly Leu Ser Ser Leu Thr Cys Leu Ala Asn Thr Ala Arg Gln
        115                 120                 125

Ala Phe Gln Arg Thr Pro Asp Tyr Val Glu Glu Ala Arg Arg Arg Met
    130                 135                 140

Ala Glu Ala Ala Ala Gln Ala Gly His Lys Thr Ala Gln Ala Gly Gln
145                 150                 155                 160

Ala Ile Gln Gly Arg Ala Gln Glu Ala Gly Thr Gly Gly Gly Ala Gly
                165                 170                 175

Ala Gly Ala Gly Gly Gly Gly Arg Ala Ser Ser
            180                 185

<210> SEQ ID NO 24
<211> LENGTH: 175
<212> TYPE: PRT
<213> ORGANISM: Zea mays

<400> SEQUENCE: 24

Met Ala Asp Arg Asp Arg Ser Gly Ile Tyr Gly Gly Gly Ala Tyr Gly
1               5                   10                  15

Gln Gln Gln Gly Arg Pro Pro Met Gly Glu Gln Val Lys Gly Met Ile
            20                  25                  30
```

```
His Asp Lys Gly Pro Thr Ala Ser Gln Ala Leu Thr Val Ala Thr Leu
            35                  40                  45

Phe Pro Leu Gly Gly Leu Leu Val Leu Ser Gly Leu Ala Leu Ala
 50                  55                  60

Ala Ser Thr Val Gly Leu Ala Val Ala Thr Pro Val Phe Leu Leu Phe
 65                  70                  75                  80

Ser Pro Val Leu Val Pro Ala Ala Leu Leu Ile Gly Thr Ala Val Ala
                 85                  90                  95

Gly Phe Leu Thr Ser Gly Ala Leu Gly Leu Gly Gly Leu Ser Ser Leu
                100                 105                 110

Thr Cys Leu Ala Asn Thr Ala Arg Gln Ala Phe Gln Arg Thr Pro Asp
            115                 120                 125

Tyr Val Glu Glu Ala Arg Arg Met Ala Glu Ala Ala His Ala
130                 135                 140

Gly His Lys Thr Ala Gln Ala Gly His Gly Ile Gln Ser Lys Ala Gln
145                 150                 155                 160

Glu Ala Gly Ala Gly Thr Gly Ala Gly Gly Arg Thr Ser Ser
                165                 170                 175

<210> SEQ ID NO 25
<211> LENGTH: 156
<212> TYPE: PRT
<213> ORGANISM: Zea mays

<400> SEQUENCE: 25

Met Ala Asp His His Arg Gly Ala Thr Gly Gly Gly Gly Gly Tyr Gly
 1               5                  10                  15

Asp Leu Gln Arg Gly Gly Gly Met His Gly Glu Ala Gln Gln Gln Gln
                20                  25                  30

Lys Gln Gly Ala Met Met Thr Ala Leu Lys Ala Ala Thr Ala Ala Thr
            35                  40                  45

Phe Gly Gly Ser Met Leu Val Leu Ser Gly Leu Ile Leu Ala Gly Thr
 50                  55                  60

Val Ile Ala Leu Thr Val Ala Thr Pro Val Leu Val Ile Phe Ser Pro
 65                  70                  75                  80

Val Leu Val Pro Ala Ala Ile Ala Leu Ala Leu Met Ala Ala Gly Phe
                 85                  90                  95

Val Thr Ser Gly Gly Leu Gly Val Ala Ala Leu Ser Val Phe Ser Trp
                100                 105                 110

Met Tyr Lys Tyr Leu Thr Gly Lys His Pro Pro Ala Ala Asp Gln Leu
            115                 120                 125

Asp His Ala Lys Ala Arg Leu Ala Ser Lys Ala Arg Asp Val Lys Asp
130                 135                 140

Ala Ala Gln His Arg Ile Asp Gln Ala Gln Gly Ser
145                 150                 155

<210> SEQ ID NO 26
<211> LENGTH: 172
<212> TYPE: PRT
<213> ORGANISM: Oryza sativa

<400> SEQUENCE: 26

Met Ala Asp Arg Asp Arg Ala Gly Gln Tyr Tyr Gln Gln Gln Arg Gly
 1               5                  10                  15

Gln Val Gly Glu Thr Val Lys Gly Ile Leu Pro Glu Lys Ala Pro Ser
                20                  25                  30
```

```
Ala Ser Gln Ala Leu Thr Val Ala Thr Leu Phe Pro Leu Gly Gly Leu
            35                  40                  45

Leu Leu Val Leu Ser Gly Leu Ala Leu Ala Ser Val Val Gly Leu
 50                  55                  60

Ala Val Asp Thr Pro Val Phe Leu Ile Phe Ser Pro Val Leu Val Pro
 65                  70                  75                  80

Ala Ala Leu Leu Ile Gly Leu Ala Val Ala Gly Phe Leu Thr Ser Gly
                 85                  90                  95

Ala Leu Gly Leu Gly Gly Leu Ser Ser Leu Thr Phe Leu Ala Asn Thr
                100                 105                 110

Ala Arg Gln Ala Phe Gln Arg Thr Pro Asp Tyr Val Glu Gln Ala Arg
            115                 120                 125

Arg Arg Met Ala Glu Ala Ala Ala His Ala Gly His Lys Thr Ala Gln
130                 135                 140

Ala Ala His Ala Ile Gln Gly Arg Ala Asp Gln Ala Gly Thr Gly Ala
145                 150                 155                 160

Gly Ala Gly Gly Gly Ala Gly Thr Lys Thr Ser Ser
                165                 170
```

<210> SEQ ID NO 27
<211> LENGTH: 148
<212> TYPE: PRT
<213> ORGANISM: Oryza sativa

<400> SEQUENCE: 27

```
Met Ala Asp Gln His Arg Gly Val Ile Gly Gly Gly Tyr Gly Asp
 1               5                  10                  15

Arg Gly Gly Gln Glu Gln Gln Glu Lys Gln Pro Phe Met Met Thr Ala
                20                  25                  30

Leu Lys Thr Val Thr Ala Ala Thr Ala Gly Gly Ser Met Leu Val Leu
            35                  40                  45

Ser Gly Leu Ile Leu Ala Gly Thr Val Ile Ala Leu Thr Val Ala Thr
 50                  55                  60

Pro Val Leu Val Ile Phe Ser Pro Val Leu Val Pro Ala Ala Ile Ala
 65                  70                  75                  80

Leu Ala Leu Met Ala Ala Gly Phe Val Thr Ser Gly Gly Leu Gly Val
                 85                  90                  95

Ala Ala Leu Ser Val Phe Ser Trp Met Tyr Lys Tyr Leu Thr Gly Lys
                100                 105                 110

His Pro Pro Gly Ala Asp Gln Leu Asp His Ala Lys Ala Arg Leu Ala
            115                 120                 125

Ser Lys Ala Arg Asp Ile Lys Glu Ala Ala Gln His Arg Ile Asp Gln
130                 135                 140

Ala Gln Ala Ser
145
```

<210> SEQ ID NO 28
<211> LENGTH: 158
<212> TYPE: PRT
<213> ORGANISM: Oryza sativa

<400> SEQUENCE: 28

```
Met Ala Gly Gly Gly Gly Ala Val Gly Glu His Tyr Met Arg Val Ile
 1               5                  10                  15

Arg Gly Asp Asp Gly Tyr Gly Asp Asp Gly Gln His Gln Glu Lys
                20                  25                  30

Pro Gly Ala Ala Val Ser Val Ala Lys Gly Ala Ala Ala Ala Ala Ala
```

```
                    35                  40                  45
Ala Gly Ser Met Leu Ala Leu Ala Gly Leu Thr Ala Thr Gly Thr Ala
 50                  55                  60
Leu Ala Leu Ile Val Ala Thr Pro Leu Leu Val Leu Phe Ser Pro Val
 65                  70                  75                  80
Leu Val Pro Ala Ala Phe Ala Ala Ser Leu Leu Ala Ala Gly Leu Ala
                 85                  90                  95
Ser Ser Gly Ala Leu Gly Ala Ala Val Gly Val Leu Ala Trp Met
                100                 105                 110
Tyr Arg Tyr Leu Gln Ser Pro Ser Gly Glu His Ala Pro Ala Gly Ala
            115                 120                 125
Gly Lys Val Glu His Ala Arg Ala Leu Leu Asp Ala Lys Ala His Asp
        130                 135                 140
Val Gly Asp Trp Val Gln His Arg Leu Asp Gln Ala Arg Thr
145                 150                 155
```

<210> SEQ ID NO 29
<211> LENGTH: 144
<212> TYPE: PRT
<213> ORGANISM: Sesamum indicum

<400> SEQUENCE: 29

```
Met Ala Asp Glu Pro His Asp Gln Arg Pro Thr Asp Val Ile Lys Ser
 1               5                  10                  15
Tyr Leu Pro Glu Lys Gly Pro Ser Thr Ser Gln Val Leu Ala Val Val
                 20                  25                  30
Thr Leu Phe Pro Leu Gly Ala Val Leu Leu Cys Leu Ala Gly Leu Ile
             35                  40                  45
Leu Thr Gly Thr Ile Ile Gly Leu Ala Val Ala Thr Pro Leu Phe Val
 50                  55                  60
Ile Phe Ser Pro Ile Leu Val Pro Ala Ala Leu Thr Ile Ala Leu Ala
 65                  70                  75                  80
Val Thr Gly Phe Leu Thr Ser Gly Ala Phe Gly Ile Thr Ala Leu Ser
                 85                  90                  95
Ser Ile Ser Trp Leu Leu Asn Tyr Val Arg Arg Met Arg Gly Ser Leu
                100                 105                 110
Pro Glu Gln Leu Asp His Ala Arg Arg Val Gln Glu Thr Val Gly
            115                 120                 125
Gln Lys Thr Arg Glu Ala Gly Gln Arg Ser Gln Asp Val Ile Arg Pro
        130                 135                 140
```

<210> SEQ ID NO 30
<211> LENGTH: 166
<212> TYPE: PRT
<213> ORGANISM: Sesamum indicum

<400> SEQUENCE: 30

```
Met Ala Asp Arg Asp Arg Pro His Pro His Gln Ile Gln Val His Pro
 1               5                  10                  15
Gln His Pro His Arg Tyr Glu Gly Gly Val Lys Ser Leu Leu Pro Gln
                 20                  25                  30
Lys Gly Pro Ser Thr Thr Gln Ile Leu Ala Ile Ile Thr Leu Leu Pro
             35                  40                  45
Ile Ser Gly Thr Leu Leu Cys Leu Ala Gly Ile Thr Leu Val Gly Thr
 50                  55                  60
Leu Ile Gly Leu Ala Val Ala Thr Pro Val Phe Val Ile Phe Ser Pro
 65                  70                  75                  80
```

```
Val Leu Val Pro Ala Ala Ile Leu Ile Ala Gly Ala Val Thr Ala Phe
                85                  90                  95

Leu Thr Ser Gly Ala Phe Gly Leu Thr Gly Leu Ser Ser Leu Ser Trp
            100                 105                 110

Val Leu Asn Ser Phe Arg Arg Ala Thr Gly Gln Gly Pro Leu Glu Tyr
        115                 120                 125

Ala Lys Arg Gly Val Gln Glu Gly Thr Leu Tyr Val Gly Glu Lys Thr
    130                 135                 140

Lys Gln Ala Gly Glu Ala Ile Lys Ser Thr Ala Lys Glu Gly Gly Arg
145                 150                 155                 160

Glu Gly Thr Ala Arg Thr
                165

<210> SEQ ID NO 31
<211> LENGTH: 145
<212> TYPE: PRT
<213> ORGANISM: Sesamum indicum

<400> SEQUENCE: 31

Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Ala Gly Ser Gln Thr
    130                 135                 140

Ser
145

<210> SEQ ID NO 32
<211> LENGTH: 160
<212> TYPE: PRT
<213> ORGANISM: Theobroma cacao

<400> SEQUENCE: 32

Met Ala Asp Arg Asp Arg Pro His Gln Ile Gln Val His Gln His
1               5                   10                  15

Arg Phe Asp Gln Gly Gly Lys Asn Tyr Gln Ser Ala Ser Gly Pro Ser
            20                  25                  30

Ala Thr Gln Val Leu Ala Val Leu Thr Leu Leu Pro Val Gly Gly Ile
        35                  40                  45

Leu Leu Ala Leu Ala Gly Leu Thr Leu Thr Gly Thr Val Ile Gly Leu
    50                  55                  60

Cys Val Ala Thr Pro Leu Phe Ile Ile Phe Ser Pro Val Leu Val Pro
65                  70                  75                  80
```

```
Ala Ala Ile Ala Val Gly Leu Ala Val Ala Gly Phe Leu Ser Ser Gly
            85                  90                  95

Ala Phe Gly Leu Thr Gly Leu Ser Ser Leu Ala Tyr Val Phe Asn Arg
            100                 105                 110

Leu Arg Arg Ala Thr Gly Thr Glu Gln Leu Asp Met Asp Gln Ala Lys
            115                 120                 125

Arg Arg Met Gln Asp Met Ala Gly Tyr Val Gly Gln Lys Thr Lys Glu
            130                 135                 140

Val Gly Gln Lys Ile Glu Gly Lys Ala Asn Glu Gly Thr Val Arg Thr
145                 150                 155                 160

<210> SEQ ID NO 33
<211> LENGTH: 147
<212> TYPE: PRT
<213> ORGANISM: Theobroma cacao

<400> SEQUENCE: 33

Met Ser Asn Asp Gln Asn Lys Pro Met Thr Gln Lys Leu Tyr Glu Ser
1               5                   10                  15

Ala Pro Ser Ser Arg Gln Ala Ala Lys Phe Leu Thr Ala Thr Thr Leu
            20                  25                  30

Gly Ala Thr Leu Leu Phe Leu Ser Gly Leu Thr Leu Thr Gly Thr Val
            35                  40                  45

Met Ala Leu Ile Met Ala Thr Pro Leu Met Val Ile Phe Ser Pro Ile
        50                  55                  60

Leu Val Pro Ala Gly Val Val Ile Phe Leu Val Ile Thr Gly Phe Leu
65                  70                  75                  80

Phe Ser Gly Gly Cys Gly Val Ala Ala Ile Thr Ala Leu Ser Trp Ile
            85                  90                  95

Tyr Asn Tyr Val Arg Gly Lys His Pro Pro Gly Ala Asp Gln Leu Asp
            100                 105                 110

Tyr Ala Arg Asn Thr Leu Ala Arg Thr Ala Arg Asp Met Thr Glu Lys
            115                 120                 125

Ala Lys Glu Tyr Gly Gln Tyr Val Gln His Lys Ala Gln Glu Val Ala
            130                 135                 140

Gln Gly Ser
145

<210> SEQ ID NO 34
<211> LENGTH: 165
<212> TYPE: PRT
<213> ORGANISM: Olea europaea

<400> SEQUENCE: 34

Met Ala Glu Arg Asp Arg Pro Gln Pro His Gln Val Gln Val His Thr
1               5                   10                  15

Gln Ser Arg Tyr Asp Gln Gly Gly Gly Met Lys Ser Val Leu Pro Lys
            20                  25                  30

Lys Gly Pro Ser Thr Ser Gln Val Leu Ala Val Val Thr Leu Leu Pro
            35                  40                  45

Val Gly Gly Thr Leu Leu Ala Leu Ala Gly Leu Thr Leu Val Glu Ser
        50                  55                  60

Leu Ile Gly Leu Ala Val Thr Thr Pro Leu Phe Ile Ile Phe Ser Pro
65                  70                  75                  80

Val Leu Val Pro Ala Thr Ile Leu Val Gly Leu Ala Val Thr Ala Phe
            85                  90                  95

Leu Thr Ser Gly Ala Phe Gly Leu Thr Gly Leu Ser Ser Leu Ser Trp
```

```
                    100                 105                 110
Val Val Asn Phe Leu Arg Gln Val Ser Gly Ser Met Leu Asp Leu Ala
            115                 120                 125

Lys Ser Arg Met Gly Asp Ala Ala Ile Gln Val Gly Gln Lys Thr Lys
        130                 135                 140

Glu Thr Gly Gln Thr Ile Gln Gln Lys Ala Pro Gly Gly Lys Glu Ser
145                 150                 155                 160

Thr Gly Gly Arg Thr
                165

<210> SEQ ID NO 35
<211> LENGTH: 140
<212> TYPE: PRT
<213> ORGANISM: Perilla frutescens

<400> SEQUENCE: 35

Met Ala Glu Gln His Gln Gln His Arg Pro Thr His Asp Thr Ser Arg
1               5                   10                  15

Asp Leu His Asp Lys Gly Pro Ser Thr Ser Gln Val Leu Ala Val Ala
            20                  25                  30

Thr Leu Phe Pro Val Gly Gly Phe Leu Gly Leu Ala Gly Leu Ile
        35                  40                  45

Leu Thr Gly Thr Leu Phe Gly Leu Ala Val Ser Thr Pro Leu Phe Leu
50                  55                  60

Ile Phe Ser Pro Ile Ile Val Pro Ala Val Ile Ala Ile Ala Leu Ala
65                  70                  75                  80

Val Ala Gly Phe Leu Thr Ser Gly Val Phe Gly Ile Thr Ala Leu Ser
            85                  90                  95

Ser Val Ser Trp Ile Phe Asn Tyr Phe Arg Arg Met Arg Ala Ser Trp
        100                 105                 110

Pro Glu Gln Phe Asp Gln Ala Arg Arg Arg Val Gly Asp Thr Ala Ser
    115                 120                 125

His Met Gly Gln Lys Ala Gln Asp Ala Val Arg Thr
        130                 135                 140

<210> SEQ ID NO 36
<211> LENGTH: 144
<212> TYPE: PRT
<213> ORGANISM: Citrus sinensis

<400> SEQUENCE: 36

Met Ala Glu His Tyr Gln Pro Leu Gln Gln Thr Gln Leu Gln Ser Arg
1               5                   10                  15

Gln Pro Arg Ser His Gln Val Val Lys Ala Ala Thr Ala Val Thr Ala
            20                  25                  30

Gly Gly Ser Leu Leu Val Leu Ser Gly Leu Thr Met Ala Gly Thr Val
        35                  40                  45

Ile Ala Leu Thr Ile Ala Thr Pro Leu Leu Val Ile Cys Ser Pro Val
    50                  55                  60

Leu Val Pro Ala Val Ile Thr Val Ser Leu Leu Ile Met Gly Phe Leu
65                  70                  75                  80

Ala Ser Gly Gly Phe Gly Val Ala Ala Ile Ser Val Leu Ser Trp Ile
            85                  90                  95

Tyr Arg Tyr Val Thr Gly Gly His Pro Pro Gly Ala Asp Gln Leu Glu
        100                 105                 110

Gln Ala Arg Met Lys Leu Ala Gly Lys Ala Arg Glu Met Arg Asp Arg
    115                 120                 125
```

```
Ala Glu Gln Phe Gly Gln Gln Ile Thr Gly Ser Gln Gln Gly Ser
        130                 135                 140
```

<210> SEQ ID NO 37
<211> LENGTH: 148
<212> TYPE: PRT
<213> ORGANISM: Prunus dulcis

<400> SEQUENCE: 37

```
Met Ala Asp Gln His Phe Gln Pro Leu His Phe Gln Gly Ser Tyr
1               5                   10                  15

Gly Gln Gln Gln Pro Arg Ser Tyr Gln Val Ala Lys Ala Ala Thr Ala
            20                  25                  30

Val Thr Ala Gly Gly Ser Leu Leu Val Leu Ser Gly Leu Val Leu Ala
        35                  40                  45

Gly Thr Val Ile Ala Leu Thr Ile Ala Thr Pro Leu Leu Val Ile Phe
    50                  55                  60

Ser Pro Val Leu Val Pro Ala Leu Ile Thr Val Ala Leu Ile Thr Met
65                  70                  75                  80

Gly Phe Leu Thr Ser Gly Gly Phe Gly Val Ala Ala Val Thr Val Leu
                85                  90                  95

Ser Trp Ile Tyr Lys Tyr Val Thr Gly Lys Gln Pro Pro Gly Ala Asp
            100                 105                 110

Gln Leu Asp Gln Ala Arg His Lys Leu Ala Gly Lys Ala Arg Asp Ile
        115                 120                 125

Lys Asp Arg Ala Glu Gln Phe Gly Gln Gln His Val Pro Ser Gly Gln
    130                 135                 140

Gln Gln Ser Ser
145
```

<210> SEQ ID NO 38
<211> LENGTH: 140
<212> TYPE: PRT
<213> ORGANISM: Corylus avellana

<400> SEQUENCE: 38

```
Met Ala Glu His Pro Arg Gln Leu Gln Asp Pro Ala His Gln Pro Arg
1               5                   10                  15

Ser His Gln Val Val Lys Ala Ala Thr Ala Ala Thr Ala Gly Gly Ser
            20                  25                  30

Leu Leu Val Pro Ser Gly Leu Ile Leu Ala Gly Thr Val Ile Ala Leu
        35                  40                  45

Thr Leu Ala Thr Pro Leu Phe Val Ile Phe Ser Pro Val Leu Val Pro
    50                  55                  60

Ala Val Ile Thr Val Ser Leu Ile Ile Met Gly Phe Leu Ala Ser Gly
65                  70                  75                  80

Gly Phe Gly Val Ala Ala Val Thr Val Leu Ser Trp Ile Tyr Arg Tyr
                85                  90                  95

Val Thr Gly Arg His Pro Pro Gly Ala Asp Gln Leu Asp His Ala Arg
            100                 105                 110

Met Lys Leu Ala Ser Lys Ala Arg Glu Met Lys Asp Arg Ala Glu Gln
        115                 120                 125

Phe Gly Gln Gln His Val Thr Gly Ser Gln Gly Ser
    130                 135                 140
```

<210> SEQ ID NO 39
<211> LENGTH: 177

-continued

```
<212> TYPE: PRT
<213> ORGANISM: Perilla frutescens

<400> SEQUENCE: 39

Met Ala Asp Arg Asp Arg Asp Arg Leu His Pro His Gln Ile
1               5                   10                  15

Gln Val His Pro Gln His Pro Gly Gln His Arg Tyr Glu Gly Gly Ala
            20                  25                  30

Lys Ser Leu Leu Pro Gln Lys Gly Pro Ser Thr Gly Gln Ile Leu Ala
        35                  40                  45

Ile Ile Thr Leu Leu Pro Ile Gly Gly Thr Leu Leu Cys Leu Ala Gly
50                  55                  60

Ile Thr Leu Ala Gly Ser Leu Ile Gly Leu Ala Phe Ala Thr Pro Leu
65                  70                  75                  80

Phe Val Ile Phe Ser Pro Val Leu Val Pro Ala Ala Phe Leu Leu Ala
                85                  90                  95

Leu Ala Val Thr Ala Phe Leu Thr Ser Gly Ala Phe Gly Leu Thr Gly
            100                 105                 110

Leu Ser Ser Leu Ser Trp Val Phe Asn Ser Phe Arg Gln Ala Thr Gly
        115                 120                 125

Gln Glu Pro Leu Asp Tyr Ala Lys Arg Arg Met Gln Glu Gly Thr Met
130                 135                 140

Tyr Val Gly Glu Lys Thr Lys Gln Val Gly Glu Thr Ile Lys Ser Lys
145                 150                 155                 160

Ala Gln Glu Gly Gly His Asp Asp Arg Thr Thr Val Leu Gly Gly Arg
                165                 170                 175

Thr

<210> SEQ ID NO 40
<211> LENGTH: 175
<212> TYPE: PRT
<213> ORGANISM: Perilla frutescens

<400> SEQUENCE: 40

Met Ala Asp Arg Asp Arg Asp Arg Leu His Pro His Gln Ile Gln Val
1               5                   10                  15

His Pro Gln His Pro Gly Gln Gln Arg Tyr Glu Gly Gly Ala Lys Ser
            20                  25                  30

Leu Leu Pro Gln Lys Gly Pro Ser Thr Gly Gln Ile Leu Ala Ile Ile
        35                  40                  45

Thr Leu Leu Pro Ile Gly Gly Thr Leu Leu Cys Leu Ala Gly Ile Thr
50                  55                  60

Leu Ala Gly Ser Leu Ile Gly Leu Ala Phe Ala Thr Pro Leu Phe Val
65                  70                  75                  80

Ile Phe Ser Pro Val Leu Val Pro Ala Ala Phe Leu Leu Ala Leu Ala
                85                  90                  95

Val Thr Ala Phe Leu Thr Ser Gly Ala Phe Gly Leu Thr Gly Leu Ser
            100                 105                 110

Ser Leu Ser Trp Val Phe Asn Ser Phe Arg Gln Ala Thr Gly Gln Glu
        115                 120                 125

Pro Leu Asp Tyr Ala Lys Arg Arg Met Gln Glu Gly Thr Met Tyr Val
130                 135                 140

Gly Glu Lys Thr Lys Gln Val Gly Glu Thr Ile Lys Ser Lys Ala Gln
145                 150                 155                 160

Glu Gly Gly His Asp Asp Arg Thr Thr Val Leu Gly Gly Arg Thr
                165                 170                 175
```

```
<210> SEQ ID NO 41
<211> LENGTH: 169
<212> TYPE: PRT
<213> ORGANISM: Arabidopsis thaliana

<400> SEQUENCE: 41

Met Ala Asp Arg Thr Asn Pro Ser Ser His Thr Gln Gln Arg Pro Ile
1               5                   10                  15

Tyr Asn Ser Thr Thr Val Pro Arg Ser Asn Thr Thr Asn His Pro
            20                  25                  30

Leu Ser Ser Leu Leu Arg Gln Leu Leu Gln Ser Gln Ser Pro Asn His
        35                  40                  45

Ser Gly Gln Leu Phe Gly Phe Leu Ala Phe Phe Ile Ser Gly Gly Ile
    50                  55                  60

Leu Leu Leu Leu Thr Gly Ile Thr Val Thr Ala Phe Val Leu Gly Phe
65                  70                  75                  80

Ile Ala Phe Leu Pro Leu Ile Ile Ile Ser Pro Ile Trp Ile Pro
                85                  90                  95

Leu Phe Leu Ile Val Thr Gly Phe Leu Ser Leu Ala Gly Leu Ile Leu
                100                 105                 110

Ala Thr Gly Ala Val Val Ser Trp Leu Tyr Arg Tyr Phe Lys Gly Met
            115                 120                 125

His Pro Leu Arg Ser Asp Gln Val Asp Tyr Ala Arg Ser Arg Ile His
        130                 135                 140

Asp Thr Ala Ala His Val Lys Asp Tyr Ala Gly Gly Tyr Phe His Gly
145                 150                 155                 160

Thr Leu Lys Asp Ala Ala Pro Gly Ala
                165

<210> SEQ ID NO 42
<211> LENGTH: 166
<212> TYPE: PRT
<213> ORGANISM: Arabidopsis thaliana

<400> SEQUENCE: 42

Met Ala Glu Arg Phe Ser Ser Gly Glu Ala Gln Tyr Trp Pro Asn Tyr
1               5                   10                  15

Gly Ser Thr Ala Thr Thr Thr Val Ser Asn Ser Pro Ile Ser Ser Phe
            20                  25                  30

Phe His Gln Leu Arg Ser His Ser Pro Thr Ser Ser Gln Leu Phe Gly
        35                  40                  45

Phe Leu Ala Leu Phe Ile Ser Thr Gly Ile Leu Leu Phe Leu Leu Gly
    50                  55                  60

Val Ser Val Thr Ala Ala Val Leu Gly Phe Ile Val Phe Leu Pro Leu
65                  70                  75                  80

Ile Ile Ile Ser Ser Pro Ile Trp Ile Pro Val Phe Val Val Gly
                85                  90                  95

Gly Phe Leu Thr Val Ser Gly Phe Leu Val Gly Thr Val Ala Leu Val
                100                 105                 110

Ser Trp Thr Tyr Arg Tyr Phe Arg Gly Met His Pro Val Gly Ser Asn
            115                 120                 125

Gln Met Asp Tyr Ala Arg Ser Arg Ile Tyr Asp Thr Ala Ser His Val
        130                 135                 140

Lys Asp Tyr Ala Arg Glu Tyr Gly Gly Tyr Phe His Gly Arg Ala Lys
145                 150                 155                 160
```

Asp Ala Ala Pro Gly Ala
            165

<210> SEQ ID NO 43
<211> LENGTH: 22
<212> TYPE: DNA
<213> ORGANISM: Artificial
<220> FEATURE:
<223> OTHER INFORMATION: CcOLE-1 fwd primer

<400> SEQUENCE: 43
ttcgttatct ttagccccat tt                                              22

<210> SEQ ID NO 44
<211> LENGTH: 22
<212> TYPE: DNA
<213> ORGANISM: Artificial
<220> FEATURE:
<223> OTHER INFORMATION: CcOLE-1 rev primer

<400> SEQUENCE: 44
cataggcaag attaacaagg at                                              22

<210> SEQ ID NO 45
<211> LENGTH: 17
<212> TYPE: DNA
<213> ORGANISM: Artificial
<220> FEATURE:
<223> OTHER INFORMATION: CcOLE-2 fwd primer

<400> SEQUENCE: 45
gtggcagcgt tgagcgt                                                    17

<210> SEQ ID NO 46
<211> LENGTH: 24
<212> TYPE: DNA
<213> ORGANISM: Artificial
<220> FEATURE:
<223> OTHER INFORMATION: CcOLE-2 rev primer

<400> SEQUENCE: 46
gacaataatg catgaatacc acaa                                            24

<210> SEQ ID NO 47
<211> LENGTH: 20
<212> TYPE: DNA
<213> ORGANISM: Artificial
<220> FEATURE:
<223> OTHER INFORMATION: CcOLE-3 fwd primer

<400> SEQUENCE: 47
gagatcaagg tggaagggaa                                                 20

<210> SEQ ID NO 48
<211> LENGTH: 22
<212> TYPE: DNA
<213> ORGANISM: Artificial
<220> FEATURE:
<223> OTHER INFORMATION: CcOLE-3 rev primer

<400> SEQUENCE: 48 gaaaccctc aacaaacaaa ga                                               22

<210> SEQ ID NO 49
<211> LENGTH: 21
<212> TYPE: DNA
<213> ORGANISM: Artificial

```
<220> FEATURE:
<223> OTHER INFORMATION: CcOLE-4 fwd primer

<400> SEQUENCE: 49
ctgacactgg ctggaacaat a                                              21

<210> SEQ ID NO 50
<211> LENGTH: 23
<212> TYPE: DNA
<213> ORGANISM: Artificial
<220> FEATURE:
<223> OTHER INFORMATION: CcOLE-4 rev primer

<400> SEQUENCE: 50
gcacaacatt ccatcaagta tct                                            23

<210> SEQ ID NO 51
<211> LENGTH: 22
<212> TYPE: DNA
<213> ORGANISM: Artificial
<220> FEATURE:
<223> OTHER INFORMATION: CcOLE-5 fwd primer

<400> SEQUENCE: 51
tggcatccta cttctcctca ct                                             22

<210> SEQ ID NO 52
<211> LENGTH: 24
<212> TYPE: DNA
<213> ORGANISM: Artificial
<220> FEATURE:
<223> OTHER INFORMATION: CcOLE-5 rev primer

<400> SEQUENCE: 52
ctctctagca taatccttca cctg                                           24

<210> SEQ ID NO 53
<211> LENGTH: 21
<212> TYPE: DNA
<213> ORGANISM: Artificial
<220> FEATURE:
<223> OTHER INFORMATION: RPL39 fwd primer

<400> SEQUENCE: 53
tggcgaagaa gcagaggcag a                                              21

<210> SEQ ID NO 54
<211> LENGTH: 20
<212> TYPE: DNA
<213> ORGANISM: Artificial
<220> FEATURE:
<223> OTHER INFORMATION: RPL39 rev primer

<400> SEQUENCE: 54
ttgaggggga gggtaaaaag                                                20

<210> SEQ ID NO 55
<211> LENGTH: 26
<212> TYPE: DNA
<213> ORGANISM: Artificial
<220> FEATURE:
<223> OTHER INFORMATION: OLE-1a primer

<400> SEQUENCE: 55
aagttgatgg acccttctga ggaagg                                         26
```

```
<210> SEQ ID NO 56
<211> LENGTH: 25
<212> TYPE: DNA
<213> ORGANISM: Artificial
<220> FEATURE:
<223> OTHER INFORMATION: OLE-1b primer

<400> SEQUENCE: 56
agctggtagt gctcagccat gaagg                                          25

<210> SEQ ID NO 57
<211> LENGTH: 20
<212> TYPE: DNA
<213> ORGANISM: Artificial
<220> FEATURE:
<223> OTHER INFORMATION: OLE-1 fwd primer

<400> SEQUENCE: 57
ccgactcatg aaggcgtctt                                                20

<210> SEQ ID NO 58
<211> LENGTH: 18
<212> TYPE: DNA
<213> ORGANISM: Artificial
<220> FEATURE:
<223> OTHER INFORMATION: OLE-1 rev primer

<400> SEQUENCE: 58
gtcctgcagc gccacttt                                                  18

<210> SEQ ID NO 59
<211> LENGTH: 14
<212> TYPE: DNA
<213> ORGANISM: Artificial
<220> FEATURE:
<223> OTHER INFORMATION: OLE-1 probe

<400> SEQUENCE: 59
ccaggagcaa atgg                                                      14

<210> SEQ ID NO 60
<211> LENGTH: 17
<212> TYPE: DNA
<213> ORGANISM: Artificial
<220> FEATURE:
<223> OTHER INFORMATION: OLE-2 fwd primer

<400> SEQUENCE: 60
gaccgggcaa ggcaaaa                                                   17

<210> SEQ ID NO 61
<211> LENGTH: 20
<212> TYPE: DNA
<213> ORGANISM: Artificial
<220> FEATURE:
<223> OTHER INFORMATION: OLE-2 rev primer

<400> SEQUENCE: 61
gctcagccct gtccttcatc                                                20

<210> SEQ ID NO 62
<211> LENGTH: 18
<212> TYPE: DNA
<213> ORGANISM: Artificial
<220> FEATURE:
<223> OTHER INFORMATION: OLE-2 probe

<400> SEQUENCE: 62
```

-continued ctgctcttaa ggctaggg                                              18

<210> SEQ ID NO 63
<211> LENGTH: 19
<212> TYPE: DNA
<213> ORGANISM: Artificial
<220> FEATURE:
<223> OTHER INFORMATION: OLE-3 fwd primer

<400> SEQUENCE: 63
ccgccacaac agcttcaag                                             19

<210> SEQ ID NO 64
<211> LENGTH: 19
<212> TYPE: DNA
<213> ORGANISM: Artificial
<220> FEATURE:
<223> OTHER INFORMATION: OLE-3 rev primer

<400> SEQUENCE: 64
acaccgcctt ccccatatc                                             19

<210> SEQ ID NO 65
<211> LENGTH: 16
<212> TYPE: DNA
<213> ORGANISM: Artificial
<220> FEATURE:
<223> OTHER INFORMATION: OLE-3 probe

<400> SEQUENCE: 65
acaccatcag cacctg                                                16

<210> SEQ ID NO 66
<211> LENGTH: 23
<212> TYPE: DNA
<213> ORGANISM: Artificial
<220> FEATURE:
<223> OTHER INFORMATION: OLE-4 fwd primer

<400> SEQUENCE: 66
attgctcatg cagctaagga gat                                        23

<210> SEQ ID NO 67
<211> LENGTH: 17
<212> TYPE: DNA
<213> ORGANISM: Artificial
<220> FEATURE:
<223> OTHER INFORMATION: OLE-4 rev primer

<400> SEQUENCE: 67
tgagcctgct gcccaaa                                               17

<210> SEQ ID NO 68
<211> LENGTH: 16
<212> TYPE: DNA
<213> ORGANISM: Artificial
<220> FEATURE:
<223> OTHER INFORMATION: OLE-4 probe

<400> SEQUENCE: 68
agggacaaag ctgaac                                                16

<210> SEQ ID NO 69
<211> LENGTH: 18
<212> TYPE: DNA
<213> ORGANISM: Artificial

```
<220> FEATURE:
<223> OTHER INFORMATION: OLE-5 fwd primer

<400> SEQUENCE: 69
ggttcggacc gggttgac                                                     18

<210> SEQ ID NO 70
<211> LENGTH: 21
<212> TYPE: DNA
<213> ORGANISM: Artificial
<220> FEATURE:
<223> OTHER INFORMATION: OLE-5 rev primer

<400> SEQUENCE: 70
tcacctgact tgccgtattg c                                                 21

<210> SEQ ID NO 71
<211> LENGTH: 17
<212> TYPE: DNA
<213> ORGANISM: Artificial
<220> FEATURE:
<223> OTHER INFORMATION: OLE-5 probe

<400> SEQUENCE: 71
atgcaagaag ccgaatt                                                      17

<210> SEQ ID NO 72
<211> LENGTH: 17
<212> TYPE: DNA
<213> ORGANISM: Artificial
<220> FEATURE:
<223> OTHER INFORMATION: 11S fwd primer

<400> SEQUENCE: 72
cgtgctggcc gcattac                                                      17

<210> SEQ ID NO 73
<211> LENGTH: 20
<212> TYPE: DNA
<213> ORGANISM: Artificial
<220> FEATURE:
<223> OTHER INFORMATION: 11S rev primer

<400> SEQUENCE: 73
ggaggctgct gaggatagga                                                   20

<210> SEQ ID NO 74
<211> LENGTH: 19
<212> TYPE: DNA
<213> ORGANISM: Artificial
<220> FEATURE:
<223> OTHER INFORMATION: 11S probe

<400> SEQUENCE: 74
actgttaata gccaaaaga                                                    19

<210> SEQ ID NO 75
<211> LENGTH: 20
<212> TYPE: DNA
<213> ORGANISM: Artificial
<220> FEATURE:
<223> OTHER INFORMATION: STO-1 fwd primer

<400> SEQUENCE: 75
gcactggaag gcctcttttg                                                   20
```

```
<210> SEQ ID NO 76
<211> LENGTH: 23
<212> TYPE: DNA
<213> ORGANISM: Artificial
<220> FEATURE:
<223> OTHER INFORMATION: STO-1 rev primer

<400> SEQUENCE: 76
ggacttgcac cagtgagaag ttt                                              23

<210> SEQ ID NO 77
<211> LENGTH: 14
<212> TYPE: DNA
<213> ORGANISM: Artificial
<220> FEATURE:
<223> OTHER INFORMATION: STO-1 probe

<400> SEQUENCE: 77
agggctcccc tccg                                                        14

<210> SEQ ID NO 78
<211> LENGTH: 21
<212> TYPE: DNA
<213> ORGANISM: Artificial
<220> FEATURE:
<223> OTHER INFORMATION: RPL fwd primer

<400> SEQUENCE: 78
gaacaggccc atcccttatt g                                                21

<210> SEQ ID NO 79
<211> LENGTH: 18
<212> TYPE: DNA
<213> ORGANISM: Artificial
<220> FEATURE:
<223> OTHER INFORMATION: RPL39 rev primer 2

<400> SEQUENCE: 79
cggcgcttgg caattgta                                                    18

<210> SEQ ID NO 80
<211> LENGTH: 16
<212> TYPE: DNA
<213> ORGANISM: Artificial
<220> FEATURE:
<223> OTHER INFORMATION: RPL39 probe

<400> SEQUENCE: 80
atgcgcactg acaaca                                                      16

<210> SEQ ID NO 81
<211> LENGTH: 28
<212> TYPE: DNA
<213> ORGANISM: Artificial
<220> FEATURE:
<223> OTHER INFORMATION: TG-702 primer

<400> SEQUENCE: 81
ttgaagctta cgacaggttt cccgactg                                         28

<210> SEQ ID NO 82
<211> LENGTH: 34
<212> TYPE: DNA
<213> ORGANISM: Artificial
<220> FEATURE:
<223> OTHER INFORMATION: TG-703 primer

<400> SEQUENCE: 82
```

-continued

```
gcagatctac catgggcggt ggacggtagc ttat                34

<210> SEQ ID NO 83
<211> LENGTH: 24
<212> TYPE: DNA
<213> ORGANISM: Artificial
<220> FEATURE:
<223> OTHER INFORMATION: CHI intron fwd primer

<400> SEQUENCE: 83
cccacctgga gcctctattc tgtt                           24

<210> SEQ ID NO 84
<211> LENGTH: 20
<212> TYPE: DNA
<213> ORGANISM: Artificial
<220> FEATURE:
<223> OTHER INFORMATION: CHI intron rev primer

<400> SEQUENCE: 84
ccccgtcggc ctcaagtttc                                20
```

OLEOSIN GENES AND PROMOTERS FROM COFFEE

This is a U.S. National Application of International Application No. PCT/US06/26121, filed Jun. 30, 2006, which claims benefit of U.S. Provisional Application No. 60/696,445, filed Jul. 1, 2005, the entire contents of each of which are incorporated by reference herein.

FIELD OF THE INVENTION

The present invention relates to the field of agricultural biotechnology. In particular, the invention features oleosin- and steroleosin-encoding polynucleotides from coffee plants, promoter sequences from coffee oleosin genes, and methods for using these polynucleotides and promoters for gene regulation and manipulation of flavor, aroma and other features of coffee beans.

BACKGROUND OF THE INVENTION

Various publications, including patents, published applications and scholarly articles, are cited throughout the specification. Each of these publications is incorporated by reference herein, in its entirety. Citations not fully set forth within the specification may be found at the end of the specification.

Coffee aroma and flavor are key components in consumer preference for coffee varieties and brands. Coffee's characteristic aroma and flavor stems from a complex series of chemical reactions involving flavor precursors (Maillard reactions) that occur during the roasting of the bean. Flavor precursors include chemical compounds and biomolecules present in the green coffee bean. To date, over 800 chemicals and biomolecules have been identified as contributing to coffee flavor and aroma (Montavon et al., 2003, J. Agric. Food Chem., 51:2328-34; Clarke & Vitzthum, 2001, *Coffee: Recent Developments*. Blackwell Science).

Because coffee consumers are becoming increasingly sophisticated, it is desirable to produce coffee with improved aroma and flavor in order to meet consumer preferences. Both aroma and flavor may be artificially imparted into coffee products through chemical means. See, for example, U.S. Pat. No. 4,072,761 (aroma) and U.S. Pat. No. 3,962,321 (flavor). An alternative approach would be to use techniques of molecular biology to either add aroma and flavor-enhancing elements that do not naturally occur in coffee beans, or to enhance those elements responsible for the flavor and aroma that are naturally found in the coffee bean. Genetic engineering is particularly suited to achieve these ends. For example, coffee proteins from different coffee species may be swapped. In the alternative, the expression of genes encoding naturally occurring coffee proteins that positively contribute to coffee flavor may be enhanced. Conversely, the expression of genes encoding naturally occurring coffee proteins that negatively contribute to coffee flavor may be suppressed.

The endogenous coffee proteins whose expression could be the target of genetic manipulation, and whether and to what extent production of such coffee proteins should be enhanced or suppressed has been empirically determined. The 11S storage protein has been identified as one such candidate coffee protein. (Montavon et al., 2003, J. Agric. Food Chem. 51:2335-43). Coffee oleosin, because of its role in oil storage, is another candidate coffee protein. Coffee oils are known constituents of coffee aroma and flavor. For example, (E)-2-nonenal, and trans-trans-2-4-decadienal are lipid derived volatiles important to coffee aroma (Akiyama et al., 2003; Variyar et al., 2003). Therefore, increasing or decreasing the stores of these oils in the coffee bean should have a measurable effect on the aroma and flavor of the coffee. Oleosins also form lipid bilayers and may contribute to lipid content as well.

Oleosins have been detected in a variety of plant species including oilseed rape, (Keddie et al., 1992), african oil palm (NCBI), cotton (Hughes et al, 1993), sunflower (Thorts et al., 1995), barely (Aalen et al, 1994; 1995), rice (Wu et al., 1998), almond (Garcia-Mas et al., 1995), cacao (Guilloteau et al., 2003) and maize (Qu and Huang, 1990; Lee and Huang, 1994). In plant seeds, oil bodies, also called oleosomes, are maintained by oleosins. These oil bodies are thought to serve as a reservoir of triacylglycerols (TAG) (Tzen et al., 1993). One function of oleosins is to organize the lipid reserves of seeds in small, easily accessed structures (Huang et al., 1996). Seed oil bodies range in diameter from 0.5 to 2 $\mu M$ (Tzen et al., 1993), providing a high surface to volume ratio, which is believed to facilitate the rapid conversion of TAGs into free fatty acids via lipase mediated hydrolysis at the oil body surface (Huang et al., 1996). In seeds containing large amounts of oils, such as oilseed rape, oleosins represent 8%-20% of the total protein (Li et al., 2002) and oleosins represent 79% of the proteins associated with arabidopsis oil bodies (Jolivet et al., 2004). Oleosins cover the surface of these oil bodies (Huang, 1996), where they are thought to help stabilize the lipid body during desiccation of the seed by preventing coalescence of the oils. Related lipid containing particles are also found in certain specialized cells. For example, the tapetum, a structure involved in the development of pollen; also has specific oil body-like lipid particles called tapetosomes. These oil body-like particles are involved in providing functional components required for microspore and pollen development (Murphy et al., 1998; Hernandez-Pinzon et al., 1999).

Oleosin proteins are composed of three distinctive domains: a central conserved hydrophobic fragment of approximately 72 amino acids flanked by a highly variable N-terminal carboxylic motif and a C-terminal amphipathic α-helix (Huang, 1996; Li et al, 2002). The lengths of the amino and carboxy portions are highly variable, and as a consequence, oleosins can range in size from 14 to 45 kDa (Tai et al., 2002; Kim et al., 2002). The amphipathic amino and carboxylic portions allow the protein to reside stably on the surface of the oil bodies (Huang, 1996). The amino acids at the center of the hydrophobic region contain three conserved prolines and one conserved serine, which form the proline KNOT Motif. This motif is believed to allow the central fragment to fold into a hydrophobic hairpin, which anchors the oleosin in the oily central matrix (Huang, 1996). The role of the proline KNOT motif on protein function was further investigated by Abell et al. (1997) who showed that, if the three proline residues were substituted by leucine residues, an oleosin-beta-glucuronidase fusion protein failed to target to oil bodies in both transient embryo expression and in stably transformed seeds.

Oleosins have been classified as high or low-$M_r$ isoforms (H- and L-oleosin) depending on the relative molecular masses (Tzen et al, 1990). Sequence analysis showed that the main difference between the H- and L-oleosins was the insertion of 18 residues in the C-terminal domain of H-oleosins (Tai et al., 2002) and Tzen et al. (1998) have shown that both forms coexist in oil bodies. In *Zea mays*, Lee and Huang (1994) identified three genes, OLE16, OLE17 and OLE18 with molecular weights of 16, 17 and 18 kDa, respectively, that are expressed during seed maturation. The corresponding protein ratios are 2:1:1 respectively in isolated oil bodies (Lee and Huang, 1994; Ting et al., 1996). Lee et al. (1995) classed OLE16 as an L-oleosin and OLE17 and OLE18 as H-oleosins, indicating that oil bodies of *Z. mays* contain equal amounts of H- and L-oleosins in oil bodies. Furthermore, the oil bodies of rice embryos were found to contain a similar amount of two distinct oleosins of molecular masses 18 and 16 kDa corresponding to the H form and L-form respectively (Tzen et al., 1998; Wu et al., 1998). Two oleosins were also identified in the seeds of *Theobroma cacao* (Guilloteau et al., 2003). At 15 and 16.1 kDa these proteins represent one L-form and one H-form respectively.

Kim et al. (2002) have characterized the oleosin genes in *Arabidopsis* into three groups. The first group consists of oleosins expressed specifically in the seeds (S), the second expressed in the seeds and the floral microspores (SM) and the final group expressed in the floret tapetum (T). Of the sixteen oleosin genes identified in the *Arabidopsis* genome, five genes were shown to be specifically expressed in maturing seeds, three genes expressed in maturing seeds and floral microspores and eight in the floral tapetum (Kim et al., 2002). The five seed specific oleosins of *Arabidopsis* have been previously classed as 3 H-form oleosins and 2 L-form oleosins by Wu et al. (1999). Sesame, maize and rice have all been shown to encode three seed-specific oleosins (Tai et al., 2002; Ting et al., 1996; Chuang et al., 1996; Wu et al., 1998; Tzen et al., 1998).

Oleosin expression is believed to be developmentally and spatially regulated, primarily at the level of transcription (Keddie et al., 1994). Wu et al. (1998) showed that transcripts of two rice oleosins appeared seven days after pollination and vanished in mature seeds. A similar result was obtained by Guilloteau et al. (2003) who showed that the level of the two cacao oleosin transcripts decreased in mature seeds. While oleosin gene transcription has been studied in a semi-quantitative manner in a number of seed types, there are no reports in which the transcript levels of most, or all, of the oleosins in one seed type have been quantitatively determined during seed development.

Despite the fact that coffee grains have an oil content of between 10 and 16%, little is known about oleosin proteins in coffee. There is a dearth of scientific data regarding the number of coffee oleosins, their protein structure, their expression levels and distribution throughout the coffee plant and among coffee species, their oil storage capabilities, and the regulation of their expression on the molecular level. Thus, there is a need to identify and characterize coffee oleosin proteins, genes, and genetic regulatory elements. Such information will enable coffee oleosin proteins to be genetically manipulated, with the goal of improving one or more features of the coffee, including oil content and stability, which in turn can affect roasting parameters, ultimately impacting the aroma and flavor of the coffee.

For purposes of enhancing or suppressing the production of coffee proteins such as oleosins, it is desirable to have available a set of promoters compatible with the coffee plant. In addition, any genetic manipulation should ideally be localized primarily or solely to the coffee grain, and should not adversely affect reproduction or propagation of the coffee plant.

Seed-specific promoters have been described. Examples of such promoters include the 5' regulatory regions from such genes as cruciperan (U.S. Pat. No. 6,501,004), napin (Kridl et al., Seed Sci. Res. 1:209:219, 1991), phaseolin (Bustos et al, Plant Cell, 1(9):839-853, 1989), soybean trypsin inhibitor (Riggs et al., Plant Cell 1(6):609-621, 1989), ACP (Baerson et al., Plant Mol. Biol., 22(2):255-267, 1993), stearoyl-ACP desaturase (Slocombe et al., Plant Physiol. 104(4):167-176, 1994), soybean a' subunit of beta-conglycinin (P-Gm7S, Chen et al., Proc. Natl. Acad. Sci. 83:8560-8564, 1986), *Vicia faba* USP (P-Vf.Usp, U.S. patent application Ser. No. 10/429, 516). In addition, a *Zea mays* L3 oleosin promoter has been described. (P-Zm.L3, Hong et al., Plant Mol. Biol., 34(3): 549-555, 1997).

Seed-specific promoters have found application in plant transformation. For example, groups have used genetic manipulation to modify the level of constituents of seeds. See, Selvaraj et al., U.S. Pat. No. 6,501,004, Peoples et al. U.S. Pat. No. 6,586,658, Shen et al., U.S. patent application Ser. No. 10/223,646, Shewmaker et al., U.S. patent application Ser. No. 10/604,708, and Wahlroos et al., U.S. patent application Ser. No. 10/787,393. Of note is that oleosin promoters have been used successfully in these systems.

However, seed-specific promoters, and more specifically, coffee oleosin promoters heretofore have not been used in the transformation of coffee plants. Thus, there exists a need to have available additional gene regulatory sequences to control the expression of coffee proteins. In the same vein, there exists a need to have available gene regulatory sequences to control the expression of oleosins in coffee plants. Furthermore, there exists a need to have available gene regulatory sequences to control the expression of coffee proteins in the coffee grain. In this regard, promoters specific to gene expression in the coffee grain are highly attractive candidates, among these promoters are coffee oleosin promoters.

SUMMARY OF THE INVENTION

One aspect of the present invention features nucleic acid molecules isolated from coffee (*Coffea* spp.), having coding sequences that encode oleosins. In certain embodiments, the coding sequences encode oleosins having molecular weights of between about 14 kDa and about 19 kDa.

In certain embodiments, the coding sequences encode fragments of oleosins, for example, (a) residues 1 to about 27, about 28 to about 109, or about 110 to the C-terminus of SEQ ID NOS: 8 or 9; (b) residues 1 to about 15, about 16 to about 89, or about 90 to the C-terminus of SEQ ID NO:10; (c) residues 1 to about 30, about 31 to about 114, or about 115 to the C-terminus of SEQ ID NO:11; (d) residues 1 to about 18, about 19 to about 89, or about 90 to the C-terminus of SEQ ID NO:12; or (e) residues 1 to about 40, about 41 to about 115, or about 116 to the C-terminus of SEQ ID NO:13. In certain embodiments, the encoded oleosins have amino acid sequences greater than 80% identical to any one of SEQ ID NOS: 8-13.

Another aspect of the invention features a nucleic acid molecule isolated from coffee (*Coffea* spp.), having a coding sequence that encodes a steroleosin. In certain embodiments, the nucleic acid molecule encodes a fragment of a steroleosin protein, for example, residues 1 to about 50, about 50 to about 80, about 81 to about 102, about 103 to about 307, and about 308 to the carboxy terminus of SEQ ID NO:14. In other embodiments, the nucleic acid molecule encodes a steroleosin having an amino acid sequence greater than 80% identical to SEQ ID NO:14.

The coffee oleosin- or steroleosin encoding nucleic acid molecules described above may be in one of several forms, including (1) a gene having an open reading frame that comprises the coding sequence, (2) a mRNA molecule produced by transcription of that gene, (3) a cDNA molecule produced by reverse transcription of that mRNA, or (4) an oligonucleotide between 8 and 100 bases in length, which is complementary to a segment of any of the foregoing forms of the nucleic acid molecule.

Other aspects of the invention feature vectors comprising the coffee oleosin- or steroleosin-encoding nucleic acid molecules described above. In certain embodiments, the vector is an expression vector, such as a plasmid, cosmid, baculovirus, bacmid, bacterial, yeast or viral vector. In certain embodiments, the vector contains the oleosin or steroleosin coding sequence operably linked to a constitutive promoter. In other embodiments, the coding sequence is operably linked to an inducible promoter. In other embodiments, the coding sequence is operably linked to a tissue specific promoter, which is a seed specific promoter in some embodiments, and a coffee seed specific promoter in particular embodiments. In those embodiments, the coffee seed specific promoter may be an oleosin gene promoter.

Another aspect of the invention features host cells transformed with a vector of the type described above. The host cells may be plant cells, bacterial cells, fungal cells, insect cells or mammalian cells. In certain embodiments, the host cells are plant cells, which may be from coffee, tobacco, Arabidopsis, maize, wheat, rice, soybean barley, rye, oats, sorghum, alfalfa, clover, canola, safflower, sunflower, peanut, cacao, tomatillo, potato, pepper, eggplant, sugar beet, carrot, cucumber, lettuce, pea, aster, begonia, chrysanthemum, delphinium, zinnia, and turfgrasses. The invention also features fertile plants produced from the plant cells.

Another aspect of the invention features a method to modulate flavor or aroma of coffee beans, comprising modulating production of one or more oleosins or steroleosins within coffee seeds. In certain embodiments, the method involves increasing production of one or more oleosins or steroleosins, such as by increasing expression of one or more endogenous oleosin or steroleosin genes within the coffee seeds, or by introducing an oleosin- or steroleosin-encoding transgene into the plant. In other embodiments, the method involves decreasing production of one or more oleosins or steroleosins, such as by introducing a nucleic acid molecule into the coffee that inhibits oleosin or steroleosin gene expression.

Another aspect of the invention features a promoter isolated from a coffee plant gene that encodes an oleosin. In certain embodiments, the promoter is isolated from a gene encodes an oleosin having an amino acid sequence greater than 80% identical to any one of SEQ ID NOS: 8-13. In particular embodiments, the promoter contains one or more regulatory sequences selected from the group consisting of TTAAAT, TGTAAAGT, CAAATG, CATGTG, CATGCAAA, CCATGCA and ATATTTATT. In a specific embodiment, the promoter comprises SEQ ID NO:15.

Another aspect of the invention features a chimeric gene comprising an oleosin gene promoter, operably linked to one or more coding sequences. Vectors, and host cells and fertile transgenic plants comprising such chimeric genes are also featured.

Other features and advantages of the present invention will be understood by reference to the drawings, detailed description and examples that follow.

BRIEF DESCRIPTION OF THE DRAWINGS

FIG. 2. Optimal alignment of the Coffea canephora steroleosin protein, CcSTO-1 sequence with the two closest databank sequences. Accession numbers of the aligned oleosin sequences are: CAB39626 for A. thaliana (At) (AtSTOLE-7, SEQ ID NO.:17), AY841276 for Coffea canephora (SEQ ID NO:14), and AF498264 for Sesamum indicum (Lin and Tzen, 2004) (SiSTO-B, SEQ ID NO.:16). The alignments were generated with the clustal W program in the Lasergene software package (DNASTAR) and then adjusted manually to optimize the alignment. Conserved regions are boxed. The locations of the conserved S-(12X)-Y-(3X)-K potential active site and P-(11X)-P proline KNOT motif are indicated, with highly conserved residues shown in bold (Lin et al., 2002). The NADPH and sterol binding regions identified by Lin et al. (2002) are also indicated.

LP, large pericarp; YP, yellow pericarp; RP, red pericarp; St, stem; Le, leaf; Fl, flower; Rt, root.

Figure 6:
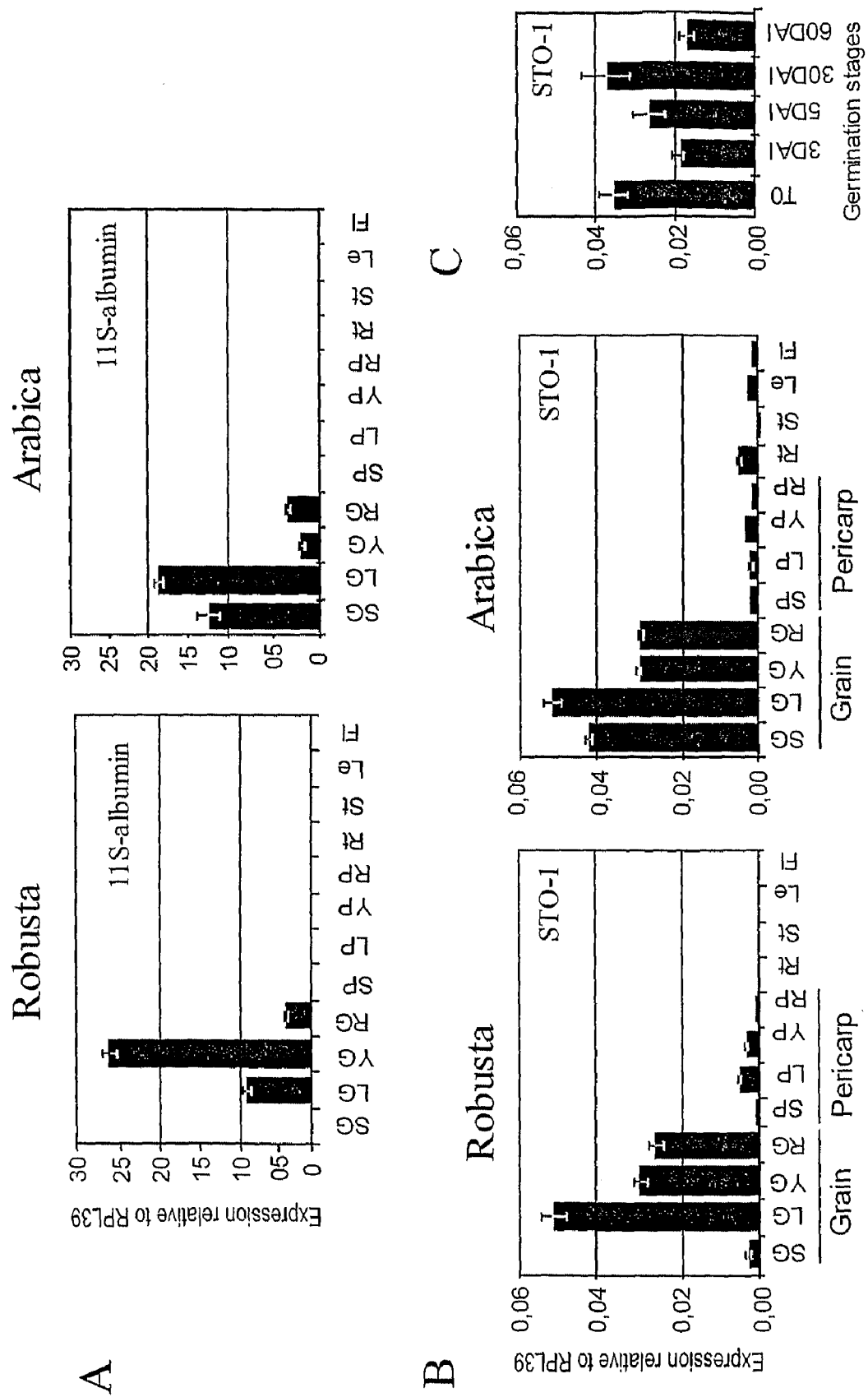

FIG. 6. Expression of coffee oleosin and steroleosin genes. A) Expression of the CSP1 gene coding for the 11S storage protein in *Coffea canephora* and *Coffea arabica* in different tissues and during seed maturation. Reverse transcription was carried out with equal amounts of total RNA. SG, Small green grain; LG, large grain; YG, yellow grain; RG, ripe grain; SGP, Small green pericarp; LP, large pericarp; YP, yellow pericarp; RP, red pericarp; St, stem; Le, leaf; Fl, flower; Rt, root. B) Expression of steroleosin in various tissues determined by quantitative PCR. C) Expression of steroleosin in *Coffea arabica* (T-2308) during seed germination. Transcript levels were analysed in the grain at five different germination stages. Mature (fully developed grain), T0 (following imbibition), 2DAI (two days after imbibition), 5DAI, 30DAI and 60DAI.

Figure 7:
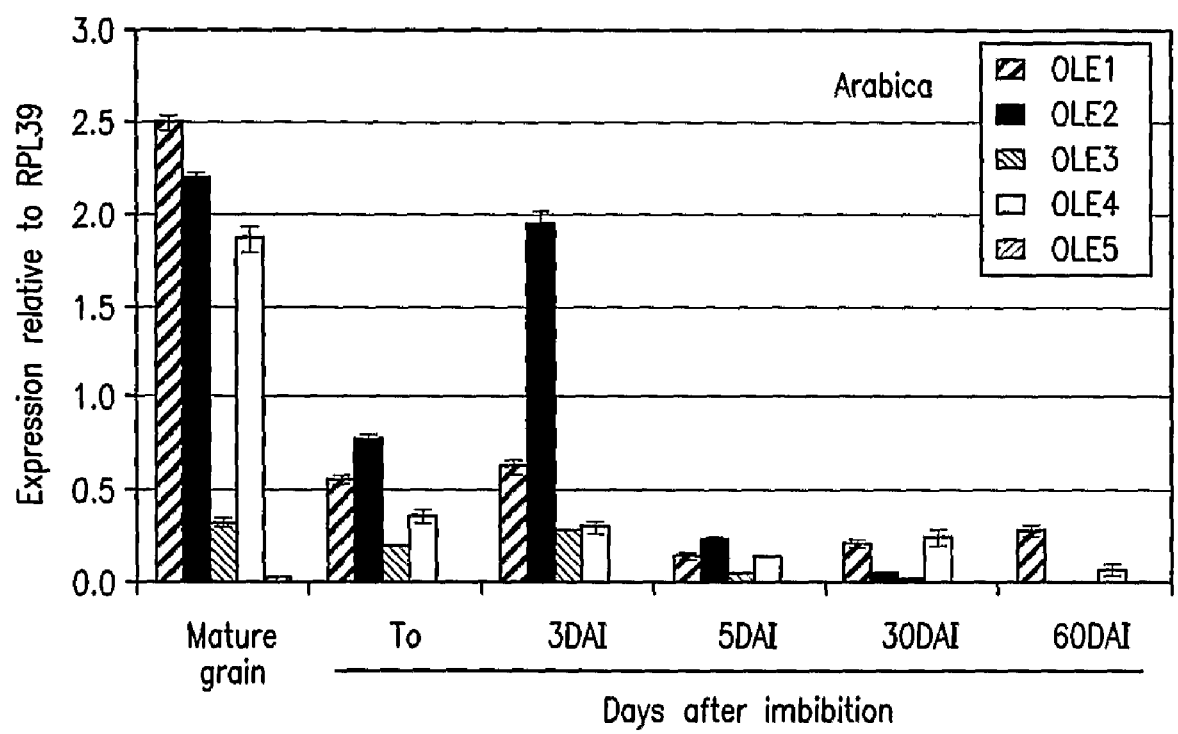

FIG. 7. Oleosin transcript levels in *Coffea arabica* (T-2308) during seed germination. Transcript levels were analysed in the grain at five different germination stages. T0 (following imbibition), 3DAI (three days after imbibition), 5DAI, 30DAI and 60DAI.

FIG. 8. In silico genomic sequence of CcOLE-1 gene. The primers used for genewalker are underlined in the sequence. Sequence analysis of the CcOLE-1 promoter (pOLE-1, SEQ ID NO.:15). Nucleotide and deduced protein sequence of OLE-1 from *C. canephora* (SEQ ID NO:2, SEQ ID NO:9). An arrow indicates the transcription start site. The putative TATA-box is shown (═══). The RY-motif is indicated by a box. The 'endoderm motif' (......), AT-lich enhancer-like motif (~~~) and E-Boxes (•-•) are indicated. The accession number of the CcOLE-1 promoter (POLE-1, SEQ ID NO.: 15) sequence deposited in the EMBL/Genebank database is AY841277. Complete transcribed sequence of CcOLE-1 is shown in bold. The CcOLE-1 amino acids are indicated below the first base of the codon. The start and stop codon are indicated in boxes. A HindIII restriction site is indicated at position 123 bp from the transcriptional start site.

Figures 9A, 9B:
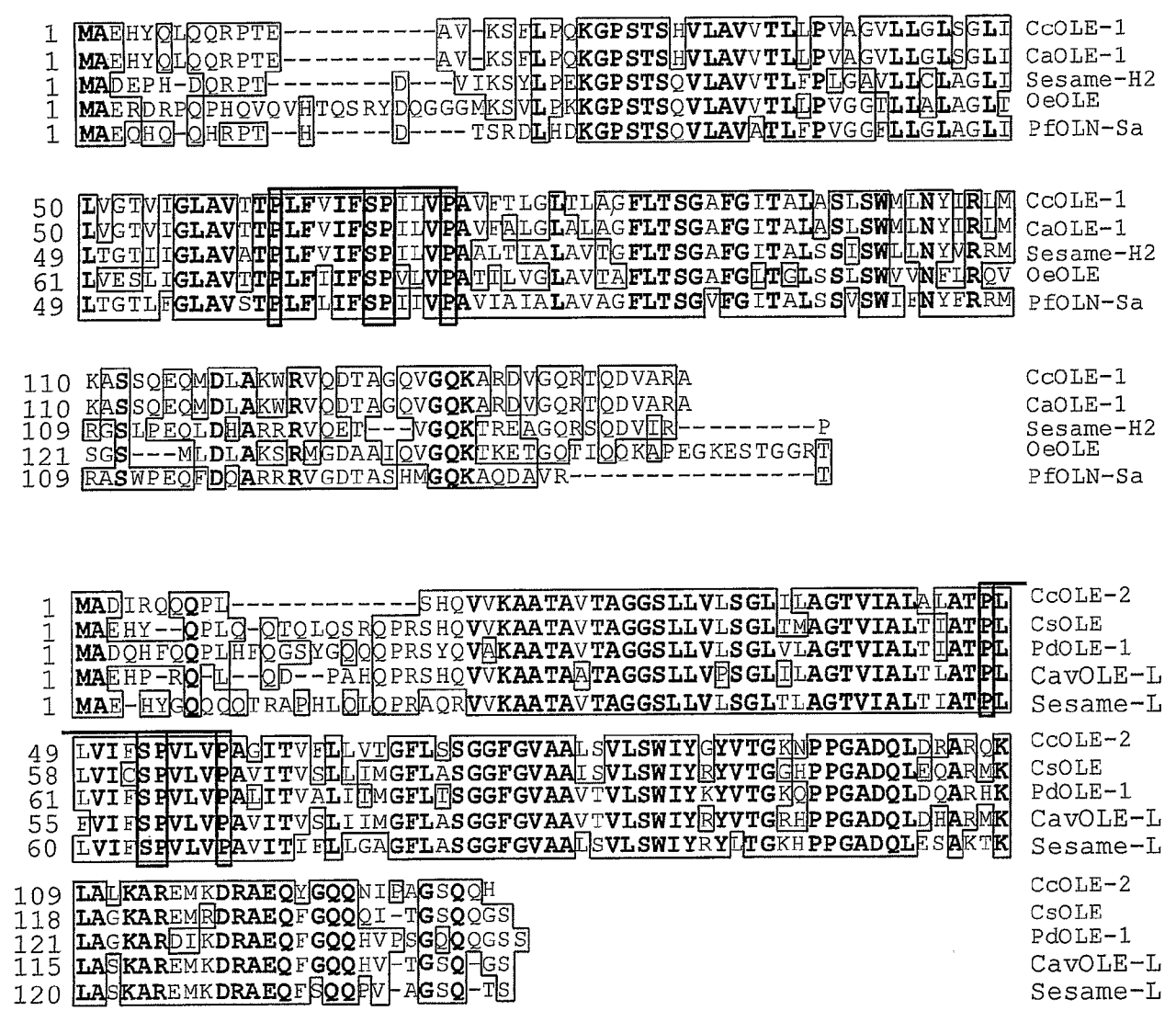
Figures 9C, 9D:
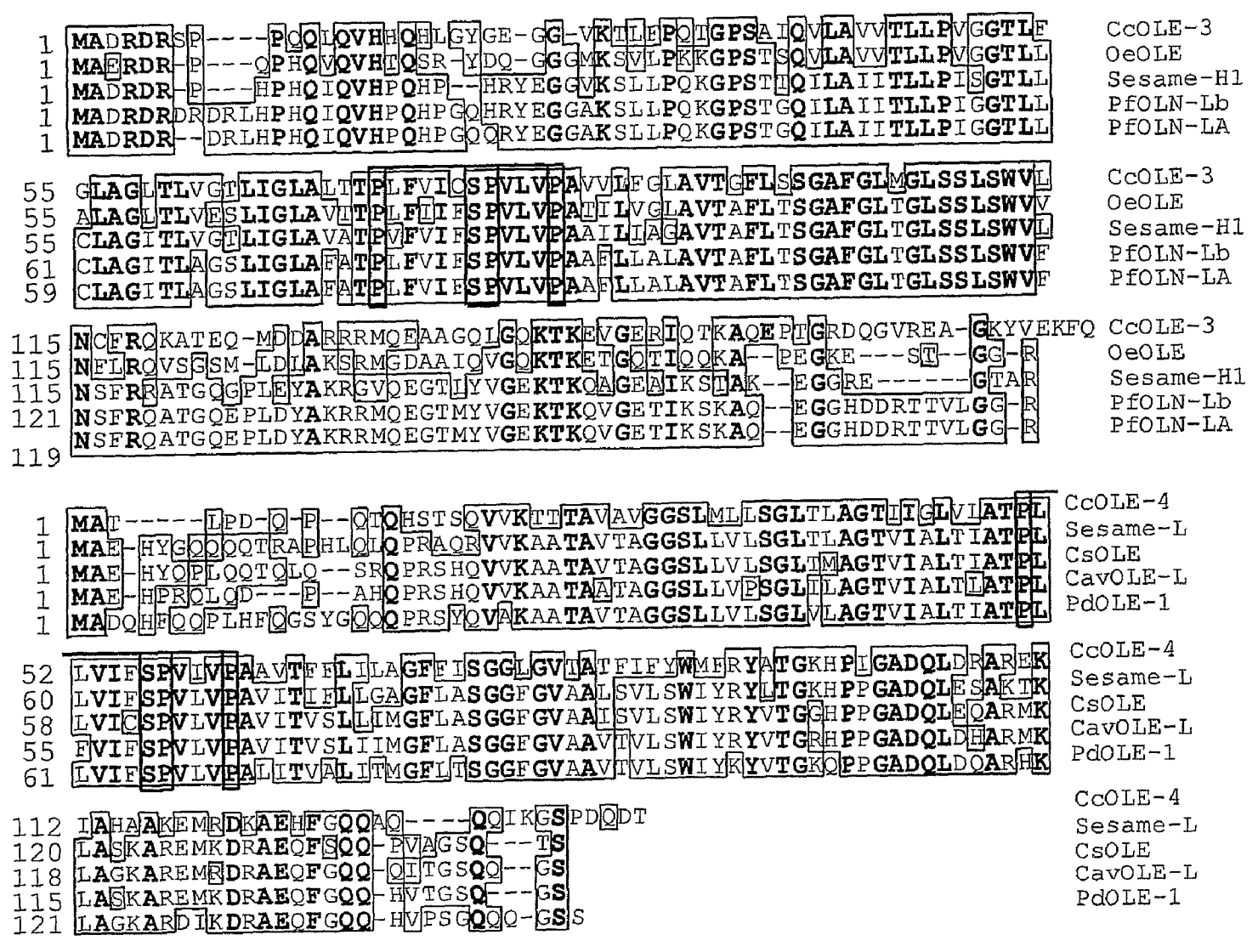

FIG. 9. Optimal alignment of each *Coffea canephora* protein sequence with the four closest databank sequences. FIG. 9A) CcOLE-1 (AY841271); FIG. 9B) CcOLE-2 (AY841272); FIG. 9C) CcOLE-3 (AY841273); FIG. 9D) CcOLE-4 (AY841274) and FIG. 9E) CcOLE-5 (AY841275). The alignments were generated with the clustal W program in the Lasergene software package (DNASTAR) and then adjusted manually to optimize the alignment. The location of the conserved P-(5X)-SP-(3X)-P proline knot motif is indicated with a line above and boxing of the conserved P and S residues. Conserved sequences are boxed; highly conserved regions are shown in bold. Accession numbers of the aligned oleosin sequences are: AAF69712 and BAB02215 for *Arabidopsis* Seed/Microspore 1 (SM1), and SM2 (Kim et al., 2002) (SEQ ID NOs. 41, 42, respectively); AY928084 for *Coffea arabica* (Ca) OLE-1 (SEQ ID NO.:1); AAO65960 for *Corylus avellana* (Cav) OLE-L (SEQ ID NO.:38); T10121 for *Citrus sinensis* OLE (SEQ ID NO.:36) (Naot et al., 1995); AAL92479 for *Olea europaea* OLE; Q43804 for *Prunus dulcis* for PdOLE-1 (SEQ ID NO.:37) (Garcia-Mas et al., 1995); AAG24455, AAG09751, AAG43516 and AAG43517 for *Perilla frutescens* OLN-Lb, OLN-La, and OLN-Sa (SEQ ID NOs.:39, 40, and 35, respectively); U97700 (Chen et al., 1997); AF302807 and AF091840 (Tai et al., 2002) for *Sesamum indicum* H2, H1 and L (SEQ ID NOs.:29-31, respectively).

Figure 10:
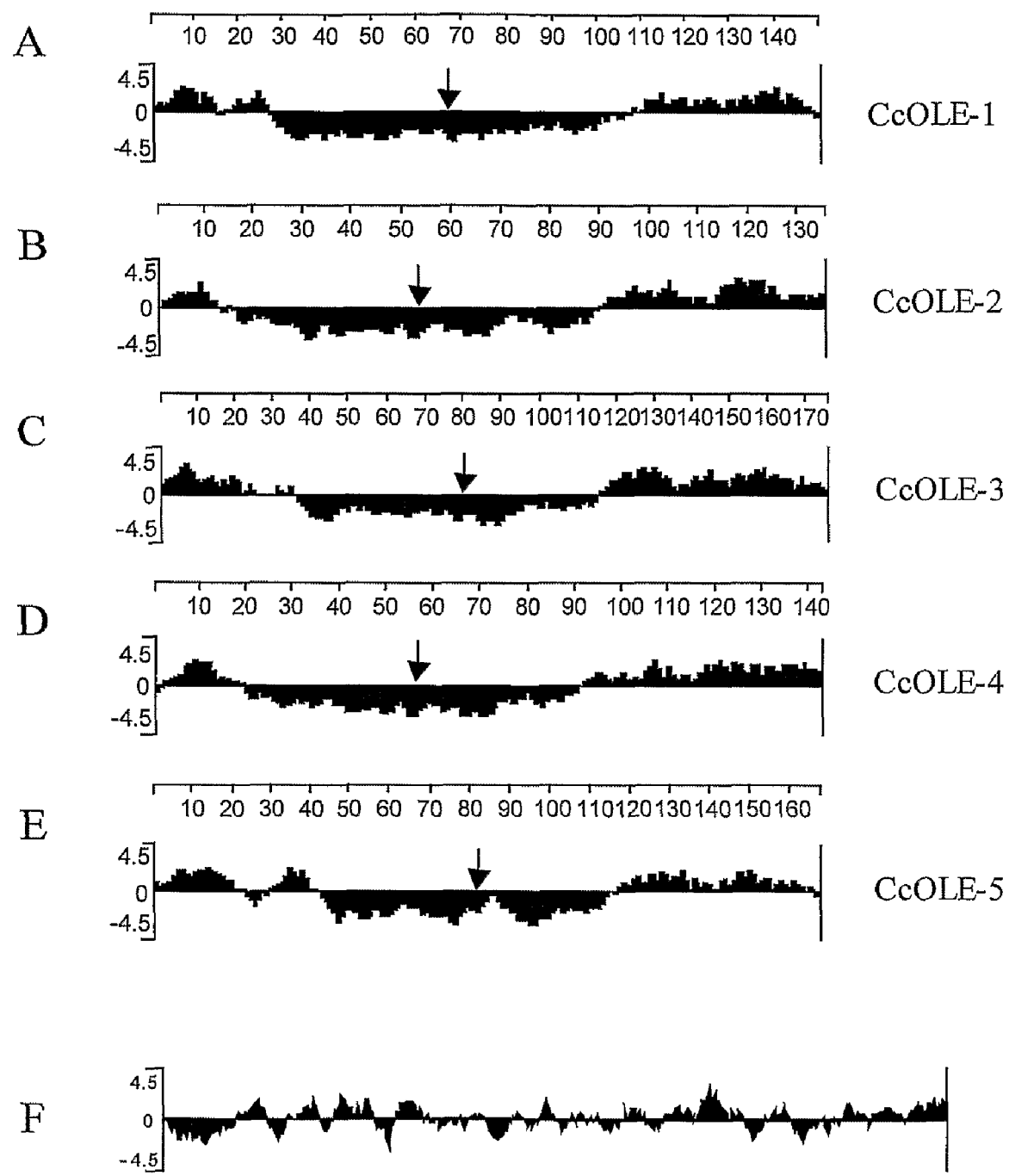

FIG. 10. Hydrophobicity profiles for the *C. canephora* oleosin family. The hydropathy plots were generated according to the method of Kyte and Doolittle (1982) using the appropriate program in the Lasergene software package (DNASTAR). Negative values indicate hydrophobic regions. The location of the proline knot motif is shown by an arrow. FIG. 10 (F) is a hydrophilicity plot.

Figure 11:
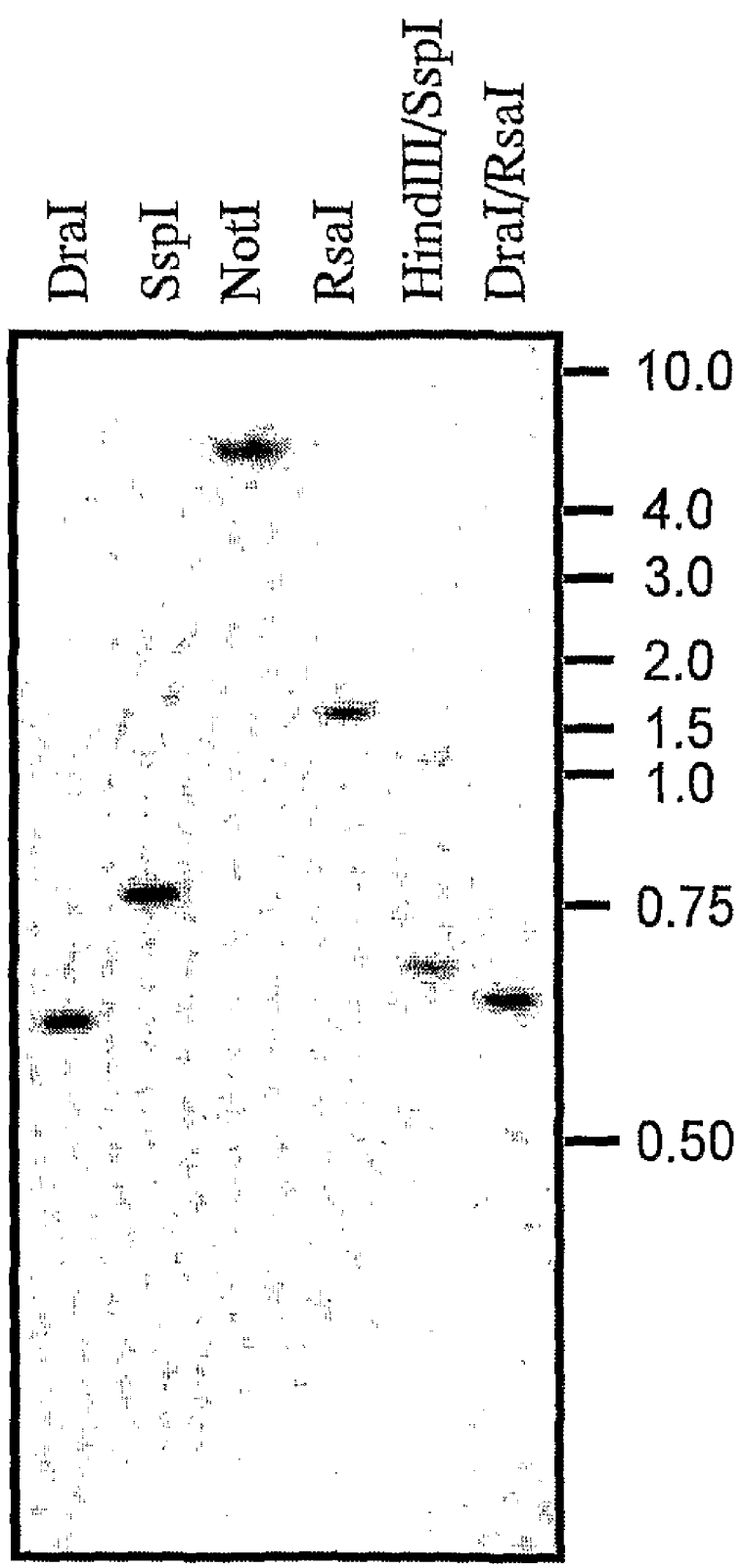

FIG. 11, Southern blot analysis of the CcOLE-1 gene. Evaluation of the copy number of OLE-1 in the genome of *C. canephora*. Genomic robusta DNA was cut with DraI, SspI, NotI, RsaI or HindIII/SspI and DraI/RsaI. Genomic blots were probed with the $p^{32}$ labelled full-length cDNA, including 3' and 5' untranslated region, for CcOLE-1. The autoradiograph presented was exposed for 10 days at −80° C.

Figure 12:
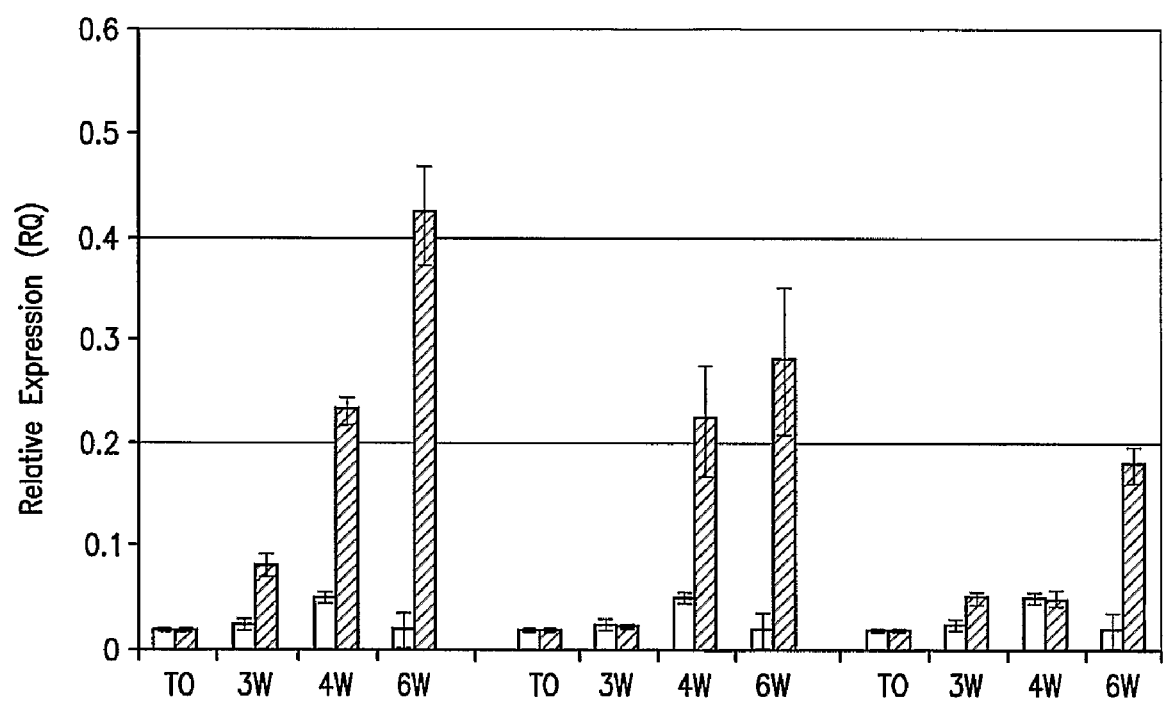

FIG. 12, Expression of OLE-1 in the leaves of *Coffea arabica* (catimor) under drought stress. Transcript levels for OLE-1 were determined by quantitative RT-PCR. The expression levels were determined relative to the expression of transcripts of the constitutively expressed rpl39 gene in the same samples. The unmarked bars in each case represent the mean transcript levels in three well-watered controls. Transcript levels in three independent water stressed plants are shown in hash-marked bars.

DETAILED DESCRIPTION OF ILLUSTRATIVE EMBODIMENTS

Definitions

Various terms relating to the biological molecules and other aspects of the present invention are used throughout the specification and claims.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

"Polynucleotide", also referred to as "nucleic acid molecule", generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W.H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., "Analysis for Protein Modifications and Nonprotein Cofactors", Meth Enzymol (1990) 182:626-646 and Rattan et al., "Protein Synthesis: Posttranslational Modifications and Aging", Ann NY Acad Sci (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions or deletions in any combination. A substituted or inserted amino acid residue may or may not be one encoded by the genetic code. A variant of a polynucleotide or polypeptide may be naturally occurring, such as an allelic variant, or it may be a variant that is not known to occur naturally. Non-naturally occurring variants of polynucleotides and polypeptides may be made by mutagenesis techniques or by direct synthesis.

In reference to mutant plants, the terms "null mutant" or "loss-of-function mutant" are used to designate an organism or genomic DNA sequence with a mutation that causes a gene product to be non-functional or largely absent. Such mutations may occur in the coding and/or regulatory regions of the gene, and may be changes of individual residues, or insertions or deletions of regions of nucleic acids. These mutations may also occur in the coding and/or regulatory regions of other genes, which themselves may regulate or control a gene and/or encoded protein, so as to cause the protein to be non-functional or largely absent.

The term "substantially the same" refers to nucleic acid or amino acid sequences having sequence variations that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those that differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

"Identity" and 'similarity' can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

"Antibodies" as used herein includes polyclonal and monoclonal antibodies, chimeric, single chain, and humanized antibodies, as well as antibody fragments (e.g., Fab, Fab', $F(ab')_2$ and $F_v$), including the products of a Fab or other immunoglobulin expression library. With respect to antibodies, the term, "immunologically specific" or "specific" refers to antibodies that bind to one or more epitopes of a protein of interest, but which do not substantially recognize and bind other molecules in a sample containing a mixed population of antigenic biological molecules. Screening assays to determine binding specificity of an antibody are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, and the like).

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, when the sequence is expressed. The coding sequence may comprise untranslated sequences (e.g., introns or 5' or 3' untranslated regions) within translated regions, or may lack such untranslated sequences (e.g., as in cDNA).

"Intron" refers to polynucleotide sequences in a nucleic acid that do not code information related to protein synthesis. Such sequences are transcribed into mRNA, but are removed before translation of the mRNA into a protein.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene". Such a nucleic acid construct may contain a coding sequence for a gene product of interest, along with a selectable marker gene and/or a reporter gene.

A "marker gene" or "selectable marker gene" is a gene whose encoded gene product confers a feature that enables a cell containing the gene to be selected from among cells not containing the gene. Vectors used for genetic engineering typically contain one or more selectable marker genes. Types of selectable marker genes include (1) antibiotic resistance genes, (2) herbicide tolerance or resistance genes, and (3) metabolic or auxotrophic marker genes that enable transformed cells to synthesize an essential component, usually an amino acid, which the cells cannot otherwise produce.

A "reporter gene" is also a type of marker gene. It typically encodes a gene product that is assayable or detectable by standard laboratory means (e.g., enzymatic activity, fluorescence).

The term "express," "expressed," or "expression" of a gene refers to the biosynthesis of a gene product. The process involves transcription of the gene into mRNA and then translation of the mRNA into one or more polypeptides, and encompasses all naturally occurring post-translational modifications.

"Endogenous" refers to any constituent, for example, a gene or nucleic acid, or polypeptide, that can be found naturally within the specified organism.

A "heterologous" region of a nucleic acid construct is an identifiable segment (or segments) of the nucleic acid molecule within a larger molecule that is not found in association with the larger molecule in nature. Thus, when the heterologous region comprises a gene, the gene will usually be flanked by DNA that does not flank the genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Grain," "seed," or "bean," refers to a flowering plant's unit of reproduction, capable of developing into another such plant. As used herein, especially with respect to coffee plants, the terms are used synonymously and interchangeably.

As used herein, the term "plant" includes reference to whole plants, plant organs (e.g., leaves, stems, shoots, roots), seeds, pollen, plant cells, plant cell organelles, and progeny thereof. Parts of transgenic plants are to be understood within the scope of the invention to comprise, for example, plant cells, protoplasts, tissues, callus, embryos as well as flowers, stems, seeds, pollen, fruits, leaves, or roots originating in transgenic plants or their progeny.

Description

In one of its aspects the present invention features nucleic acid molecules from coffee that encode a variety of oleosins, as well as a steroleosin. Representative examples of oleosin and steroleosin-encoding nucleic acid molecules were identified from databases of over 47,000 expressed sequence tags (ESTs) from several *Coffea canephora* (robusta) cDNA libraries made with RNA isolated from young leaves and from the grain and pericarp tissues of cherries harvested at different stages of development. Overlapping ESTs were identified and "clustered" into unigenes (contigs) comprising complete coding sequences. The unigene sequences were annotated by performing a BLAST search of each individual sequence against the NCBI (National Center for Biotechnology Information) non-redundant protein database. The open reading frames of five of the unigenes expressed during grain development were annotated as encoding glycine-rich proteins determined to be oleosins. A sixth open reading frame was identified by BLAST analysis of the databases with a known steroleosin sequence. ESTs representing full-length cDNA for each oleosin or steroleosin unigene were isolated and sequenced. A full length cDNA for one of the oleosins (OLE-1) was also isolated and sequenced). These cDNAs are referred to herein as CaOLE-1 (SEQ ID NO:1) and CcOLE-1 (SEQ ID NO.:2), CcOLE-2 (SEQ ID NO:3), CcOLE-3 (SEQ ID NO:4), CcOLE-4 (SEQ ID NO:5), CcOLE-5 (SEQ ID NO:6) and CcSTO-1 (SEQ ID NO:7). ESTs forming the oleosin or steroleosin unigenes were all from libraries obtained from grain at either 30 and 46 weeks post fertilization.

The deduced amino acid sequences of CaOLE-1 and CcOLE-1 to CcOLE-5, set forth herein as SEQ NOS: 8-13, have molecular masses 15.7, 14.1, 18.6, 15.3 and 17.9 kDa respectively. These proteins each contain a hydrophobic region of 81, 73, 80, 72 and 75 amino acids respectively with the signature KNOT motif containing three conserved prolines and one conserved serine at its center. The deduced amino acid sequence of Cc STO-1, set forth herein as SEQ ID NO:14, has a molecular mass of 40.5 kDa, with a proline KNOT motif within the N-terminal domain.

Close orthologs of the five coffee oleosins and the steroleosin have been identified in *Arabidopsis* and other plants with well-characterized oil bodies, such as such as sesame, rice and maize. Quantitative expression analysis indicates that there may be at least two types of expression patterns for the seed (S) and floral microspore (SM) type oleosins; one set of genes was found to have a higher level of expression at the beginning of oleosin gene expression, while the other set was found to exhibit higher expression slightly later in grain development. As evidenced by data set forth in greater detail in the examples, there appear to be significant differences in the levels and distribution of oleosin transcripts in two coffee species, *C. arabica* and *C. canephora* (robusta), with the higher oil-containing *C. arabica* grain having an overall higher level of oleosin transcripts relative to the expression of a constitutively expressed ribosomal protein. This observed variation in the overall level of oleosin proteins between two coffee species may provide a basis for manipulation of coffee, via genetic techniques or traditional breeding, to influence commercially important characteristics of coffee, such as oil content and profile, size and structure of oil bodies, formation of lipid derived volatiles, (E)-2-nonenal, and trans-trans-2-4-decadienal during coffee roasting, and the generation of "foam" during the extraction of espresso coffee.

Another aspect of the invention features promoter sequences and related elements that control expression of oleosin genes in coffee. As described in greater detail in the examples, a promoter sequence, pOLE-1 (contained in SEQ ID NO:15), from one of these genes was identified by PCR-assisted primer walking. The pOLE-1 promoter was shown to contain several seed specific regulatory elements, as shown in FIG. 8 and described in the examples. Using this promoter linked to the GUS reporter gene, it has been determined that this promoter is specific to seeds, cotyledons, hypocotyls and first true leaves of developing seedlings. Expression of the gene has also been shown to be induced by water stress.

Although polynucleotides encoding oleosins and steroleosin from *Coffea canephora* are described and exemplified herein, this invention is intended to encompass nucleic acids and encoded proteins from other *Coffea* species that are sufficiently similar to be used interchangeably with the *C. canephora* polynucleotides and proteins for the purposes described below. Accordingly, when the terms "oleosin" or "steroleosin" are used herein, they are intended to encompass all *Coffea* oleosins or steroleosins having the general physical, biochemical and functional features described herein, and polynucleotides encoding them.

Considered in terms of their sequences, oleosin- and steroleosin-encoding polynucleotides of the invention include allelic variants and natural mutants of SEQ ID NOs: 1-7, which are likely to be found in different varieties of *C. arabica* or *C. canephora*, and homologs of SEQ ID NOs: 1-7 likely to be found in different coffee species. Because such variants and homologs are expected to possess certain differences in nucleotide and amino acid sequence, this invention provides isolated oleosin- or steroleosin-encoding nucleic acid molecules that encode respective polypeptides having at least about 80% (and, with increasing order of preference, 81%, 82%, 83%, 84%, 85%, 86%, 87%, 88%, 89%, 90%, 91%, 92%, 93%, 94%, 95%, 96%, 97%, 98% and 99%) identity with any one of SEQ ID NOs:8-14, and comprises a nucleotide sequence having equivalent ranges of identity to any one of SEQ ID NOs: 1-7. Because of the natural sequence variation likely to exist among oleosins and steroleosins, and the genes encoding them in different coffee varieties and species, one skilled in the art would expect to find this level of variation, while still maintaining the unique properties of the polypeptides and polynucleotides of the present invention. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention.

Various domains or fragments of the coffee oleosin and steroleosin genes and proteins are also considered to be within the scope of the invention. For instance, the hydrophilic or amphipathic amino- and carboxy-terminal domains of the oleosin polypeptides, e.g., the N-terminal about 10-40 residues and the C-terminal about 30-50 residues, and the corresponding encoding polynucleotides may be used to distinguish one oleosin protein or oleosin-encoding gene from another. The conserved hydrophobic central domains and corresponding encoding polynucleotides may be useful for identifying oleosin orthologs from other species or genera. Likewise, the lesser-conserved portions of the steroleosin polypeptide (e.g., residues 1 to about 50, about 81 to about 102, and about 308 to the carboxy terminus) and corresponding encoding polynucleotides can distinguish closely related steroleosins from one another, while the conserved portions (e.g., residues 50 to about 80, and about 103 to about 307) may be used to identify less closely related orthologs.

The conserved hydrophobic central domains will find particular utility for targeting recombinant proteins to plant oil bodies, including coffee, as described in U.S. Pat. No. 6,137,032. Also as described in U.S. Pat. No. 6,137,032, association of recombinant proteins comprising a coffee oleosin hydrophobic domain with oil bodies (either natural or artificially constructed "oil body-like structures formed using, e.g., a vegetable oil) may be exploited to facilitate the purification of such recombinant proteins (van Rooijen & Moloney, 1995, Bio/Technology 13: 72-77).

As mentioned, the inventors have demonstrated that oleosin gene expression is seed and seedling specific in coffee, as well as being inducible by drought stress. Accordingly, the gene regulatory sequences associated with oleosin genes are of practical utility and are considered within the scope of the present invention. The *C. canephora* OLE-1 promoter is exemplified herein. The upstream region of the *C. canephora* OLE-1 genomic sequence is set forth herein as SEQ ID NO:15, and contains part or all of an exemplary promoter of the invention, though other portions of the promoter may be found at other locations in the gene, as explained in the definition of "promoter" set forth hereinabove. However, promoters and other gene regulatory sequences of oleosin and steroleosin genes from any coffee species may be obtained by the methods described below, and may be utilized in accordance with the present invention. The promoters and regulatory elements governing tissue specificity and temporal specificity of oleosin and steroleosin gene expression may be used to advantage to alter or modify the oil body profile of various coffee species, among other utilities.

The following sections set forth the general procedures involved in practicing the present invention. To the extent that specific materials are mentioned, it is merely for the purpose of illustration, and is not intended to limit the invention. Unless otherwise specified, general biochemical and molecular biological procedures, such as those set forth in Sambrook et al., Molecular Cloning, Cold Spring Harbor Laboratory (1989) or Ausubel et al. (eds), Current Protocols in Molecular Biology, John Wiley & Sons (2005) are used.

Nucleic Acid Molecules, Proteins and Antibodies:

Nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA having SEQ ID NOs: 1-7 or the regulatory sequence of SEQ ID NO:15, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

In accordance with the present invention, nucleic acids having the appropriate level sequence homology with part or all of the coding and/or regulatory regions of oleosin- or steroleosin-encoding polynucleotides may be identified by using hybridization and washing conditions of appropriate stringency. It will be appreciated by those skilled in the art that the aforementioned strategy, when applied to genomic sequences, will, in addition to enabling isolation of oleosin or steroleosin coding sequences, also enable isolation of promoters and other gene regulatory sequences associated with oleosin or steroleosin genes, even though the regulatory sequences themselves may not share sufficient homology to enable suitable hybridization.

As a typical illustration, hybridizations may be performed, according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45-55° C. in 2×SSC and 0.1% SDS, changing the solution every 30 minutes.

One common formula for calculating the stringency conditions required to achieve hybridization between nucleic acid molecules of a specified sequence homology (Sambrook et al., 19S9):

$$Tm=81.5° C.+16.6 \text{ Log }[Na+]+0.41 (\% G+C)-0.63$$
$$(\% \text{ formamide})-600/\text{\#bp in duplex}$$

As an illustration of the above formula, using [Na+]= [0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. In one embodiment, the hybridization is at 37° C. and the final wash is at 42° C.; in another embodiment the hybridization is at 42° C. and the final wash is at 50° C.; and in yet another embodiment the hybridization is at 42° C. and final wash is at 65° C., with the above hybridization and wash solutions. Conditions of high stringency include hybridization at 42° C. in the above hybridization solution and a final wash at 65° C. in 0.1×SSC and 0.1% SDS for 10 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.), pBluescript (Stratagene, La Jolla, Calif.), pCR4—TOPO (Invitrogen, Carlsbad, Calif.) or pET28a+ (Novagen, Madison, Wis.), all of which can be propagated in a suitable *E. coli* host cell.

Nucleic acid molecules of the invention include cDNA, genomic DNA, RNA, and fragments thereof which may be single-, double-, or even triple-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting oleosin or steroleosin-encoding genes or mRNA in test samples of plant tissue, e.g. by PCR amplification, or for the positive or negative regulation of expression of oleosin- or steroleosin-encoding genes at or before translation of the mRNA into proteins. Methods in which oleosin- or steroleosin-encoding oligonucleotides or polynucleotides may be utilized as probes for such assays include, but are not limited to: (1) in situ hybridization; (2) Southern hybridization (3) northern hybridization; and (4) assorted amplification reactions such as polymerase chain reactions (PCR) (including RT-PCR) and ligase chain reaction (LCR).

Polypeptides encoded by nucleic acids of the invention may be prepared in a variety of ways, according to known methods. If produced in situ the polypeptides may be purified from appropriate sources, e.g., seeds, pericarps, or other plant parts.

Alternatively, the availability of isolated nucleic acid molecules encoding the polypeptides enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis., BRL, Rockville, Md. or Invitrogen, Carlsbad, Calif.

According to a preferred embodiment, larger quantities of oleosin or steroleosin polypeptides may be produced by expression in a suitable procaryotic or eucaryotic system. For example, part or all of a DNA molecule, such as the cDNAs having SEQ ID NOs: 1-7, may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The oleosins or steroleosins produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The oleosins and steroleosins of the invention, prepared by the aforementioned methods, may be analyzed according to standard procedures.

Oleosins and steroleosins purified from coffee or recombinantly produced, may be used to generate polyclonal or monoclonal antibodies, antibody fragments or derivatives as defined herein, according to known methods. In addition to making antibodies to the entire recombinant protein, if analyses of the proteins or Southern and cloning analyses (see below) indicate that the cloned genes belongs to a multigene family, then member-specific antibodies made to synthetic peptides corresponding to nonconserved regions, e.g., the N- or C-terminal regions, of the protein can be generated.

Kits comprising an antibody of the invention for any of the purposes described herein are also included within the scope of the invention. In general, such a kit includes a control antigen for which the antibody is immunospecific.

Oleosins and steroleosins purified from coffee or recombinantly produced may also be used as emulsifiers or, making use of their inherent ability to stabilize small oil droplets within cells of coffee beans, they may be used as encapsulating agents for oil-soluble molecules. Utilizing these properties, coffee oleosins and steroleosins will find practical utility in the food industry for preparing standard food emulsions, including but not limited to cheese, yogurt, ice cream, margarine, mayonnaise, salad dressing or baking products. They will also be useful in the cosmetic industry for producing soaps, skin creams toothpastes, lipstick and face make-up, and the like.

Vectors, Cells, Tissues and Plants:

Also featured in accordance with the present invention are vectors and kits for producing transgenic host cells that contain an oleosin- or steroleosin-encoding polynucleotide or oligonucleotide, or homolog, analog or variant thereof in a sense or antisense orientation, or reporter gene and other constructs under control of oleosin or steroleosin promoters and other regulatory sequences. Suitable host cells include, but are not limited to, plant cells, bacterial cells, yeast and other fungal cells, insect cells and mammalian cells. Vectors for transforming a wide variety of these host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. Typically, kits for producing transgenic host cells will contain one or more appropriate vectors and instructions for producing the transgenic cells using the vector. Kits may further include one or more additional components, such as culture media for culturing the cells, reagents for performing transformation of the cells and reagents for testing the transgenic cells for gene expression, to name a few.

The present invention includes transgenic plants comprising one or more copies of an oleosin or steroleosin-encoding gene, or nucleic acid sequences that inhibit the production or function of a plant's endogenous oleosins or steroleosins. This is accomplished by transforming plant cells with a transgene that comprises part of all of an oleosin or steroleosin coding sequence, or mutant, antisense or valiant thereof, including RNA, controlled by either native or recombinant regulatory sequences, as described below. Coffee species are presently preferred for making the transgenic plants described herein, including, without limitation, *C. abeokutae, C. arabica, C. arnoldiana, C. aruwemiensis, C. bengalensis, C. canephora, C. congensis C. dewevrei, C. excelsa, C. eugenioides*, and *C. heterocalyx, C. kapakata, C. khasiana, C. liberica, C. moloundou, C. rasemosa, C. salvatrix, C. sessiflora, C. stenophylla, C. travencorensis, C. wightiana* and *C. zanguebariae*. Plants of any species are also included in the invention; these include, but are not limited to, tobacco, *Arabidopsis* and other "laboratory-friendly" species, cereal crops such as maize, wheat, rice, soybean barley, rye, oats, sorghum, alfalfa, clover and the like, oil-producing plants such as canola, safflower, sunflower, peanut, cacao and the like, vegetable crops such as tomato tomatillo, potato, pepper, eggplant, sugar beet, carrot, cucumber, lettuce, pea and the like, horticultural plants such as aster, begonia, chrysanthemum, delphinium, petunia, zinnia, lawn and turfgrasses and the like.

Transgenic plants can be generated using standard plant transformation methods known to those skilled in the art. These include, but are not limited to, *Agrobacterium* vectors, polyethylene glycol treatment of protoplasts, biolistic DNA delivery, UV laser microbeam, gemini virus vectors or other plant viral vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., Methods for Plant Molecular Biology (Weissbach & Weissbach, eds., 1988); Methods in Plant Molecular Biology (Schuler & Zielinski, eds., 1989); Plant Molecular Biology Manual (Gelvin, Schilperoort, Verma, eds., 1993); and Methods in Plant Molecular Biology—A Laboratory Manual (Maliga, Klessig, Cashmore, Gruissem & Varner, eds., 1994).

The method of transformation depends upon the plant to be transformed. *Agrobacterium* vectors are often used to transform dicot species. *Agrobacterium* binary vectors include, but are not limited to, BIN19 and derivatives thereof, the pBI vector series, and binary vectors pGA482, pGA492, pLH7000 (GenBank Accession AY234330) and any suitable one of the pCAMBIA vectors (derived from the pPZP vectors constructed by Hajdukiewicz, Svab & Maliga, (1994) Plant Mol Biol 25: 989-994, available from CAMBIA, GPO Box 3200, Canberra ACT 2601, Australia or via the worldwide web at CAMBIA.org). For transformation of monocot species, biolistic bombardment with particles coated with transforming DNA and silicon fibers coated with transforming DNA are often useful for nuclear transformation. Alternatively, *Agrobacterium* "superbinary" vectors have been used successfully for the transformation of rice, maize and various other monocot species.

DNA constructs for transforming a selected plant comprise a coding sequence of interest operably linked to appropriate 5' regulatory sequences (e.g., promoters and translational regulatory sequences) and 3' regulatory sequences (e.g., terminators). In a preferred embodiment, an oleosin or steroleosin coding sequence under control of its natural 5' and 3' regulatory elements is utilized. In other embodiments, oleosin- and steroleosin coding and regulatory sequences are swapped (e.g., Cc OLE-1 coding sequence operably linked to CcOLE-2 promoter) to alter the seed oil profile of the transformed plant for a phenotypic improvement, e.g., in flavor, aroma or other feature.

In an alternative embodiment, the coding region of the gene is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase and octopine synthase promoters. In other embodiments, a strong monocot promoter is used, for example, the maize ubiquitin promoter, the rice actin promoter or the rice tubulin promoter (Jeon et al., Plant Physiology. 123: 1005-14, 2000).

Transgenic plants expressing oleosin or steroleosin coding sequences under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g. hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name a few.

Tissue specific and development-specific promoters are also contemplated for use in the present invention, in addition to the seed-specific oleosin promoters of the invention. Non-limiting examples of other seed-specific promoters include Cim1 (cytokinin-induced message), cZ19B1 (maize 19 kDa zein), milps (myo-inositol-1-phosphate synthase), and celA (cellulose synthase) (U.S. application Ser. No. 09/377,648), bean beta-phaseolin, napin beta-conglycinin, soybean lectin, cruciferin, maize 15 kDa zein, 22 kDa zein, 27 kDa zein, g-zein, waxy, shrunken 1, shrunken 2, and globulin 1, soybean 11S legumin (Bäumlein et al., 1992), and *C. canephora* 11S seed storage protein (Marraccini et al., 1999, Plant Physiol. Biochem. 37: 273-282). See also WO 00/12733, where seed-preferred promoters from end1 and end2 genes are disclosed. Other *Coffea* seed specific promoters may also be utilized, including but not limited to the dehyrdin gene promoter described in commonly-owned, co-pending U.S. Provisional Patent Application No. 60/696,890. Examples of other tissue-specific promoters include, but are not limited to: the ribulose bisphosphate carboxylase (RuBisCo) small subunit gene promoters (e.g., the coffee small subunit promoter as described by Marracini et al., 2003) or chlorophyll a/b binding protein (CAB) gene promoters for expression in photosynthetic tissue; and the root-specific glutamine synthetase gene promoters where expression in roots is desired.

The coding region is also operably linked to an appropriate 3' regulatory sequence. In embodiments where the native 3' regulatory sequence is not use, the nopaline synthetase polyadenylation region may be used. Other useful 3' regulatory regions include, but are not limited to the octopine synthase polyadenylation region.

The selected coding region, under control of appropriate regulatory elements, is operably linked to a nuclear drug resistance marker, such as kanamycin resistance. Other useful selectable marker systems include genes that confer antibiotic or herbicide resistances (e.g., resistance to hygromycin, sulfonylurea, phosphinothricin, or glyphosate) or genes conferring selective growth (e.g., phosphomannose isomerase, enabling growth of plant cells on mannose). Selectable marker genes include, without limitation, genes encoding antibiotic resistance, such as those encoding neomycin phosphotransferase II (NEO), dihydrofolate reductase (DHFR) and hygromycin phosphotransferase (HPT), as well as genes that confer resistance to herbicidal compounds, such as glyphosate-resistant EPSPS and/or glyphosate oxidoreductase (GOX), *Bromoxynil nitrilase* (BXN) for resistance to bromoxynil, AHAS genes for resistance to imidazolinones, sulfonylurea resistance genes, and 2,4-dichlorophenoxyacetate (2,4-D) resistance genes.

In certain embodiments, promoters and other expression regulatory sequences encompassed by the present invention are operably linked to reporter genes. Reporter genes contemplated for use in the invention include, but are not limited to, genes encoding green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), β-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B- phosphotransferase (HPH), thymidine kinase (TK), lacZ (encoding α-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). As with many of the standard procedures associated with the practice of the invention, skilled artisans will be aware of additional sequences that can serve the function of a marker or reporter.

Additional sequence modifications are known in the art to enhance gene expression in a cellular host. These modifications include elimination of sequences encoding superfluous polyadenylation signals, exon-intron splice site signals, transposon-like repeats, and other such well-characterized sequences that may be deleterious to gene expression. Alternatively, if necessary, the G/C content of the coding sequence may be adjusted to levels average for a given coffee plant cell host, as calculated by reference to known genes expressed in a coffee plant cell. Also, when possible, the coding sequence is modified to avoid predicted hairpin secondary mRNA structures. Another alternative to enhance gene expression is to use 5' leader sequences. Translation leader sequences are well known in the art, and include the cis-acting derivative (omega') of the 5' leader sequence (omega) of the tobacco mosaic virus, the 5' leader sequences from brome mosaic virus, alfalfa mosaic virus, and turnip yellow mosaic virus.

Plants are transformed and thereafter screened for one or more properties, including the presence of the transgene product, the transgene-encoding mRNA, or an altered phenotype associated with expression of the transgene. It should be recognized that the amount of expression, as well as the tissue- and temporal-specific pattern of expression of the transgenes in transformed plants can vary depending on the position of their insertion into the nuclear genome. Such positional effects are well known in the art. For this reason, several nuclear transformants should be regenerated and tested for expression of the transgene.

Methods:

The nucleic acids and polypeptides of the present invention can be used in any one of a number of methods whereby the protein products can be produced in coffee plants in order that the proteins may play a role in the enhancement of the flavor and/or aroma of the coffee beverage or coffee products ultimately produced from the bean of the coffee plant expressing the protein.

In one aspect, the present invention features methods to alter the oleosin or steroleosin profile in a plant, preferably coffee, comprising increasing or decreasing an amount or activity of one or more oleosins or steroleosins in the plant. For instance, in one embodiment of the invention, an oleosin-encoding gene under control of its own expression-controlling sequences is used to transform a plant for the purpose of increasing production of that oleosin in the plant. Alternatively, an oleosin or steroleosin coding region is operably linked to heterologous expression controlling regions, such as constitutive or inducible promoters.

The oil body profile of a plant may also be altered by decreasing production of one or more oleosins or steroleosin in the plant, or by screening naturally-occurring variants for decreased oleosin or steroleosin expression. For instance, loss-of-function (null) mutant plants may be created or selected from populations of plant mutants currently available. It will also be appreciated by those of skill in the art that mutant plant populations may also be screened for mutants that over-express a particular oleosin, utilizing one or more of the methods described herein. Mutant populations can be made by chemical mutagenesis, radiation mutagenesis, and transposon or T-DNA insertions, or targeting induced local lesions in genomes (TILLING, see, e.g., Henikoff et al., 2004, Plant Physiol. 135(2): 630-636; Gilchrist & Haughn, 2005, Curr. Opin. Plant Biol. 8(2): 211-215). The methods to make mutant populations are well known in the art.

The nucleic acids of the invention can be used to identify oleosin or steroleosin mutants in various plant species. In species such as maize or *Arabidopsis*, where transposon insertion lines are available, oligonucleotide primers can be designed to screen lines for insertions in the oleosin or steroleosin genes. Through breeding, a plant line may then be developed that is heterozygous or homozygous for the interrupted gene.

A plant also may be engineered to display a phenotype similar to that seen in null mutants created by mutagenic techniques. A transgenic null mutant can be created by a expressing a mutant form of a selected oleosin or steroleosin protein to create a "dominant negative effect." While not limiting the invention to any one mechanism, this mutant protein will compete with wild-type protein for interacting proteins or other cellular factors. Examples of this type of "dominant negative" effect are well known for both insect and vertebrate systems (Radke et al., 1997, Genetics 145: 163-171; Kolch et al., 1991, Nature 349: 426-428).

Another kind of transgenic null mutant can be created by inhibiting the translation of oleosin- or steroleosin-encoding mRNA by "post-transcriptional gene silencing." The oleosin- or steroleosin-encoding gene from the species targeted for down-regulation, or a fragment thereof, may be utilized to control the production of the encoded protein. Full-length antisense molecules can be used for this purpose. Alternatively, antisense oligonucleotides targeted to specific regions of the mRNA that are critical for translation may be utilized. The use of antisense molecules to decrease expression levels of a pre-determined gene is known in the art. Antisense molecules may be provided iii situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al., 1998, PNAS 95: 13959-13964). In this regard, dsRNA containing sequences that correspond to part or all of at least one intron have been found particularly effective. In one embodiment, part or all of the oleosin or steroleosin coding sequence antisense strand is expressed by a transgene. In another embodiment, hybridizing sense and antisense strands of part or all of the oleosin or steroleosin coding sequence are transgenically expressed.

In another embodiment, oleosin and steroleosin genes may be silenced through the use of a variety of other post-transcriptional gene silencing (RNA silencing) techniques that are currently available for plant systems. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner (for reviews of RNA silencing in plants, see Horiguchi, 2004, *Differentiation* 72: 65-73; Baulcombe, 2004, Nature 431: 356-363; Herr, 2004, *Biochem. Soc. Trans.* 32: 946-951).

Small interfering RNAs may be chemically synthesized or transcribed and amplified in vitro, and then delivered to the cells. Delivery may be through microinjection (Tuschl T et al., 2002), chemical transfection (Agrawal N et al., 2003), electroporation or cationic liposome-mediated transfection (Brummelkamp T R et al., 2002; Elbashir S M et al., 2002), or any other means available in the art, which will be appreciated by the skilled artisan. Alternatively, the siRNA may be expressed intracellularly by inserting DNA templates for siRNA into the cells of interest, for example, by means of a plasmid, (Tuschl T et al., 2002), and may be specifically targeted to select cells. Small interfering RNAs have been successfully introduced into plants. (Kilahre U et al., 2002).

A preferred method of RNA silencing in the present invention is the use of short hairpin RNAs (shRNA). A vector containing a DNA sequence encoding for a particular desired siRNA sequence is delivered into a target cell by any common means. Once in the cell, the DNA sequence is continuously transcribed into RNA molecules that loop back on themselves and form hairpin structures through intramolecular base pairing. These hairpin structures, once processed by the cell, are equivalent to siRNA molecules and are used by the cell to mediate RNA silencing of the desired protein. Various constructs of particular utility for RNA silencing in plants are described by Horiguchi, 2004, supra. Typically, such a construct comprises a promoter, a sequence of the target gene to be silenced in the "sense" orientation, a spacer, the antisense of the target gene sequence, and a terminator.

Yet another type of synthetic null mutant can also be created by the technique of "co-suppression" (Vaucheret et al., 1998, Plant J. 16(6): 651-659). Plant cells are transformed with a full sense copy or a partial sense sequence of the endogenous gene targeted for repression. In many cases, this results in the complete repression of the native gene as well as the transgene. In one embodiment, an oleosin- or steroleosin-encoding gene from the plant species of interest is isolated and used to transform cells of that same species.

Mutant or transgenic plants produced by any of the foregoing methods are also featured in accordance with the present invention. In some embodiments, such plants will be of utility as research tools for the further elucidation of the participation of oleosins and steroleosins in flavor, aroma and other features of coffee seeds associated with oil profiles. Preferably, the plants are fertile, thereby being useful for breeding purposes. Thus, mutant or plants that exhibit one or more of the aforementioned desirable phenotypes can be used for plant breeding, or directly in agricultural or horticultural applications. Plants containing one transgene or a specified mutation may also be crossed with plants containing a complementary transgene or genotype in order to produce plants with enhanced or combined phenotypes.

Coffee plants produced in accordance with the above-described methods are of practical utility for the production of coffee beans with enhanced flavor, aroma or other features as discussed above. Typically, the beans are roasted and ground for drinking. However, other uses for the beans will be apparent to those of skill in the art. For instance, oil bodies may be harvested from the beans (uncooked or lightly roasted), in accordance with known methods. For example, oil bodies of different levels of purity can be purified as described in Guilloteau et al. 2003, Plant Science 164: 597-606, or for example as disclosed in U.S. Pat. No. 6,146,645 to Deckers et al and EP 0883997 to Wakabayashi et al. Similar to the isolated oleosin proteins described above, these oil bodies may be used in the food industry for adding flavor and nutrition, e.g., to baking products, yogurt or ice cream (e.g., U.S. Published Application No. 2005/0037111 A1 to Berry et al.) and the like, or in the cosmetic industry for producing soaps, skin creams, make-up, and the like.

The present invention also features compositions and methods for producing, in a seed-preferred or seed-specific manner, any selected heterologous gene product in a plant. A coding sequence of interest is placed under control of a coffee oleosin or other seed-specific promoter and other appropriate regulatory sequences, to produce a seed-specific chimeric gene. The chimeric gene is introduced into a plant cell by any of the transformation methods described herein or known in the art. These chimeric genes and methods may be used to produce a variety of gene products of interest in the plant, including but not limited to: (1) detectable gene products such as GFP or GUS, as enumerated above; (2) gene products conferring an agronomic or horticultural benefit, such as those whose enzyme activities result in production of micronutrients (e.g., pro-vitamin A, also known as beta-carotene) or antioxidants (e.g., ascorbic acid, omega fatty acids, lycopene, isoprenes, terpenes); or (3) gene products for controlling pathogens or pests, such as described by Mourgues et al., (1998), TibTech 16: 203-210 or others known to be protective to plant seeds or detrimental to pathogens.

Additionally, because expression of oleosin genes, such as the CcOle-1 gene, is also induced under drought conditions, oleosin gene promoters may also prove useful to direct gene expression in other tissues, such as mature leaves, when they are severely osmotically stressed. For instance, these promoters can be used to express recombinant proteins specifically in the leaves of plants (for example tobacco) at the end of maturation as they undergo senescence and begin to dry.

The following examples are provided to illustrate the invention in greater detail. The examples are for illustrative purposes, and are not intended to limit the invention.

Example 1

Plant Material for RNA Extraction

Freshly harvested roots, young leaves, stems, flowers and fruit at different stages of development were harvested from *Coffea arabica* L. cv. Catturra T-2308 grown under greenhouse conditions (25° C., 70% RH) and from *Coffea canephora* (robusta) BP-409 grown in the field in Indonesia. The development stages are defined as follows: small green fruit (SG), large green fruit (LG), yellow fruit (Y) and red fruit (R). Fresh tissues were frozen immediately in liquid nitrogen, then stored at −80° C. until used for RNA extraction.

Example 2

Extraction of Total RNA and Generation of cDNA

Samples stored at −80° C. were ground into a powder and total RNA was extracted from this powder using the method described by Gilloteau et al., 2003. Samples were treated with DNase using the kit "Qiagen RNase-Free DNase" according to the manufacturer's instructions to remove DNA contamination. All RNA samples were analysed by formaldehyde agarose gel electrophoresis and visual inspection of the ribosomal RNA bands upon ethidium bromide staining. Using oligo $(dT_{20})$ as a primer, cDNA was prepared from approximately 4 μg total RNA according to the protocol in the Superscript II Reverse Transcriptase kit (Invitrogen, Carlsbad, Calif.). To test for the presence of contaminating genomic DNA in the cDNA preparations, a primer pair was designed spanning a known intron of a specific ubiquitously expressed cDNA, chalcone isomerase (CHI). RT-PCR was carried out using 10-fold dilution of cDNA corresponding to 0.1 μg of original RNA. Conventional-PCR reactions contained 1× buffer and 5 mM $MgCl_2$, 200 µM each of dATP, dCTP, dGTP and dTTP, and 1 unit of polymerase, and 800 nM of each the gene specific primers—FWD-CCCACCTGGAGCCTCTAT-TCTGTT (SEQ ID NO.:83) and REV-CCCCGTCGGCCT-CAAGTTTC (SEQ ID NO.:84) for 35 cycles. An expected, a cDNA band of 272 bp was observed following PCR. A second band corresponding to the cDNA+intron at 750 bp was not observed, indicating an absence of genomic DNA in the samples (data not shown).

Conventional PCR reactions for the genes of interest were carried out using a 100-fold dilution of cDNA corresponding to 0.01 g of original RNA. PCR was carried out using 800 nM of each gene specific primers CcOLE-1 (FWD-TTCGT-TATCTTTAGCCCCATTT; REV-CATAGGCAAGATTAA-CAAGGAT$^{353}$) (SEQ ID NOs.: 43, 44, respectively), CcOLE-2 (FWD-GTGGCAGCGTTGAGCGT; REV-GA-CAATAATGCATGAATACCACAA$^{309}$) (SEQ ID NOs.: 45, 46, respectively), CcOLE-3 (FWD-GAGATCAAGGTG-GAAGGGAA; REV-GAAAACCCTCAACAAACAAA GA;$^{228}$) (SEQ ID NOs.: 47, 48, respectively), CcOLE-4 (FWD-CTGACACTGGCTGGAACAATA; REV-GCA-CAACATTCCATCAAGTATCT$^{337}$) ((SEQ ID NOs.: 49, 50, respectively), and CcOLE-5 (FWD-TGGCATCCTACT-TCTCCTCACT; REV-CTCTCTAGCATAATCCTTCAC-CTG$^{295}$) (SEQ ID NOs.: 51, 52, respectively). Amplification of the RPL39 gene (FWD-TGGCGAAGAAGCAGAG-GCAGA; REV-TTGAGGGGGAGGGTAAAAAG$^{187}$) (SEQ ID NOs.: 53, 54, respectively) was used as a positive control for the reverse transcription. Samples were electrophoresed on a 1.5% agarose gel. The superscript numbers with each primer set indicate the size of the amplicon.

Quantitative TaqMan-PCR was carried out with cDNA described above and using the protocol recommended by the manufacturer (Applied Biosystems, Perkin-Elmer). All reactions contained 1× TaqMan buffer (Perkin-Elmer) and 5 mM $MgCl_2$, 200 µM each of dATP, dCTP, dGTP and dTTP, and 0.625 units of AmpliTaq Gold polymerase. PCR was carried out using 800 nM of each of the gene-specific primers, forward and reverse, 200 nM TaqMan probe, and 1000-fold dilution of cDNA corresponding to 0.001 µg of original RNA. Primers and probes were designed using PRIMER EXPRESS software (Applied Biosystems: see Table 3 below). The cross specificity of the primers and probes is summarized in Table 4 below. The reaction mixture was incubated for 2 min at 50° C., then 10 min at 95° C., followed by 40 amplification cycles of 15 sec at 95° C./1 min at 60° C. Samples were quantified in the GeneAmp 7500 Sequence Detection System (Applied Biosystems). Transcript levels were normalized to the levels of the control gene, rpl39.

Example 3

Promoter Isolation and Vector Construction

The 5' upstream region of OLE-1 from *Coffea canephora* was recovered using the Genewalker kit (BD Biosciences) and the primers OLE-IA (5'-AAGTTGATGGACCCTTCT-GAGGAAGG-3') (SEQ ID NO.:55) followed by nested PCR using primer OLE-1B (5'-AGCTGGTAGTGCTCAGCCAT-GAAGG-3') (SEQ ID NO.:56). PCR reactions contained 1× buffer and 5 mM $MgCl_2$, 200 µM each of dATP, dCTP, dGTP and dTTP, and 1 unit of LA Taq polymerase (Takara, Combrex Bio, Belgium) with 200 nM primer OLE-1A and 200 nM primer AP1 (Genewalker kit). The reaction mixture was incubated for 10 min at 94° C., followed by 7 amplification cycles of 25 sec at 94° C./4 min at 72° C. and then 32 amplification cycles of 25 sec at 94° C./4 min at 67° C. The PCR reaction was diluted 1/200 and the used for a second PCR reaction using 200 nM of nested primer OLE-LB and 200 nM of nested primer AP2. Nested PCR was incubated for 10 min at 94° C., followed by 5 amplification cycles of 25 sec at 94° C./4 min at 72° C. and then 22 amplification cycles of 25 sec at 94° C./4 min at 67° C. A 1075 bp genomic fragment was recovered and cloned into the pCR4-TOPO vector (Invitrogen) to make pCR4-pOLE1 and the insert of this plasmid was sequenced.

Example 4

Isolation and Identification of Oleosin Genes from Developing Coffee Grain

Figure 1:
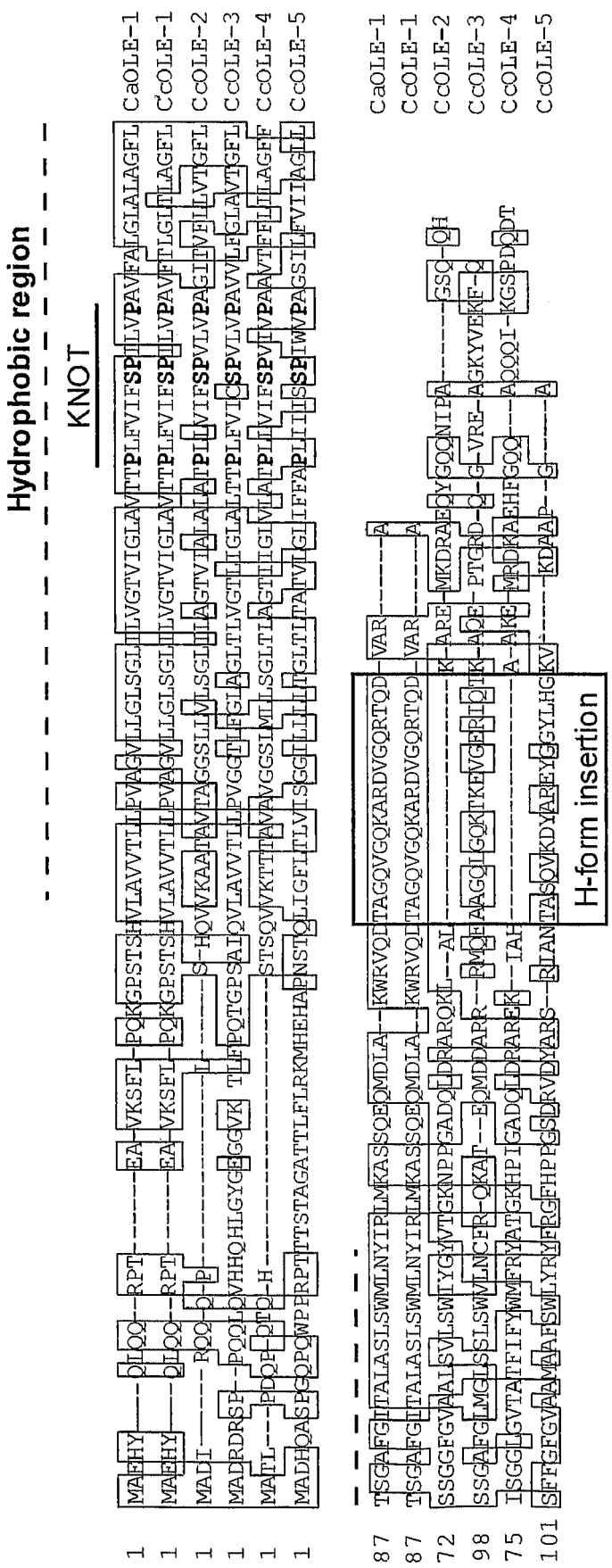
FIG. 1. Optimal alignment of Coffea protein sequences. The alignments were generated with the clustal W program in the Lasergene software package (DNASTAR) and then adjusted manually to optimize the alignment. The location of the conserved P-(5X)-SP-(3X)-P proline knot motif is indicated, with highly conserved prolines and serines shown in bold. Conserved sequences are boxed. The H-form insertion (see FIG. 4) is shown in the heavy-type box. Accession numbers of the aligned oleosin sequences are: CaOLE-1 (SEQ ID NO: 8; AY928084), CcOLE-1 (SEQ ID NO:9; AY841271), CcOLE-2 (SEQ ID NO:10; AY841272), CcOLE-3 (SEQ ID NO:11; AY841273), CcOLE-4 (SEQ ID NO:12; AY841274) and CcOLE-5 (SEQ ID NO:13; AY841275).
Figure 3:
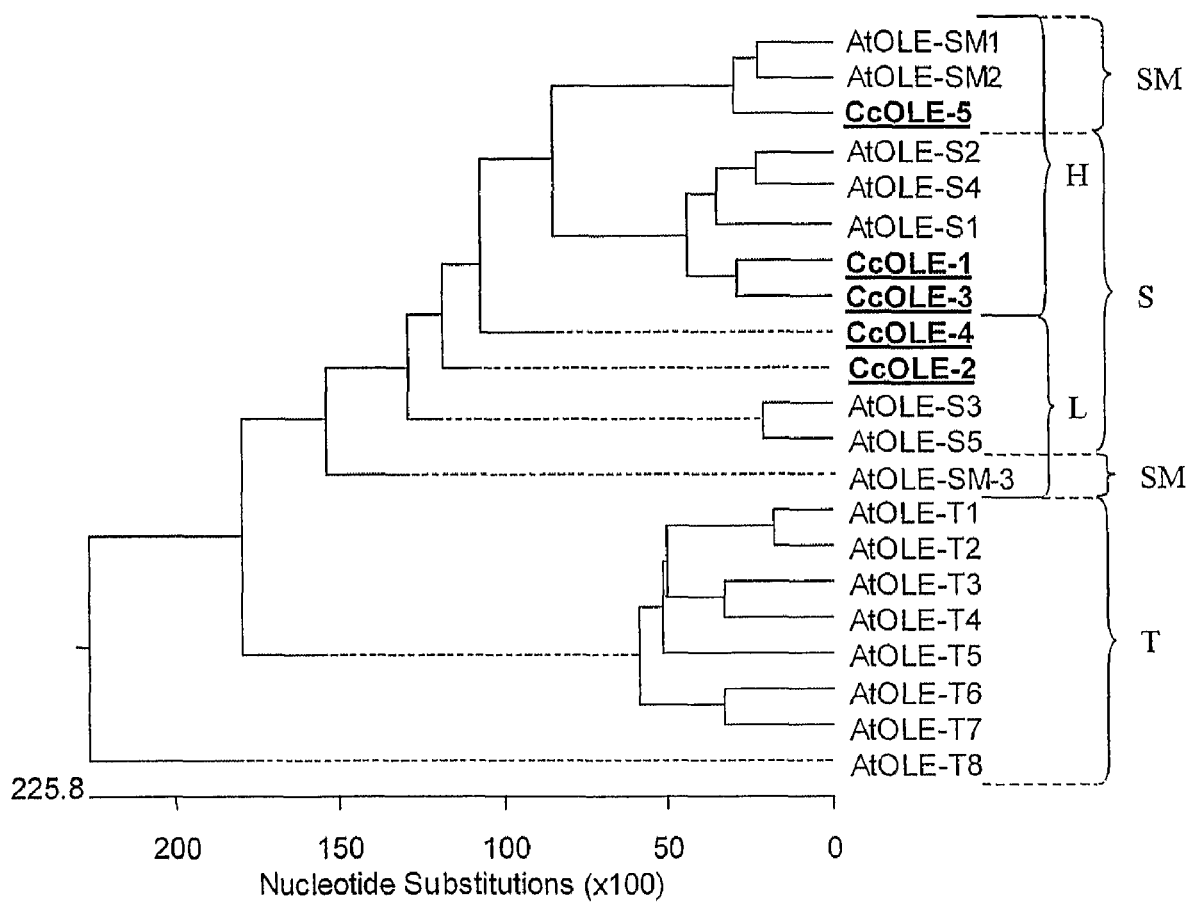
FIG. 3. ClustalW based phylogeny of the five C. canephora oleosins and 16 Arabidopsis oleosins. The complete protein sequences of each gene were aligned with the ClustalW program of the Lasergene package and then adjusted manually to optimize the alignment. To illustrate the potential evolutionary relationships between the various sequences, the resulting alignment is presented in the form of a phylogenetic tree. The scale represents branch distance as the number of residue changes between neighbors. A. thaliana. H- and L-forms are indicated. Locations of Arabidopsis sequences shown as Seed/Microspore (SM), Seed (S) and Tapetum (T). Accession numbers of the aligned oleosin sequences are: AAF01542, BAB02690, CAA44225, Q39165, AA022633, AAF69712, BAB02215, AAC42242, NP196368, NP196369, CABS7942, NP196371, NP196372, NP196373, NP196377 and NP200969 for Arabidopsis S1, S2, S3, S4, S5, SM1, SM2, SM3, T1, T2, T3, T4, T5, T6, T7 and T8 respectively.

More than 47,000 EST sequences from several coffee libraries made with RNA isolated from young leaves and from the grain and pericarp tissues of cherries harvested at different stages of development. Overlapping ESTs were subsequently "clustered" into "unigenes" (i.e. contigs) and the unigene sequences were annotated by doing a BLAST search of each individual sequence against the non-redundant protein database. The ORFs of five of the unigenes expressed during grain development were annotated as glycine-rich proteins/oleosins. ESTs representing full-length cDNA for each unigene were isolated and sequenced. These cDNA were named CcOLE-1 to CcOLE-5 (SEQ ID NOS: 2-6) (clones cccs46w9j5, cccs46w20j22, cccs46w31f3, cccs30w17h11 and cccs30w33 respectively) depending on the number of EST obtained. These ESTs were all from libraries obtained from grain at either 30 and 46 weeks post fertilization. The deduced amino acid sequences (FIG. 1) of CcOLE-1 to CcOLE-5 have molecular masses 15.7, 14.1, 18.6, 15.3 and 17.9 kDa respectively. These proteins each contain a hydrophobic region of 81, 73, 80, 72 and 75 amino acids respectively with the signature KNOT motif containing 3 conserved prolines and 1 conserved serine at its center.

FIG. 9A to 9E shows show the coffee oleosins each aligned with the four most homologous sequences in the GenBank non-redundant protein database and Table 1 shows the percentage of identity for each coffee protein with the closest related database proteins.

TABLE 1

Identity of the *Coffea canephora* oleosin amino acid sequence with the most homologous GenBank sequences.

| Oleosin | Gene name (accession number) | Publication | % identity |
|---|---|---|---|
| 1 | *Coffea canephora* (AY841271) | | 100 |
| | *Coffea arabica* (AY928084) | | 99 |
| | *Sesamum indicum* (U97700 and JC5703) | Chen et al. 1997 | 69 |

TABLE 1-continued

Identity of the *Coffea canephora* oleosin amino acid sequence with the most homologous GenBank sequences.

| Oleosin | Gene name (accession number) | Publication | % identity |
|---|---|---|---|
|   | *Olea europaea* (AAL92479) | NP | 55 |
|   | *Perilla frutescens* (AAG43516) | NP | 51 |
| 2 | *Coffea canephora* (AY841272) |   | 100 |
|   | *Citrus sinensis* (T10121) | Naot et al. 1995 | 80 |
|   | *Prunus dulcis* (Q43804) | Garcia-Mas et al. 1995 | 79 |
|   | *Corylus avellana* (AAO65960) | NP | 77 |
|   | *Sesamum indicum* (AF091840; AAD42942) | Tai et al. 2002 | 77 |
| 3 | *Coffea canephora* (AY841273) |   | 100 |
|   | *Olea europaea* (AAL92479) | NP | 64 |
|   | *Sesamum indicum* (AF302807; AAG23840) | Tai et al. 2002 | 62 |
|   | *Perilla frutescens* (AAG24455) | NP | 59 |
|   | *Perilla frutescens* (AAG09751) | NP | 58 |
| 4 | *Coffea canephora* (AY841274) |   | 100 |
|   | *Sesamum indicum* (AF091840; AAD42942) | Chen et al. 1997 | 56 |
|   | *Citrus sinensis* (T10121) | Naot et al. 1995 | 56 |
|   | *Corylus avellana* (AAO65960) | NP | 54 |
|   | *Prunus dulcis* (S51940) | Garcia-Mas et al. 1995 | 53 |
| 5 | *Coffea canephora* (AY841275) |   | 100 |
|   | *Arabidopsis thaliana*-SM2 (BAB02215) | Kim et al. 2002 | 56 |
|   | *Arabidopsis thaliana*-SM1 (AAF69712) | Kim et al. 2002 | 53 |
|   | *Theobroma cacao* (AF466103) | Guilloteau et al. 2003 | 46 |
|   | *Corylus avellana* (AAO67349) | NP | 39 |

(NP = not published).
Accession numbers of the *Coffea* oleosins were deposited in the NCBI genebank.

The different coffee oleosin sequences were examined in more detail. Hydrophobicity plots for each coffee oleosin clearly indicate the presence of a large region with a negative value, which is equivalent to the central hydrophobic region (FIG. 10). These hydrophobic profiles are similar to previous published profiles of seed specific (S) oleosins from *T. cacao* (Guilloteau et al., 2003) and *Arabidopsis* (Kim et al., 2002) and the *Arabidopsis* seed and microspore specific (SM) oleosins (Kim et al., 2002).

Figure 4:
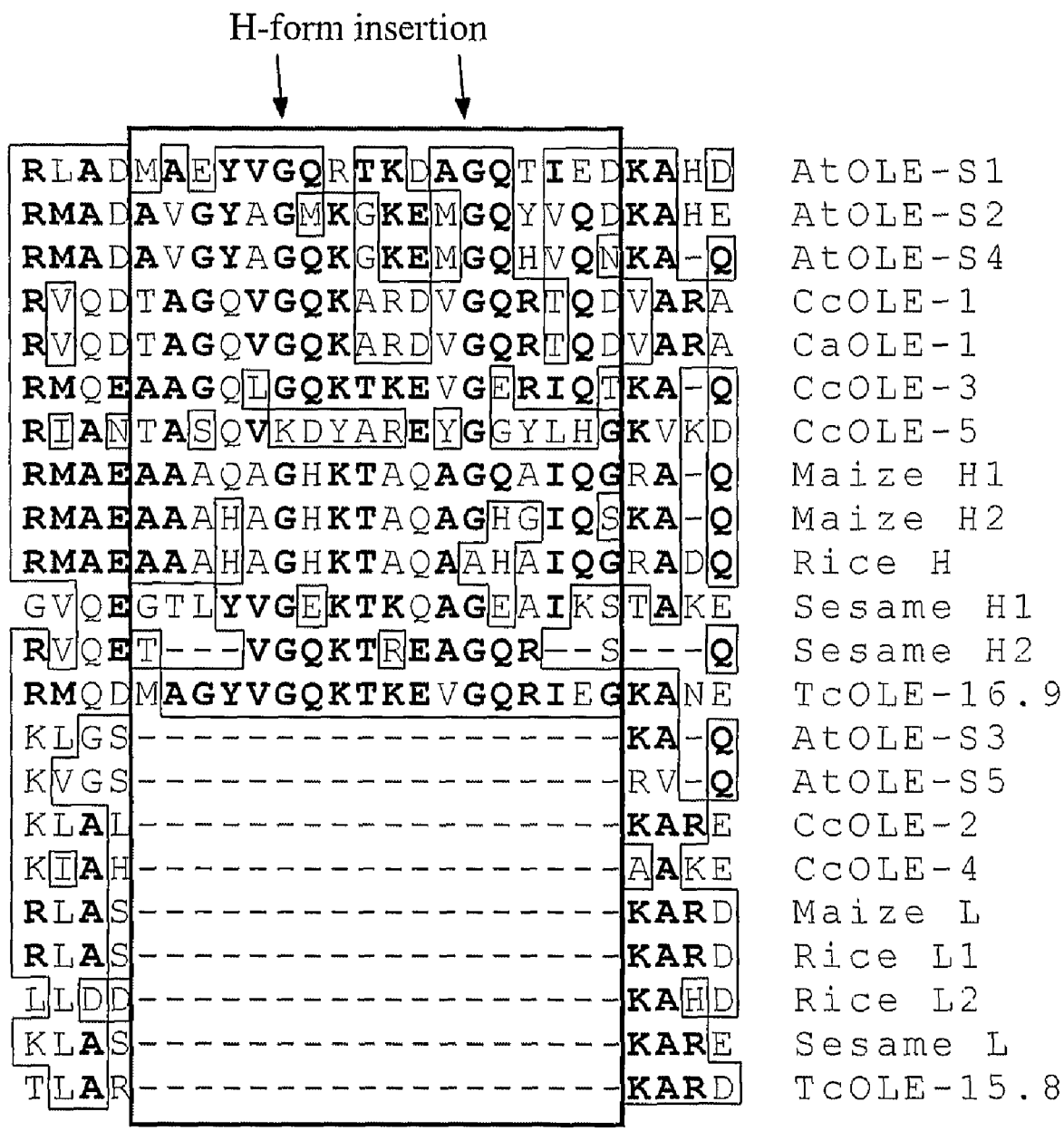
FIG. 4. Optimal alignment of the region containing the 18-residue H-form insertion motif in the C-terminal domain of oleosins. The region containing the site of the 18-residue insertion of all the coffee oleosins was aligned with selected oleosins from other plant species using the clustal W program with a subsequent manual optimization step. Conserved residues are boxed; residues with the highest conservation are in bold. Accession numbers of the aligned oleosin sequences are: AAF01542, BAB02690, CAA44225, Q39165 and AA022633, for Arabidopsis Seed 1 (S1), S2, S3, S4, and S5 (Kim et al., 2002; Tai et al., 2002) (SEQ ID NOs.: 18-22, respectively); AY928084 for Coffea arabica OLE-1 (SEQ ID NO.: 1); P21641, S52030 and S52029 for Maize H1, H2 and L (SEQ ID NOs.:23-25, respectively); U43931, U43930 and BAD23684 for Rice H, L1 and L2 (SEQ ID NOs.:26-28, respectively); U97700 (Chen et al., 1997) AF302807 and AF091840 (Tai et al., 2002) for Sesamum indicum H2, H1 and L (SEQ ID NOs.:29-31 respectively); AF466102 and AF466103 for T. cacao 16.9 and 15.8 (Guilloteau et al., 2003) (SEQ ID NOs.:32-33, respectively).

It has been previously found by Tai et al. (2002) that oleosins expressed during seed development fall into two classes, which they termed the H and L forms, and are distinguished by the presence or absence of an 18 amino acid insertion in the C-terminal region. Alignment of the C-terminal region around the insertion site of the five coffee oleosins with the equivalent regions of a number of other oleosins found in the Genebank database was therefore performed (FIG. 4). This alignment prompted classification of OLE-1, OLE-3 and OLE-5 as H-oleosins and OLE-2 and OLE-4 as L-oleosins. It is noted that the C-terminal 18-residue insertion of OLE-5 was less homologous to the H-insertions of the other oleosins, including the absence of a highly conserved glycine at position 6 of the insertion. Previous work on in vitro assembled oil bodies demonstrated that either H- or L-oleosins from rice and sesame can stabilize oil bodies, although oil bodies reconstituted with the L-oleosin alone were more stable than those reconstituted with H-oleosin or a mixture of H- and L-oleosins (Tzen et al., 1998; Tai et al., 2002).

Example 5

Tissue-Specificity and Developmental Distribution of CcOLE Gene Expression

Table 2 shows that there are 52 ESTs in the unigene representing the most abundant oleosin (CcOLE-1) and only 5 ESTs in the unigene representing the least abundant oleosin (CcOLE-5). Except for the EST CcOLE-5 EST found in the leaf library, all the oleosin ESTs were detected only in the seed libraries and not in the leaf or pericarp libraries.

TABLE 2

Number and distribution of ESTs in the unigene containing the full-length *Coffea canephora* oleosin cDNA

|   |   | Number of ESTs | | | | |
|---|---|---|---|---|---|---|
| Oleosin | Unigene | Seed 18 w | Seed 30 w | Seed 46 w | Pericarp | Leaf | Total |
| CcOLE-1 | 123851 | 0 | 19 | 33 | 0 | 0 | 52 |
| CcOLE-2 | 124185 | 0 | 13 | 15 | 0 | 0 | 28 |
| CcOLE-3 | 121257 | 0 | 11 | 3 | 0 | 0 | 14 |
| CcOLE-4 | 123972 | 0 | 9 | 1 | 0 | 0 | 10 |
| CcOLE-5 | 120543 | 0 | 3 | 1 | 0 | 1 | 5 |

Figure 5:
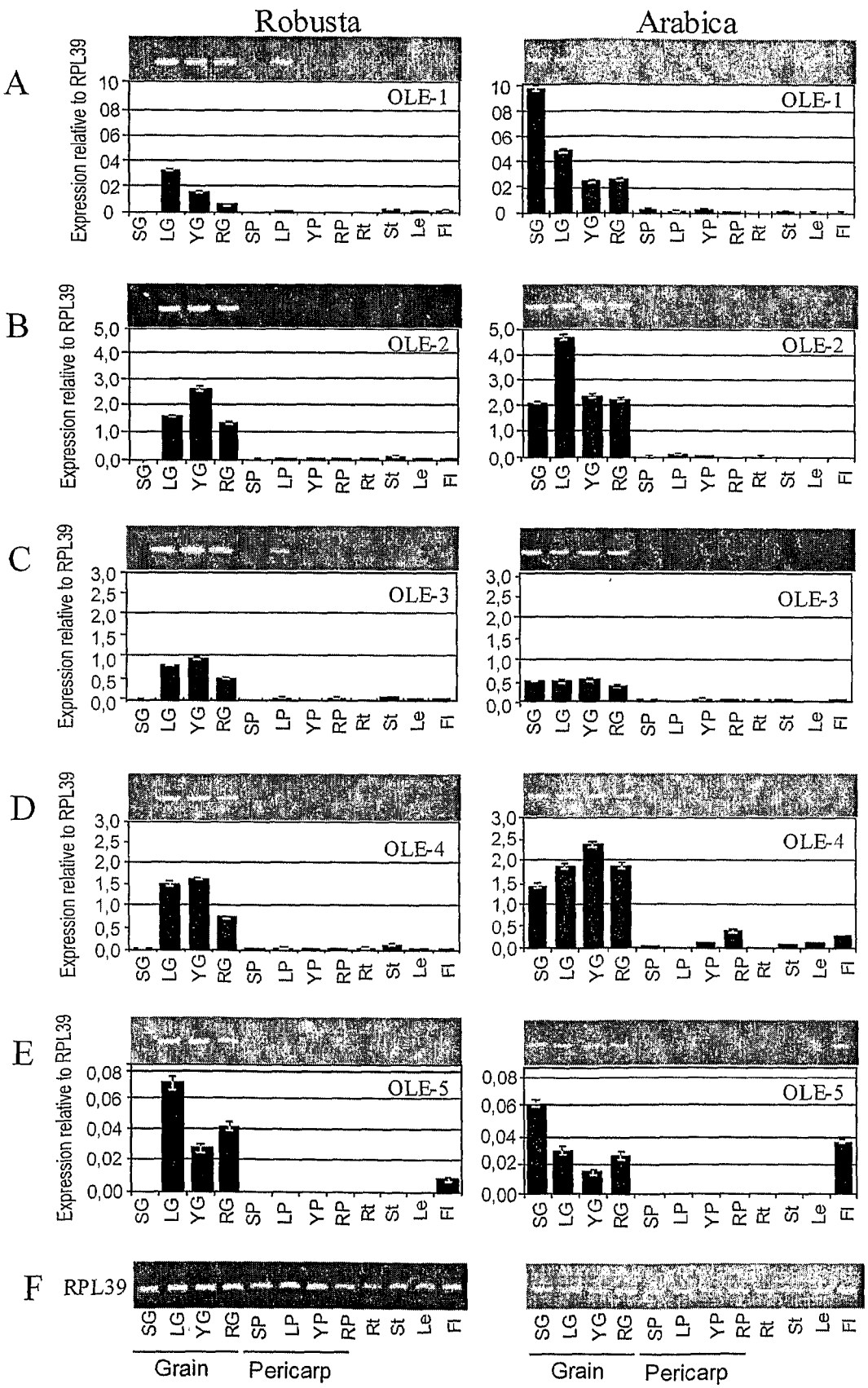
FIG. 5. Expression of Oleosin genes of Coffea canephora and Coffea arabica in different tissues and during seed maturation. Transcript levels for A) OLE-1, B) OLE-2, C) OLE-3, D) OLE-4, E) OLE-5 in various tissues, and in the developing seed and pericarp tissues of coffee cherries at different stages was determined by both conventional (inserted panels above histograms) and by quantitative RT-PCR (histograms). The expression levels are determined relative to the expression of transcripts of the constitutively expressed RPL39 gene in the same samples. F) shows the RPL39 control transcript in all tissues and samples. SG, Small green grain; LG, large grain; YG, yellow grain; RG, ripe grain; SP, Small green pericarp.

To confirm that coffee oleosins were grain specific, the expression of each gene was studied by RT-PCR, utilizing the methods described in Example 2. Oleosin transcript levels were analysed in the grain and fruit at four different developmental stages, as well as the leaves, stem, flowers and roots of *C. canephora* (robusta; BP409) and *C. arabica* (T-2308). The results from the RT-PCR experiment confirm that all five of the coffee oleosins were primarily expressed in the seeds (FIG. 5A to 5E). The expression of RPL39, a constitutively expressed ribosomal protein cDNA, was used as a positive control to show successful RT-PCR amplification in each RNA sample (FIG. 5F).

To quantify the transcript levels for each OLE gene at different stages of coffee grain development, as well as in several other coffee tissues, transcript-specific assays based on fluorescent real-time RT-PCR (TaqMan: Applied Biosystems) were developed for each gene, and the relative transcript levels in each RNA sample were quantified versus the expression of a constitutively transcribed gene (RPL39) in the same sample. Quantitative TaqMan-PCR was carried out with the cDNA using the protocol recommended by the manufacturer (Applied Biosystems, Perk-in-Elmer). All reactions contained 1× TaqMan buffer (Perk-in-Elmer) and 5 mM MgCl$_2$, 200 µM each of dATP, dCTP, dGTP and dTTP, and 0.625 units of AmpliTaq Gold polymerase. PCR was carried out using 800 nM of each gene specific primers, forward and reverse, and 200 nM TaqMan probe, and 1000-fold dilution of cDNA corresponding to 0.001 µg of original RNA. Primers and probes were designed using PRIMER EXPRESS software (Applied Biosystems). Gene-specific primers and probes are shown in Table 3. The reaction mixture was incubated for 2 min at 50° C., then 10 min at 95° C., followed by 40 amplification cycles of 15 sec at 95° C./1 min at 60° C. Samples were quantified in the GeneAmp 7500 Sequence Detection System (Applied Biosystems). Transcript levels were normalized to the levels of the control gene RPL39.

The results of the cross specificity testing of the OLE primers/probe sets determined as described by Tan et al. (2003) and Simkin et al. (2004b) are summarized in Table 4. A standard curve was made from corresponding cDNA. The data represent the equivalent amount of signal produced by each primer/probe set with each cDNA. In pair-wise tests with other *Coffea* oleosins, each probe provided a minimum of $10^4$-fold discrimination in detection of related transcripts.

TABLE 4

Specificity of each set of CcOLE TaqMan real-time PCR primers and probes in detecting the related sequence.

| Probe | Transcript | | | | |
|---|---|---|---|---|---|
| | CcOLE-1 | CcOLE-2 | CcOLE-3 | CcOLE-4 | CcOLE-5 |
| OLE-1 | 1 | $<2.8 \times 10^{-7}$ | $<7.1 \times 10^{-7}$ | $<4.1 \times 10^{-9}$ | $<1.8 \times 10^{-8}$ |
| OLE-2 | $<1.9 \times 10^{-6}$ | 1 | $<1.2 \times 10^{-6}$ | $<1.3 \times 10^{-6}$ | $<6.4 \times 10^{-7}$ |
| OLE-3 | $<1.3 \times 10^{-5}$ | $<1.8 \times 10^{-5}$ | 1 | ND | ND |
| OLE-4 | ND | ND | ND | 1 | $<5.6 \times 10^{-14}$ |
| OLE-5 | ND | ND | ND | $<1.3 \times 10^{-4}$ | 1 |

ND = not detected.
Plasmid containing each cDNA was added per reaction in a pair-wise test against each primer probe set. The data represent the equivalent amount of signal produced by 400 pg of each specific gene.

TABLE 3

| gene | | sequence | size | SEQ ID NO.: |
|---|---|---|---|---|
| OLE-1 | Forward | CCGACTCATGAAGGCGTCTT | | 57 |
| | Reverse | GTCCTGCAGCGCCACTTT | | 58 |
| | Probe[1] | CCAGGAGCAAATGG | 60 | 59 |
| OLE-2 | Forward | GACCGGGCAAGGCAAAA | | 60 |
| | Reverse | GCTCAGCCCTGTCCTTCATC | | 61 |
| | Probe[1] | CTGCTCTTAAGGCTAGGG | 56 | 62 |
| OLE-3 | Forward | CCGCCACAACAGCTTCAAG | | 63 |
| | Reverse | ACACCGCCTTCCCCATATC | | 64 |
| | Probe[1] | ACACCATCAGCACCTG | 56 | 65 |
| OLE-4 | Forward | ATTGCTCATGCAGCTAAGGAGAT | | 66 |
| | Reverse | TGAGCCTGCTGCCCAAA | | 67 |
| | Probe[1] | AGGGACAAAGCTGAAC | 59 | 68 |
| OLE-5 | Forward | GGTTCGGACCGGGTTGAC | | 69 |
| | Reverse | TCACCTGACTTGCCGTATTGC | | 70 |
| | Probe[1] | ATGCAAGAAGCCGAATT | 56 | 71 |
| 11S | Forward | CGTGCTGGCCGCATTAC | | 72 |
| | Reverse | GGAGGCTGCTGAGGATAGGA | | 73 |
| | Probe[1] | ACTGTTAATAGCCAAAAGA | 58 | 74 |
| STO-1 | Forward | GCACTGGAAGGCCTCTTTTG | | 75 |
| | Reverse | GGACTTGCACCAGTGAGAAGTTT | | 76 |
| | Probe[2] | AGGGCTCCCCTCCG | 61 | 77 |
| RPL39 | Forward | GAACAGGCCCATCCCTTATTG | | 78 |
| | Reverse | CGGCGCTTGGCAATTGTA | | 79 |
| | Probe[2] | ATGCGCACTGACAACA | 69 | 80 |

[1]MGB Probes were labelled at the 5' with fluorescent reporter dye 6-carboxyfluorescein (FAM) and at the 3' with quencher dye 6-carboxy-N,-N-,N'-N-tetramethylrhodamine (TAMRA). All sequences are given 5' to 3'.
[2]RPL39 and CcSTO-1 probes were labelled at the 5' with fluorescent reporter dye VIC and at the 3' end with quencher TAMRA.

Using the TaqMan assays, the levels of OLE transcripts were quantified in the same cDNA samples employed previously for conventional RT-PCR. The results presented in FIG. 5A to 5E (histograms) confirm that each OLE gene exhibits significant expression only in grain. However, weak expression of the various oleosin genes was also detected in certain other tissues. This is most likely due to the existence of oil bodies in other tissues. It has been shown that oil body biogenesis can occur outside of the embryo in tobacco leaf cells (Wahlroos et al., 2003), *Olea europea* fruit (Donaire et al., 1984) and in maturing rice reeds (Wu et al., 1998). Olesoins are also found associated with the ER (Abell et al., 1997; Beaudoin and Napier, 2002). The most significant level of oleosin transcripts detected outside of the grain was seen for OLE-5, where expression was very clearly detected in whole mature flowers. This latter observation is consistent with the alignments presented earlier, which indicate that OLE-5 may belong to the SM-group of oleosins (Kim et al., 2002). In fact, this latter observation is supported by the results obtained from a sequence comparison between the 16 known *Arabidopsis* sequences and the 5 oleosin sequences from coffee (FIG. 2).

It was noted that OLE transcripts appear to be induced earlier in *Coffea arabica* when compared to *C. canephora* (robusta). Similar results are shown in Table 2 above, which show that no ESTs encoding oleosin genes were detected in the robusta sample at 18 weeks post fertilization. Taken together, these data indicate that the robusta cherries at the small green stage are less developed than arabica cherries with a similar appearance. This difference in development might be closely linked to the slower maturation of robusta cherries versus arabica cherries; robusta cherries develop over a period of 9 to 11 months while arabica fruit develop over a period of 6 to 8 months (Costa, 1989).

To confirm the foregoing interpretation, a specific Taqman quantitative RT-PCR assay was designed to examine the expression of another coffee gene, the 11S storage protein gene, which is also strongly induced during the mid-late stages of grain development (Marraccini et al., 1999). The results presented in FIG. 6A again show that the robusta small green grain sample also exhibited no detectable 11S expression, while the comparable sample from arabica exhibited significant expression of this gene. Furthermore, additional expression profiling of grain specific genes using Taqman assays has also demonstrated that the expression profile of the small green robusta grain sample is different from the profile associated with small green arabica grain (data not shown). Slight differences observed between the results for TaqMan and conventional RT-PCR (FIG. 5) are likely due to the non-quantitative nature of the latter over 40 cycles.

When the pattern of expression was examined for each oleosin gene exclusively in robusta grain, it appeared that CcOLE-1, and to a lesser extent CcOLE-5, exhibited a different pattern of expression than did the other three genes; the transcript levels of CcOLE-1 and 5 were highest at the large green stage, and then progressively decreased until maturity, although the decrease was less pronounced in CcOLE-5. It is noted that CcOLE-1 and CcOLE-5 are both H oleosins, and thus the observed expression pattern was different from other coffee H oleosin (CcOLE-3). The expression patterns found for CcOLE-2, CcOLE-3, and CcOLE 4 in robusta grain indicates that the transcript levels for those genes peaked at the yellow stage, and that the levels before and after that stage were somewhat lower. When the transcript levels of the five oleosins in arabica and robusta grain were compared, the patterns of transcript expression were relatively similar, once the developmental timing difference was taken into account (i.e. small green grain arabica was approximately equivalent to large green robusta). However, upon closer examination, some differences in transcript levels between arabica and robusta grain could be observed. Assuming that the level of RPL39 transcripts are similar in both arabica and robusta, the peak transcript levels of OLE-1, OLE-2 and OLE-4 appeared to be approximately twofold higher in arabica than in robusta. In contrast, the reverse appeared to be the case for OLE-3, where transcript levels were approximately twofold less at the yellow stage of arabica grain as compared with the yellow stage of robusta grain. Of note, 11S transcript levels were relatively similar between these two species. This latter observation implies that the differences between arabica and robusta in the accumulation of the oleosin transcripts are probably not due to differences in RPL39 expression.

Wu et al. (1998) showed that transcript levels of the two rice oleosins appeared seven days after pollination and vanished in mature seeds. A similar result was obtained by Guilloteau et al., (2003), who showed that the oleosin transcripts decreased in mature seeds reaching a peak at 146 days post fertilization (dpf) and decreasing to lower levels at 160 dpf. In the instant example, transcript levels of OLE-1 to OLE-5 were all shown to decrease in the final stages of maturation, although not to the same extent. OLE-1 and OLE-5 showed the greatest decrease during the course of the maturation period.

Without intending to be limited by any explanation of mechanism, the high level of OLE-1 expression found in the early stage of endosperm development could imply this oleosin has some important role in oil body initiation/formation. Furthermore, it is noteworthy that the samples with the higher oil content (arabica) also have higher levels of OLE-1 expression. While it has been proposed by Ting et al. (1996) the oleosin content is not related to oil content, it may still be the case that oil content could be related to the level of the OLE-1 type H oleosin expressed at the initiation stage of oil body formation.

Example 6

Expression of Oleosins During Seed Germination

The transcript levels for each OLE gene were quantified at different stages of germination in *C. arabica*. The results from the quantitative RT-PCR experiment showed that OLE-1 to OLE-4 transcripts were detected in the seeds in the early stages of germination (FIG. 7). OLE-1, OLE-2 and OLE-3 transcript levels were observed to peak at 3 days after imbibition (3DAI). In the case of OLE-2, transcript levels were observed to increase to levels observed in the final stages of seed maturation (see FIG. 7). At 5DAI H-form oleosins OLE-1 and OLE-3 transcript levels decreased significantly along with OLE-2 and remained low throughout the remainder of germination. OLE-2 and OLE-3 transcript levels were undetectable at 60DAI. OLE-5, previously identified as likely being an SM oleosin, was not detected in germinating grain. Furthermore, quantitative RT-PCR also showed a concomitant increase in STO-1 transcript during germination, when compared to oleosins expression (see FIG. 6C and Example 9).

Example 7

Copy Number of CcOLE-1 the Genome of *C. canephora*

It is known that individual oleosins are usually encoded by either single genes, or genes with low copy number (Tai et al., 2002). In this example, it was confirmed that the *Coffea canephora* OLE-1 is encoded by a single, or low copy number gene in the coffee genome. Southern blot experiments were performed to estimate the copy number of CcOLE-1. The complete insert of CcOLE-1 cDNA, including 3' untranslated region, was labeled with $P^{32}$ and then hybridized under high stringency conditions to genomic DNA from robusta variety BP-409, which had been digested with several restriction enzymes as described above. The results obtained after 10 days exposure (FIG. 11) shows that single and double digestions resulted in the detection of primarily one major band except for the Hind III+SspI digest, where a second band was also detected. This second band was believed to be due to the presence of a HindIII cut site at 123 bp from the transcriptional start site (see FIG. 8). The presence of weaker bands was also detected in the DraI and SspI single digests, which were missing from double digests. These were likely due to partial digestion of the genomic DNA, or to very weak cross hybridization with the one or more of the other oleosins. These data strongly indicate that only one, or possibly two, genes in the coffee genome encode CcOLE-1.

Example 8

Identification of Seed-Specific Regulatory Elements in the *Coffea canephora* OLE-1 5' Region The promoter region of OLE-1 was isolated from the genome of *C. canephora* (robusta BP-409). A sequence of approximately 1075 bp upstream of the CcOLE-1 ATG site was recovered by a PCR assisted primer walk and completely sequenced as describe in earlier examples. The promoter sequence obtained was then analysed for the presence of known regulatory sequences (FIG. 8). This analysis indicated the presence of a number of DNA regulatory sequences. For example, a TTTAAAT motif is located 39 bp upstream of the 5' end of the CcOLE-1 cDNA (indicated by an arrow), and is a likely candidate for the TATA box sequence. Other regulatory elements previously shown to be responsible for the spatial and temporal specificity of storage-protein gene expression in a variety of plants were also found. The sequence TGTAAAGT (456/463) has been identified as a so called 'endosperm motif' and is implicated in controlling the endosperm-specific expression of glutenins in barley (Thomas, 1993) and wheat (Hammond-Kosack et al., 1993), pea legumin (Shirsat et al., 1989) and maize zein (Maier et al., 1987) promoters. Other sequences were also identified, such as the E-box CANNTG (CAAATG 738/743; CATGTG 914/919), which is thought to be involved in seed-specific expression of the French bean phaseolin (Kawagoe and Murai, 1992) and the S2 storage protein of Douglas-fir (Chatthai et al., 2004). An element CATGCAAA (886/894) is similar to the so-called RY repeat region CATGCA(T/a)(A/g); the core region of the legumin box (Dickinson et al., 1988; Shirsat et al., 1989). This motif is essential for seed-specific expression of soybean 11S legumin (Bäumlein et al., 1992), β-conglycinin (Chamberlan et al., 1992) and glycinin (Lelievre et al., 1992) genes. The CCATGCA (885/891) sequence region is similar to both the GCATGC RY-repeat element of the 2S albumin promoter essential for the seed-specific expression in transgenic tobacco seeds (Chatthai et al., 2004) and the CATGCA and CATGCC sequence detected in the seed-specific 11S promoter of C. arabica (Marraccini et al., 1999). Also noted was an AT-rich motif ATATTTATT (504/512), similar to the seed-specific enhancer identified in the upstream sequence of the soybean β-conglycinin α-subunit gene (Allen et al., 1989).

Example 9

Isolation and Characterization of a Coffee Steroleosin cDNA

A single member of the steroleosin family, designated CcSTO-1 (cccs46w11o15, AY841276). CcSTO-1 herein, was detected in the grain at 30 weeks and 46 weeks after flowering (Table 5).

TABLE 5

Number and distribution of ESTs in the unigene containing the full-length steroleosin cDNA

| | | Number of ESTs | | | | | |
|---|---|---|---|---|---|---|---|
| Steroleosin | Unigene | Seed 18 w | Seed 30 w | Seed 46 w | Pericarp | Leaf | Total |
| CcSTO-1 | 121095 | 0 | 2 | 5 | 0 | 0 | 7 |

Steroleosins have previously been identified in associated with seed oil bodies (Lin et al., 2002; Lin and Tzen, 2002). Steroleosin are $NADP^+$-binding sterol dehydrogenases, which manifest dehydrogenase activity on to both estradiol and corticosterone in vitro (Lin et al., 2002). Without intending to be limited by any explanation of mechanism, steroleosins may be involved in signal transduction regulating a specialized biological function related to seed oil bodies, which may be affiliated to the mobilization of oil bodies during seed germination (Lin et al., 2002). Lin et al. (2002) and Lin and Tzen, (2004) identified two distinct steroleosins associated with oil bodies in Sesame indicum, designated steroleosin-A and steroleosin-B. Lin et al., (2002) also identified 8 members of the steroleosin family in Arabidopsis thaliana in the NCBI non-redundant protein database. However, Joliver et al. (2004) detected only one steroleosin (steroleosin-1; BAB09145) associated with Arabidopsis oil bodies in vivo. An optimized alignment of CcSTO-1 protein sequence with the two most homologous GenBank protein sequences is presented in FIG. 2. The full-length amino acid sequence of CcSTO-1 has 79% and 66% homology with the S. indicum oil-body associated steroleosin-B (AF498264; Lin and Tzen, 2004) and A. thaliana steroleosin-7 (CAB39626; see Lin et al., 2002) respectively. The conserved S-(12X)-Y-(3X)-K active site is indicated. Furthermore, a proline KNOT motif within the N-terminal domain that has two conserved prolines is also indicated and is believed to function as an anchor in a manner similar to that previously reported for the oleosin KNOT motif (Lin et al., 2002).

A gene specific Taqman quantitative RT-PCR assay of STO-1 transcript levels in both arabica and robusta showed that this transcript is primarily expressed at low levels in the grain, although approximately 16-fold lower levels of expression were also observed in other tissues (FIG. 6). When the steroleosin transcript levels in arabica and robusta grain are compared, STO-1 transcript levels were shown to be relatively similar, between these two species, once the developmental timing difference is taken into account. The appearance of STO-1 transcripts at a later stage in robusta is similar to the results observed for all the genes tested here. In both robusta and arabica grain, STO-1 the transcript levels peak at large green stage, and then decrease in the later stages of development. A similar result was obtained by Lin and Tzen (2004) who showed that the sesame seed oil-body associated steroleosin-A transcript accumulated during seed development.

Example 10

Functional Analysis of the Coffee Oleosin Promoter CcDH2 in Arabidopsis thaliana Using a Promoter-GUS Fusion A functional analysis of the coffee oleosin promoter CcDH2 in Arabidopsis thaliana was conducted. The promoter was linked to a reporter gene, namely a sequence encoding beta-glucuronidase (GUS).
Materials and Methods:
The oleosin CcOle1 promoter sequence was amplified using the polymerase Pfu1 under the conditions described by the supplier (Stratagene) and the following primers:

```
                                        (SEQ ID NO.: 81)
TG-702    ttgaagcttACGACAGGTTTCCCGACTG
and
                                        (SEQ ID NO.: 82)
TG-703    gcagatctaccatggGCGGTGGACGGTAGCTTAT.
```

The PCR fragment thus obtained was then cut with HindIII and BglII and cloned into the HindIII/BglII sites of the plant transformation vector pCAMBIA1301. This places the approximately 1 kb fragment containing the oleosin promoter sequence, which contains the nearly complete 5' untranslated region (minus only 3 bp) found in the oleosin cDNA (approximately 70 bp) at the ATG for the GUS (first exon of GUS). The correct positioning of the promoter was verified by sequencing. The new oleosin promoter containing vector was named pCAMBIA1301UCD3.1

Plant transformation. The transformation vector pCAMBIA1301UCD3.1 was then transformed into Agrobacterium tumefaciens strain EHA105 using standard procedures. The hygromycin resistance gene, driven by a 2×35S promoter, was the plant selectable marker in pCambia1301. Agrobacterium tumefaciens mediated transformation of Arabidopsis (with the plasmid pCAMBIA1301UCD3.1) was performed by floral-dip method (Clough and Bent, 1998).

Transformed plants were identified by plating seed on 0.8% agar containing 1 mM potassium nitrate and 50 μg per ml hygromycin. Transformed seedlings were identified 7 days after plating as plants with an extended primary root. Seedlings were transferred to 0.8% agar containing 0.5×M&S salts. Plants were transferred to soil when the second leaf pair developed and allowed to mature and set seed (T1). In some cases, the T1 seeds were germinated, and then allowed to grow and to set seeds (T2).

GUS Staining. The seedlings and siliques examined for GUS staining were either from T1 or T2 seeds, and were at different stages of development. The GUS staining solution was prepared by dissolving 5 mg X-Gluc in 50 μL1 dimethyl formamide, and then adding this to 10 ml 50 mM $NaPO_4$ pH 7.0. With a fine forceps, the seedlings were transferred from the germination plates into a 1.5 ml microfuge tube containing 1.0 ml of GUS stain. The tubes were transferred to a desiccator and placed under vacuum for 10 minutes and incubated at 37° C. (in the dark) for 24 or 48 hours. The stain was removed and replaced with the destaining solution (70% EtOH). Clearing was accelerated by placing the tubes at 37° C. Depending on the amount of pigment in the tissue, several changes of 70% EtOH were required. The stained seedlings and other tissues were viewed under a dissecting microscope and images were digitally recorded. In the case of siliques, the siliques were removed from plants and opened with a scalpel to permit penetration of stain. The GUS stain above was modified to include 0.5% Triton X100. Following staining, the siliques were destained by incubating in EtOH:Acetic Acid (2:1) and then incubating in Hoyer's Light medium (100 g Chloral hydrate in 60 ml water). Siliques with younger seeds were preincubated in the Ethanol:Acetic Acid solution for 4 hours, and siliques with older seeds for 8 hours. Siliques were cleared in Hoyer's Light medium for 24 hours to several days.

Results:

GUS expression in *Arabidopsis thaliana* transformed with pCam1301UCD3.1 was observed in seedlings at different developmental stages. Expression was seen in cotyledons, hypocotyls of very young seedlings, and in first true leaves of older seedlings. No significant expression was detected in the roots. GUS activity was not detected in mature leaves. GUS expression was also detected in the silique wall, but the GUS staining in the silique wall was not as intense as in the young germinating seed tissues. It was not possible to completely clear the silique in Hoyler's medium, such that residual green pigmentation remained in the silique wall, giving the stained silique a blue green hue. The GUS activity was restricted to the silique and did not extend to the floral stem.

These data confirm that the coffee oleosin promoter CcOLE-1 drives the expression of the linked coding sequence in seeds, in siliques, as well as in the first cotyledons and the first true leaves of the germinating seeds. Importantly, this result demonstrates that the CcOle-1 promoter sequence described here contains all the functional elements required to drive seed specific gene expression in plants. The data also indicate that the CcOle-1 promoter can be used to drive the expression of genes in immature tissues such as the first two cotyledons derived from germinating seed embryo. In addition, the data indicates that the CcDH2 promoter is activated in other tissues such as the siliques. It is noted that the level of activation in the siliques and the grain appears to be relatively less than in the cotyledons of the germinating seed, although at least part of this difference could be due to differences in the ability to do GUS staining in these very different tissue types. Finally, given the relatively large evolutionary distance between *Arabidopsis* and *Coffea*, the demonstration herein that the coffee CcDH2 promoter functions in *Arabidopsis* implies that this promoter should be active in a relatively wide variety of plants.

Example 11

Induction of Coffee CcOle-1 Gene Expression by Osmotic Stress

To explore the role of the coffee oleosin CcOle-1 in the response to osmotic stress, the expression CcOle-1 was examined in plants submitted to a water deficit (drought).

Materials and Methods:

Dehydration experiments were carried out using small clonally propagated, *Coffea arabica* catimor trees grown in a greenhouse. The trees were approximately three years old and were growing in soil. Several weeks prior to the experiments, the trees were cultivated together in the greenhouse at a temperature of approximately 25° C., with a relative humidity of approximately 70%, and were watered daily using automatic irrigation. At the start of the experiment, three trees acted as controls and were watered daily. The other three trees were not watered and thus underwent a progressive dehydration. Sampling of two young leaves (5-8 cm in size, taken from the emerging growth at the top of plant) was carried out every week for each tree. The samples were frozen directly in liquid nitrogen.

RNA extraction and synthesis of cDNA. The extraction of tissue samples subjected to the various stress treatments and the controls, was done using the RNEASY® Plant mini kit of Qiagen GmbH (Hilden, Germany) The frozen tissue samples were initially ground in a mortar and pestle using liquid nitrogen in order to obtain a powder. The RNA in this frozen powder was then extracted according to the protocol of the RNEASY® Plant mini kit. In brief, a maximum of 100 mg frozen powder was mixed with the cellular lysis buffer and β-mercaptoethanol. For tissues that showed significant necrosis, 2 μM PMSF was also added. In order to eliminate low levels of contaminating genomic DNA, a treatment using DNase-free RNase contained in the RNEASY® Plant mini kit was used (as described by the supplier), that is, a 15 min treatment at room temperature on the column. At the end, the RNA was eluted from the column in 50 μL RNase free water. The RNA quantity was determined by spectrophotometric measurement at 260 nm and the RNA quality was estimated by calculating the absorbance ratio 260 nm/280 nm. The quality of RNAs was also verified by electrophoresis on 1% agarose gels. The reverse transcription reactions for these RNA samples were carried out as follows; approximately 1 μg total RNA and 12.4 μM of oligo-dT [2.3 μl of 70 μM oligo-dT (Proligo)] with Rnase-free water to a final volume of 13 μL. This mixture was incubated at 65° C. for 5 min. Then, 7 μL of a mix of 5× buffer (Transcriptor RT reaction buffer), 20 U of RNase inhibitor, 1 mM of the four dNTPs (250 μm each) and 10 U of TRANSCRIPTOR® reverse transcriptase (Roche, Nutley, N.J.) was added. This mixture was incubated at 55° C. for 40 min. Lastly, 0.5 μL of RNaseH (Invitrogen, Carlsbad, Calif.) was then added to the 20 μL of mixture and the reaction was further incubated for 30 min at 37° C. The cDNAs generated were purified using the SNAP™ Gel Purification Kit of Invitrogen (Carlsbad, Calif.) according to the protocol provided by the supplier.

Primers and MGB-probe design. The primers and MGB-probe sets were designed using the PRIMER EXPRESS™ software (Applied Biosystems, Foster City, Calif.). The temperatures of hybridisation of the primers were around 60° C. whereas that of MGB-probe was close to 70° C. The size of the amplicons was approximately 80 bp. The primers were synthesized by PROLIGO and the MGB probes were synthesized in accordance with supplier's instructions (Applied Biosystems, Foster City, Calif.). The sequences of the primers and probes for CcOle-1 and CcRpl39 have been presented above in Table 3.

Real-time Quantitative RT-PCR. The cDNA used for these experiments was prepared as described above. TaqMan-PCR was performed as described in various sections above. The absence of any significant level of residual genomic DNA in the cDNA preparations was verified by measuring the level of quantitative PCR amplification signal for a genomic specific primer/probe set for GOS gene versus the signal for a GOS gene cDNA probe.

Results:

FIG. 12 shows the induction of CcOle-1 gene expression in the leaves of small green house-grown trees when watering was stopped (drought conditions). After three weeks, CcOle-1 expression was found to be slightly induced by water stress in one plant versus the average Ole-1 expression in three well watered control plants. Little induction was seen in the other two treated plants at week 3. But by week 4, Ole-1 expression was induced in two of the three treated plants. At week 6, all three treated plants showed an elevation in Ole-1 expression. The increased levels of Ole-1 expression found for all three water stressed plants varied between an RQ of >0.18 and <0.4. Although these values were several fold lower than those seen for Ole-1 in developing, grain, they were nonetheless several fold higher than those seen for the unstressed controls leaves. This latter observation indicates that oleosins such as CcOle-1 may contribute to the endogenous protection of the leaf tissues under osmotic stress.

REFERENCES

Aalen R B, Opsahl-Ferstad H G, Linnestad C, Olsen O A. (1994). Transcripts encoding an oleosin and a dormancy-related protein are present in both the aleurone layer and the embryo of developing barley (*Hordeum vulgare* L.) seeds. *Plant J.* 5 (3): 385-396.

Aalen R B. (1995). The transcripts encoding two oleosin isoforms are both present in the aleurone and in the embryo of barley (*Hordeum vulgare* L.) seeds. *Plant Mol. Biol.* 28 (3): 583-588.

Abell B M, Holbrook L A, Abenes M, Murphy D J, Hills M J, Moloney M M. (1997). Role of the proline knot motif in oleosin endoplasmic reticulum topology and oil body targeting. *Plant Cell.* 9(8):1481-1493.

Akiyama M, Murakami K, Ohtani N, Iwatsuki K, Sotoyama K, Wada A, Tokuno K, Iwabuchi H, Tanaka K. (2003). Analysis of volatile compounds released during the grinding of roasted coffee beans using solid-phase microextraction. *J Agric Food Chem.* 51(7): 1961-1969.

Allen R D, Bernier F, Lessard P A, Beachy R N. (1989). Nuclear factors interact with a soybean β-conglycinin enhancer. *Plant Cell.* 1: 623-631.

Bäumlein H, Nagy I, Villarroel R X, Inzé D, Wobus U. (1992). Cis-analysis of a seed protein gene promoter: the conservative RY repeat CATGCATG within the legumin box is essential for tissue-specific expression of a legumin gene. *Plant J.* 2: 233-239.

Beaudoin F, Napier J A. (2002). Targeting and membrane-insertion of a sunflower oleosin in vitro and in *Saccharomyces cerevisiae*: the central hydrophobic domain contains more than one signal sequence, and directs oleosin insertion into the endoplasmic reticulum membrane using a signal anchor sequence mechanism. *Planta* 215(2): 293-303.

Chamberlan S, Daigle N, Bernier F. (1992). The legumin boxes and the 3' part of a soybean β-conglycinin promoter are involved in seed gene expression in transgenic tobacco plants. *Plant Mol. Biol.* 19: 937-949.

Chatthai M, Forward B S, Yevtushenko D, Stefanov I, Osuska L, Osusky M, Misra S. (2004). 2S storage protein gene of Douglas-fir: characterization and activity of promoter in transgenic tobacco seeds. *Plant Physiol. Biochem.* 42(5): 417-23.

Chen J C F, Lin R H, Huang H C, Tzen J T C. (1997). Cloning, expression and isoform classification of a minor oleosin in sesame oil bodies. *J. Biochem.* 122 (4): 819-824.

Chen M C M, Chyan C L, Lee T T T, Huang H C, Tzen J T C (2004) Constitution of stable artificial oil bodies with triacylglycerol, phospholipid, and caleosin. *J Agric Food Chem* 52, 3982-3987.

Chia T Y, Pike M J, Rawsthorne S. (2005). Storage oil breakdown during embryo development of *Brassica napus* (L.). *J Exp Bot.* 56(415):1285-1296.

Chiba A, Ishida H, Nishizawa N K, Makino A, Mae T. (2003). Exclusion of ribulose-1,5-bisphosphate carboxylase/oxygenase from chloroplasts by specific bodies in naturally senescing leaves of wheat. *Plant Cell Physiol.* 44, 914-921.

Chuang R L, Chen J C, Chu J, Tzen J T. (1996) Characterization of seed oil bodies and their surface oleosin isoforms from rice embryos. *J. Biochem* 120(1): 74-81.

Clough, S J and Bent A F (1998). Floral dip: a simplified method for *Agrobacterium*-mediated transformation of *Arabidopsis thaliana*. *Plant Journal* 16; 735-743.

Coste, R. Caféiers et cafés. Techniques aricoles et productions tropicales. G. P. Maisonneuve et Larose et A.C.C.T. Paris, France. (1989).

Crouzillat D, Lerceteau E, Petiard V, Morera J, Rodriguez H, Walker D, Phillips W, Ronning C, Schnell R, Osei J, Fritz P (1996) *Theobroma cacao* L.: a genetic link-age map and quantitative trait loci analysis, *Theor. Appl. Genet.* 93: 205-214.

Dickinson C D, Evans R P, Nielsen N C. (1988). RY repeats are conserved in the 5'-flanking regions of legume seed-protein genes. *Nucleic Acids Res.* 16(1):371.

Donaire J P, Belver A, Rodriguez-Garcia M I, Megias L. (1984). Lipid biosynthesis, oxidative enzyme activities and cellular changes in growing olive fruit. *Rev Esp Fisiol.* 40(2):191-203.

Fernandez-Moya V, Martinez-Force E, Garces R. (2000). Metabolism of triacylglycerol species during seed germination in fatty acid sunflower (*Helianthus annuus*) mutants. *J Agric Food Chem.* 48(3):770-774.

Froese C D, Nowack L, Cholewa E, Thompson J E (2003). Molecular composition and surface properties of storage lipid particles in wax bean (*Phaseolus vulgaris*). *J Plant Physiol.* 160(3):215-225.

Garcia-Mas J, Messeguer R, Arus P, Puigdomenech P. (1995). Molecular characterization of cDNAs corresponding to genes expressed during almond (*Prunus amygdalus* Batsch) seed development. *Plant Mol. Biol.* 27 (1), 205-210.

Guilloteau M, Laloi M, Blais D, Crouzillat D, McCarthy J. (2003). Oil bodies in *Theobroma cacao* seeds: cloning and characterization of cDNA encoding the 15.8 and 16.9 kDa oleosins. *Plant Sci.* 164 (4): 597-606.

Hammond-Kosack M C U, Holdworth M J, Bevan M W. (1993). In vitro footprinting of a low molecular weight glutenin gene (LMWG-1D1) in wheat endosperm. *EMBO J.* 12: 545-554.

Hernandez-Pinzon I, Ross J H E, Barnes K A, Damant A P, Murphy D J. (1999). Composition and role of tapetal lipid bodies in the biogenesis of the pollen coat of *Brassica napus*. *Planta* 208: 588-5S9.

Hsieh K, Huang A H C. (2004). Endoplastic reticulum, oleosins, and oils in seeds and tapetum cells. *Plant Phys.* 136: 3427-3434.

Huang A H C, (1992). Oil bodies and oleosins in seeds. *Ann Rev Plant Phys Mol Biol* 43:177-200.

Huang A H C, (1996). Oleosins and oil bodies in seeds and other organs. *Plant Physiol.* 110(4): 1055-1061.

Hughes D W, Wang H Y. Galau G A. (1993). Cotton (*Gossypium hirsutum*) MatP6 and MatP7 oleosin genes, *Plant Physiol.* 101 (2): 697-698.

Jolivet P, Roux E, D'Andrea S, Davanture M, Negroni L, Zivy M, Chardot T. (2004). Protein composition of oil bodies in *Arabidopsis thaliana* ecotype WS. *Plant Physiol Biochem.* 42(6): 501-509.

Kawagoe Y, Murai N. (1992). Four distinct nuclear proteins recognise in vitro the proximal promoter of the bean seed storage protein β-phaseolin gene conferring spatial and temporal control. *Plant J.* 2: 927-936.

Keddie J S, Edwards E W, Gibbons T, Shaw C H, Murphy D J. (1992). Sequence of an oleosin cDNA from *Brassica napus*. *Plant Mol. Biol.* 19 (6): 1079-1083.

Keddie J S, Tsiantis M, Piffanelli P, Cella R, Hatzopoulos P, Murphy D J. (1994). A seed-specific *Brassica napus* oleosin promoter interacts with a G-Box-specific protein and may be bi-directional. *Plant Mol. Bio.* 24: 327-340.

Kim H U, Hsieh K, Ratnayake C, Huang A H. (2002). A novel group of oleosins is present inside the pollen of *Arabidopsis*. *J. Biol Chem.* 277(25): 22677-22684.

Lee K, Huang A H. (1994). Genes encoding oleosins in maize kernel of inbreds Mo17 and B73. *Plant Mol. Biol.* 26(6): 1981-1987.

Lee K, Ratnayake C, Huang A H. (1995). Genetic dissection of the co-suppression of genes encoding the isoforms of oleosins in the oil bodies of maize kernel. *Plant J.* 7(4): 603-611.

Lelievre J M, Oliveira L O, Nielsen N C. (1992). 5'-CATGCAT-3' elements modulate the expression of glycinin genes. *Plant Physiol.* 98: 387-391.

Li M, Murphy D J, Lee K K, Wilson R, Smith L J, Clark D C, Sung J Y. (2002). Purification and structural characterisation of the central hydrophobic domain of oleosin. *J. Biol. Chem.* 277(40): 37888-37895.

Lin L J, Tai S S, Peng C C, Tzen J T (2002) Steroleosin, a sterol-binding dehydrogenase in seed oil bodies. *Plant Physiol* 128(4):1200-1211

Lin L J, Tzen J T. (2004). Two distinct steroleosins are present in seed oil bodies. *Plant Physiol Biochem.* 42(7-8): 601-608.

Maier U G, Brown J W S, Toloczki C, Feix G. (1987). Binding of a nuclear factor to a consensus sequence in the 5' flanking region of zein genes from maize. *EMBO J.* 6: 17-22.

Marraccini P, Deshayes A, Pétiard V, Rogers W J. (1999). Molecular cloning of the complete 11S seed storage protein gene of *Coffea arabica* and promoter analysis in transgenic tobacco plants. *Plant Physiol. Biochem.* 37(4): 273-282.

Marraccini P, Courjault C, Caillet V, Lausanne F, LePage B, Rogers W, Tessereau S, and Deshayes A. (2003). Rubisco small subunit of *Coffea arabica*: cDNA sequence, gene cloning and promoter analysis in transgenic tobacco plants. *Plant Physiol. Biochem.* 41:17-25.

Marriott K M, Northcote D H. (1975). The breakdown of lipid reserves in the endosperm of germinating castor beans. *Biochem J.* 148(1): 139-144.

Murphy D H, Hernandez-pinzon I, Patel K, Hope R G, McLauchlan J. (2000). Nerw insights into the mechanisms of lipid-body biogenesis in plants and other organisms. *Biochem. Soc. Trans.* 28(6): 710-711.

Murphy D H, Ross J H E. (1998). Biosynthesis, targeting and processing of oleosin-like proteins, which are major pollen coat components in *Brassica napus*. *Plant J.* 13: 1-16.

Naested H, Frandsen G I, Jauh G Y, Hernandez-pinzon I, Nielsen H B, Murphy D J, Rogers J C, Mundy J. (2000). Calosins: $Ca^{2+}$-binding proteins associated with lipid bodies. *Plant Mol. Biol.* 44: 463-476.

Naot D, Holland D, Avsian-Kretchmer O, Eshdat Y, Ben-Hayyim G. (1995). Induction of a gene encoding an oleosin homologue in cultured citrus cells exposed to salt stress. *Gene* 161: 171-173.

Penfield S, Rylott E L, Gilday A D, Graham S, Larson T R, Graham I A. (2004). Reserve mobilization in the *Arabidopsis* endosperm fuels hypocotyl elongation in the dark, is independent of abscisic acid, and requires phosphoenolpyruvate carboxykinase 1. *Plant Cell* 16(10):2705-2718.

Pritchard S L, Charlton W L, Baker A, Graham I A. (2002). Germination and storage reserve mobilization are regulated independently in *Arabidopsis*. *Plant J.* 31(5):639-647.

Qu R D, Huang A H. (1990). Oleosin KD 18 on the surface of oil bodies in maize. Genomic and cDNA sequences and the deduced protein structure. *J. Biol. Chem.* 265 (4):

Rogers, W J., Bézard, G., Deshayes, A., Meyer, I., Pétiard, V., Marraccini, P. (1999). Biochemical and molecular characterisation and expression of the 11S-type storage protein from *Coffea arabica* endosperm. *Plant Physiol. Biochem.* 37(4): 261-272.

Shirsat A, Wilford N, Croy R, Boulter D. (1989). Sequences responsible for the tissue specific promoter activity of a pea legumin gene in tobacco. *Mol. Gen. Genet.* 215(2): 326-331.

Simkin, A J., Laizet, Y., Kuntz, M. (2004a). Plastid lipid associated proteins of the fibrillin family: structure, localisation, function and gene expression. *Rec. Res. Dev. Biochem.* 5: 307-316.

Simkin A J, Underwood B A, Auldridge M, Loucas H, Shibuya K, Clark D G, Klee H J. (2004b). Circadian regulation of the PhCCD1 carotenoid dioxygenase controls emission of β-ionone, a fragrance volatile of petunia flowers. *Plant Physiol.* 136(3): 3504-3514.

Slack C R, Bertaud W S, Shaw B D, Holland R, Browse J, Wright H. (1980). Some studies of the composition and surface of oil bodies from the seed cotyledons of safflower and linseed. *Biochem. J.* 190: 551-561.

Tai S S, Chen M C, Peng C C, Tzen J T. (2002). Gene family of oleosin isoforms and their structural stabilization in sesame seed oil bodies. *Biosci. Biotech. Biochem.* 66(10): 2146-2153.

Takaiwa F, Yamanouchi U, Yoshihara T, Washida H, Tanabe F, Kato A, Yamada K. (1996). Characterization of common cis-regulatory elements responsible for the endosperm-specific expression of members of the rice glutelin multigene family. *Plant Mol. Biol.* (30): 1207-1221.

Tan B C, Joseph L M, Deng W T, Liu L, Li Q B, Cline K, McCarty D. (2003). Molecular characterization of the *Arabidopsis* 9-cis epoxycarotenoid dioxygenase gene family. *Plant J.* 35: 1-13.

Thomas T L. (1993). Gene expression during embryogenesis and germination: an overview. *Plant Cell* (5): 1401-1410.

Thoyts P J, Millichip M I, Stobart A K, Griffiths W T, Shewry P R, Napier J A. (1995). Expression and in vitro targeting of a sunflower oleosin. *Plant Mol. Biol.* 29 (2): 403-410.

Ting J T L, Lee K, Ratnayake C, Platt K A, Balsamo R A, and Huang A H C. (1996). Oleosin genes in maize kernels having diverse oil contents are constitutively expressed independent of oil contents. Size and shape of intracellular oil bodies are determined by oleosins/oil ratio. *Planta*, 199: 158-165.

Tzen J T C, Cao Y Z, Laurent P, Ratnayake C, Huang A H C. (1993). Lipids, proteins, and structure of seed oil bodies from diverse species. *Plant Physiol.*, 101: 267-276.

Tzen J T C, Chuang R L C, Chen J C F, Wu L S H. (1998). Coexistence of both oleosin isoforms on the surface of seed oil bodies and their individual stabilization to the organelles. *J. Biochem.*, 123: 318-323.

Tzen J T C, Lai Y K, Chan K L, Huang A H C. (1990). Oleosin isoforms of high and low molecular weights are present in the oil bodies of diverse seed species. *Plant Physiol.*, 94: 1282-1289.

Variyar P S, Ahmad R, Bhat R, Niyas Z, Sharma A. (2003). Flavoring components of raw monsooned arabica coffee and their changes during radiation processing. *J Agric Food Chem.* 51(27):7945-7950.

Washida H, Wu C Y, Suzuki A, Yamanouchi U, Akihama T, Harada K, Takaiwa F. (1999). Identification of cis-regulatory elements required for endosperm expression of the rice storage protein glutelin gene Glub-1. *Plant Mol. Biol.* (40) 1-12.

Wahlroos T, Soukka J, Denesyuk A, Wahlroos R, Korpela T, Kilby N J. (2003). Oleosin expression and trafficking during oil body biogenesis in tobacco leaf cells. *Genesis* 35: 125-132.

Wu L S H, Hong G H H, Hou R F, Tzen J T C. (1999). Classification of the single oleosin isoform and characterization of seed oil bodies in gymnosperms. *Plant Cell Physiol.* 40: 326-334.

Wu L S H, Wang L D, Chen P W, Chen L J, Tzen J T. (1998). Genomic cloning of 18 kDa oleosin and detection of traicymglycerol and oleosin isoforms in maturing nice post-germination seeds. *J. Biochem.* 123(3): 386-391.

Zheng Z, Kawagoe Y, Xiao S, Li Z, Okita T, Hau T L, Lin A, Murai N. (1993). 5' distal and proximal cis-acting regulatory elements are required for developmental control of a rice seed storage protein gene. *Plant J.* (4) 357-366.

The present invention is not limited to the embodiments described and exemplified above, but is capable of variation and modification within the scope of the appended claims.

---

What is claimed is:

1. A nucleic acid molecule isolated from coffee (*Coffea* spp.), having a coding sequence that encodes a peptide comprising an amino acid sequence that is substantially the same as one or more fragments selected from the group consisting of:
   a) residues 1 to about 27, about 28 to about 109, or about 110 to the C-terminus of SEQ ID NO:8 or SEQ ID NO:9;
   b) residues 1 to about 15, about 16 to about 89, or about 90 to the C-terminus of SEQ ID NO:10;
   c) residues 1 to about 30, about 31 to about 114, or about 115 to the C-terminus of SEQ ID NO:11;
   d) residues 1 to about 18, about 19 to about 89, or about 90 to the C-terminus of SEQ ID NO:12; and
   e) residues 1 to about 40, about 41 to about 115, or about 116 to the C-terminus of SEQ ID NO:13.

2. The nucleic acid molecule of claim 1, wherein the coding sequence encodes a peptide having a molecular weight of between about 14 kDa and about 19 kDa.

3. The nucleic acid molecule of claim 2, wherein the peptide comprises an oleosin.

4. The nucleic acid molecule of claim 3, wherein the oleosin has an amino acid sequence that is substantially the same as any one of SEQ ID NOS: 8-13.

5. The nucleic acid molecule of claim 4, wherein the oleosin has the amino acid sequence of any one of SEQ ID NOS: 8-13.

6. The nucleic acid molecule of claim 4, wherein the coding sequence is substantially the same as any one of the coding sequences set forth in SEQ ID NOS: 1-6.

7. The nucleic acid molecule of claim 6, wherein the coding sequence comprises any one of SEQ ID NOS: 1-6.

8. A vector comprising the nucleic acid molecule of claim 1.

9. The vector of claim 8, wherein the coding sequence of the nucleic acid molecule is operably linked to a constitutive promoter.

10. The vector of claim 8, wherein the coding sequence of the nucleic acid molecule is operably linked to an inducible promoter.

11. The vector of claim 8, wherein the coding sequence of the nucleic acid molecule is operably linked to a tissue specific promoter.

12. The vector of claim 11, wherein the tissue specific promoter is a seed specific promoter.

13. The vector of claim 12, wherein the seed specific promoter is a coffee seed specific promoter.

14. The vector of claim 13, wherein the coffee seed specific promoter is an oleosin gene promoter.

15. The vector of claim 14, wherein the oleosin gene promoter comprises SEQ ID NO:15.

16. A method to modulate flavor or aroma of coffee beans, comprising transforming or transfecting a coffee plant or a portion thereof with the vector of claim 8, and modulating production of one or more oleosins within the seeds of the coffee plant through the use of said vector.

17. A promoter isolated from a coffee plant gene, wherein the coding sequence of the gene encodes an oleosin, and wherein the promoter comprises a nucleic acid sequence substantially the same as SEQ ID NO:15.

18. The promoter of claim 17, comprising one or more regulatory sequences selected from the group consisting of TTAAAT, TGTAAAGT, CAAATG, CATGTG, CATG-CAAA, CCATGCA and ATATTTATT.

19. The promoter of claim 18, comprising SEQ ID NO:15.

20. The promoter of claim 17, operably linked to one or more coding sequences to form a chimeric gene.

* * * * *